United States Patent
Baker et al.

(10) Patent No.: US 12,205,720 B2
(45) Date of Patent: Jan. 21, 2025

(54) DIGITAL QUALIMETRIC BIOMARKERS FOR COGNITION AND MOVEMENT DISEASES OR DISORDERS

(71) Applicant: Hoffmann-La Roche Inc., Little Falls, NJ (US)

(72) Inventors: Mike Baker, Basel (CH); Shibeshih Mitiku Belachew, Basel (CH); Christian Gossens, Basel (CH); Michael Lindemann, Reinach (CH); Jörg Sprengel, Reinach (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 550 days.

(21) Appl. No.: 16/856,865

(22) Filed: Apr. 23, 2020

(65) Prior Publication Data

US 2020/0258631 A1    Aug. 13, 2020

Related U.S. Application Data

(63) Continuation of application No. PCT/EP2018/079284, filed on Oct. 25, 2018.

(30) Foreign Application Priority Data

Oct. 25, 2017   (EP) .................................. 17198323
May 9, 2018     (EP) .................................. 18171569

(51) Int. Cl.
*G16H 50/20*    (2018.01)
*A61B 5/00*     (2006.01)
(Continued)

(52) U.S. Cl.
CPC ........... *G16H 50/20* (2018.01); *A61B 5/1101* (2013.01); *A61B 5/1118* (2013.01);
(Continued)

(58) Field of Classification Search
CPC ........ G16H 10/00; G16H 10/20; G16H 10/40; G16H 15/00; G16H 20/00; G16H 20/10;
(Continued)

(56) References Cited

U.S. PATENT DOCUMENTS

2005/0107682 A1* 5/2005 Rao .................. A61B 5/4088
                                                       424/9.2
2005/0273017 A1* 12/2005 Gordon ............ A61B 5/4088
                                                       600/544
(Continued)

OTHER PUBLICATIONS

Graça et al. 2014, "ParkDetect: Early diagnosing Parkinson's Disease," 2014 IEEE International Symposium on Medical Measurements and Applications (MeMeA), Lisboa, Portugal, 2014, pp. 1-6, doi: 10.1109/MeMeA.2014.6860027.*

(Continued)

*Primary Examiner* — Robert W Morgan
*Assistant Examiner* — Charles P Coleman
(74) *Attorney, Agent, or Firm* — Bose McKinney & Evans LLP

(57) ABSTRACT

Disclosed is a method for assessing a cognition and movement disease or disorder in a subject. In the method, a qualimetric activity parameter for cognition and/or fine motoric activity measurements is determined from a dataset of measurements obtained from the subject using a mobile device. The qualimetric activity parameter is compared to a reference and the disease or disorder is thereby assessed. A method identifying whether a subject will benefit from a therapy for a cognition and movement disease or disorder is also disclosed. The method can be carried out with a mobile device having a processor, a sensor and a database as well as software that carries out the method. Also disclosed is a system having a mobile device with a sensor and a remote device having a processor and a database and software that (Continued)

carries out the method for assessing a cognition and movement disease or disorder.

28 Claims, 24 Drawing Sheets

(51) Int. Cl.

| | | |
|---|---|---|
| *A61B 5/11* | (2006.01) | |
| *A61B 5/16* | (2006.01) | |
| *G16H 10/60* | (2018.01) | |
| *G16H 20/17* | (2018.01) | |
| *G16H 20/30* | (2018.01) | |
| *G16H 20/60* | (2018.01) | |
| *G16H 20/70* | (2018.01) | |
| *G16H 40/67* | (2018.01) | |
| *G16H 50/30* | (2018.01) | |
| *G16H 50/50* | (2018.01) | |
| *G16H 50/70* | (2018.01) | |
| *G16H 70/60* | (2018.01) | |

(52) U.S. Cl.
CPC .......... *A61B 5/1124* (2013.01); *A61B 5/1125* (2013.01); *A61B 5/165* (2013.01); *A61B 5/168* (2013.01); *A61B 5/4082* (2013.01); *A61B 5/4088* (2013.01); *A61B 5/7267* (2013.01); *A61B 5/7282* (2013.01); *G16H 10/60* (2018.01); *G16H 20/17* (2018.01); *G16H 20/30* (2018.01); *G16H 20/60* (2018.01); *G16H 20/70* (2018.01); *G16H 40/67* (2018.01); *G16H 50/30* (2018.01); *G16H 50/50* (2018.01); *G16H 50/70* (2018.01); *G16H 70/60* (2018.01)

(58) Field of Classification Search
CPC ........ G16H 20/13; G16H 20/17; G16H 30/00; G16H 40/00; G16H 50/00; G16H 70/00; G16H 80/00; G16H 50/20; G16H 40/67; G16H 70/60; G16H 50/50; G16H 10/60; G16H 50/30; G16H 50/70; G16H 20/60; G16H 20/70; G06Q 50/22–24; A61B 5/1101; A61B 5/1118; A61B 5/1124; A61B 5/1125; A61B 5/165; A61B 5/168; A61B 5/4082; A61B 5/4088; A61B 5/7267; A61B 5/7282
USPC .................... 705/2–3, 20; 600/595
See application file for complete search history.

(56) References Cited

U.S. PATENT DOCUMENTS

| | | | | |
|---|---|---|---|---|
| 2010/0298649 | A1* | 11/2010 | Warkentin ........... | A61B 5/4803 436/98 |
| 2012/0330182 | A1* | 12/2012 | Alberts ................ | G16H 50/30 607/45 |
| 2014/0153794 | A1 | 6/2014 | Varaklis et al. | |
| 2014/0330159 | A1* | 11/2014 | Costa .................... | A61B 5/16 600/595 |
| 2015/0179079 | A1 | 6/2015 | Rodriguez, Jr. et al. | |
| 2015/0216414 | A1 | 8/2015 | Wood et al. | |
| 2015/0220693 | A1* | 8/2015 | Cadavid ................ | G16H 50/20 702/19 |
| 2016/0100788 | A1 | 4/2016 | Sano et al. | |
| 2016/0364549 | A1* | 12/2016 | Wei ....................... | G16H 10/60 |
| 2017/0251985 | A1* | 9/2017 | Howard ................ | G16H 70/60 |
| 2017/0258390 | A1* | 9/2017 | Howard ................ | A61B 5/369 |
| 2018/0070823 | A1* | 3/2018 | Blackwell ............. | G16H 40/63 |
| 2020/0258631 | A1* | 8/2020 | Baker ................... | G16H 10/60 |

OTHER PUBLICATIONS

Anzulewicz et al. 2016, "Toward the Autism Motor Signature: Gesture patterns during smart tablet gameplay identify children with autism," Sci Rep. Aug. 24, 2016;6:31107. doi: 10.1038/srep31107. PMID: 27553971; PMCID: PMC4995518.*

Aktas et al., Neuronal Damage in Autoimmune Neuroinflammation Mediated by the Death Ligand Trail, Neuron, May 5, 2005, pp. 421-432, vol. 46.

Zamvil et al., Diverse Targets for Intervention During Inflammatory and Neurodegenerative Phases of Multiple Sclerosis, Neuron, Jun, 5, 2003, pp. 685-688, vol. 38.

Crawford et al., Primary T Cell Expansion and Differentiation In Vivo Requires Antigen Presentation by B Cells, J. Immunology, 2006, pp. 3498-3506, vol. 176.

Bar-Or et al., Abnormal B-Cell Cytokine Responses: A Trigger of T-Cell-Mediated Disease in MS?, Annals of Neurology, Apr. 2010, pp. 452-461, vol. 67.

Lisak et al., Secretory Products of Multiple Sclerosis B Cells Are Cytotoxic to Oligodendroglia In Vitro, J. Neuroimmunology, 2012, pp. 85-95, vol. 246.

Weber et al., The Role of Antibodies in Multiple Sclerosis, Biochemica et Biophysica Acta, 2011, pp. 239-245, vol. 1812.

Serafini et al., Detection of Ectopic B-Cell Follicles with Germinal Centers in the Meninges of Patients with Secondary Progressive Multiple Sclerosis, Brain Pathology, 2004, pp. 164-174, vol. 14.

Magliozzi et al., A Gradient of Neuronal Loss and Meningeal Inflammation in Multiple Sclerosis, Annals of Neurology, 2010, pp. 477-493, vol. 68.

Bove et al., Evaluating More Naturalistic Outcome Measures: A 1-Year Smartphone Study in Multiple Sclerosis, Neurology: Neuroimmunology & Neuroinflammation, 2015, 10 pgs.

Link et al., Oligoclonal Bands in Multiple Sclerosis Cerebrospinal Fluid: An Update on Methodology and Clinical Usefulness, J. Neuroimmunology, 2006, pp. 17-28, vol. 180.

Tsang et al., Multiple Sclerosis: Diagnosis, Management and Prognosis, Australian Family Physician, Dec. 2011, pp. 948-955, vol. 40.

Compston et al., Multiple Sclerosis, Lancet, Oct. 25, 2008, pp. 1502-1517, vol. 372.

Johnston et al., First-Line Disease-Modifying Therapies in Paediatric Multiple Sclerosis: A Comprehensive Overview, Drugs, 2012, pp. 1195-1211, vol. 72.

Donnan et al., Stroke, Lancet, May 10, 2008, pp. 1612-1623, vol. 371.

Harbison et al., Rapid Ambulance Protocol for Acute Stroke, Lancet, Jun. 5, 1999, p. 1935, vol. 353.

Kidwell et al., Design and Retrospective Analysis of the Los Angeles Prehospital Stroke Screen (LAPSS), Prehospital Emergency Care, 1998, pp. 267-273, vol. 2.

Nor et al., The Recognition of Stroke in the Emergency Room (ROSIER) Scale: Development and Validation of a Stroke Recognition Instrument, Lancet Neurology, 2005, pp. 727-734, vol. 4.

Pasquier, Early Diagnosis of Dementia: Neuropsychology, J. Neurology, 1999, pp. 6-15, vol. 246.

Jankovic, Parkinson's Disease: Clinical Features and Diagnosis, J. Neurology Neurosurgery, and Psychiatry, 2008, pp. 368-376, vol. 79.

Impressum Neurostatus, https://neurostatus.net (last visited Aug. 18, 2020).

Dayalu et al., Huntington Disease: Pathogenesis and Treatment, Neurol. Clin., 2015, pp. 101-114, vol. 33.

Frank, Treatment of Huntington's Disease, NeuroTherapeutics, 2014, pp. 153-160, vol. 11.

Rao et al., Clinical Measurement of Mobility and Balance Impairments in Huntington's Disease: Validity and Responsiveness, Gait & Posture, 2009, pp. 433-436, vol. 29.

Robert et al., Grouping for Behavioral and Psychological Symptoms in Dementia: Clinical and Biological Aspects, European Psychiatry, 2005, pp. 490-496, vol. 20.

Zarei et al., A Comprehensive Review of Amyotrophic Lateral Sclerosis, Surgical Neurology International, Nov. 16, 2015, 23 pgs.

(56) References Cited

OTHER PUBLICATIONS

Polman et al., Diagnostic Criteria for Multiple Sclerosis: 2010 Revisions to the McDonald Criteria, Annals of Neurology, 2011, pp. 292-302, vol. 69.
Lublin et al., Defining the Clinical Course of Multiple Sclerosis: The 2013 Revisions, Neurology, Jul. 15, 2014, pp. 278-286, vol. 83.
Burns et al., The Evaluation of Polyneuropathies, Neurology Clinical Practice, Feb. 15, 2011, pp. S6-S13, vol. 76 suppl. 2.
Waldemar et al., Recommendations for the Diagnosis and Management of Alzheimer's Disease and Other Disorders Associated with Dementia: EFNS Guideline, European J. Neurology, 2007, pp. e1-e26, vol. 14.
Bäckman et al., Multiple Cognitive Deficits During the Transition to Alzheimer's Disease, J. Internal Medicine, 2004, pp. 195-204, vol. 256.
Cheon et al., Leukodystrophy in Children: A Pictorial Review of MR Imaging Features, RadioGraphics, 2002, pp. 461-476, vol. 22.
Todd et al., Survival in Dementia and Predictors of Mortality: A Review, Int. J. Geriatric Psychiatry, 2013, pp. 1109-1124, vol. 28.
Walker, Huntington's Disease, Lancet, Jan. 20, 2007, pp. 218-228, vol. 369.
Gunstad et al., Patterns of Cognitive performance in Middle-Aged and Older Adults: A Cluster Analytic Examination, J. Geriatric Psychiatry and Neurology, Jun. 2006, pp. 59-64, vol. 19.
Strawn et al., Neuroleptic Malignant Syndrome, Am. J. Psychiatry, Jun. 2007, pp. 870-876, vol. 164.
Alsheikh et al., Deep Activity Recognition Models with Triaxial Accelerometers, Workshops of the Thirtieth AAAI Conference on Artificial Intelligence, 2016, 7 pgs.
Ordóñez et al., Deep Convolutional and LSTM Recurrent Neural Networks for Multimodal Wearable Activity Recognition, Sensors, 2016, 25 pgs.
Hobart et al., The Multiple Sclerosis Impact Scale (MSIS-29) A New Patient-Based Outcome Measure, Brain, 2001, pp. 962-973, vol. 124.
Wai et al., iBEST: intelligent Balance Assessment and Stability Training System using Smartphone, IEEE, 2014, pp. 3683-3686.
Van De Pol et al., Magnetic Resonance Imaging Predictors of Cognition in Mild Cognitive Impairment, Arch Neurol, Jul. 2007, pp. 1023-1028.
Berg et al., Measuring Balance in the Elderly: Validation of an Instrument, Canadian Journal of Public Health, Jul./Aug. 1992 (Supp.), pp. S7-S11.
Costa et al., Information processing speed in multiple sclerosis: Past, present and future, Multiple Sclerosis Journal, 2017, pp. 772-789.
Hobart et al., Timed 25-Foot Walk, American Academy of Neurology, 2013, pp. 1509-1517.
Rao et al., Processing speed test: Validation of a self-administered, iPad®-based tool for screening cognitive dysfunction in a clinic setting, Multiple Sclerosis Journal, 2017, pp. 1929-1937.
Burns et al., Alzheimer's disease, The BMJ, Feb. 21, 2009, pp. 467-471, vol. 338.
Smith et al., The symbol-digit modalites test: a neuropsychologic test of learning and other cerebraldisorders, Learning Disorders, 1968, pp. 83-91, vol. 3.
Vanotti et al., Cognitive performance of neuromyelitis optica patients: comparison with multiple sclerosis, Arquivo de Neuro-Psiquiatria, 2013, pp. 357-361, vol. 71(6).
Blanc et al., Cognitive Functions in Neuromyelitis Optica, Arch Neurol., Jan. 2008, pp. 84-88, vol. 65(1).
A Study of Ocrelizumab in Participants with Primary Progressive Multiple Sclerosis, Dec. 26, 2017, https://clinicaltrials.gov/ct2/show/NCT01194570.
A Study of Ocrelizumab in Comparison with Interferon Beta-1a (Rebif) in Participants with Relapsing Multiple Sclerosis, Jul. 18, 2017, https://clinicaltrials.gov/ct2/show/NCT01412333.
A Study of the Efficacy and Safety Ocrelizumab in Patients with Relapsing-Remitting Multiple Sclerosis, May 11, 2017, https://clinicaltrials.gov/ct2/show/NCT00676715.
A Study of Ocrelizumab in Comparison with Interferon Beta-1a (Rebif) in Participants with Relapsing Multiple Sclerosis, Jul. 18, 2017, https://clinicaltrials.gov/ct2/show/NCT01247324.
International Search Report and Written Opinion of the International Searching Authority, PCT/EP2018/079284, Jun. 11, 2019 18 pages.
International Preliminary Report on Patentability, PCT/EP2018/079284 Apr. 28, 2020, 11 pages.
Saji et al., Cognitive Impairment and Cortical Degeneration in Neuromyelitis Optica, American Neurological Association, 2012, pp. 65-76, vol. 73.
Zappos et al., Ocrelizumab in relapsing-remitting multiple sclerosis: a phase 2, randomised, placebo-controlled, multicentre trial, The Lancet, Nov. 19, 2011, pp. 1779-1787, vol. 378(9805).

\* cited by examiner

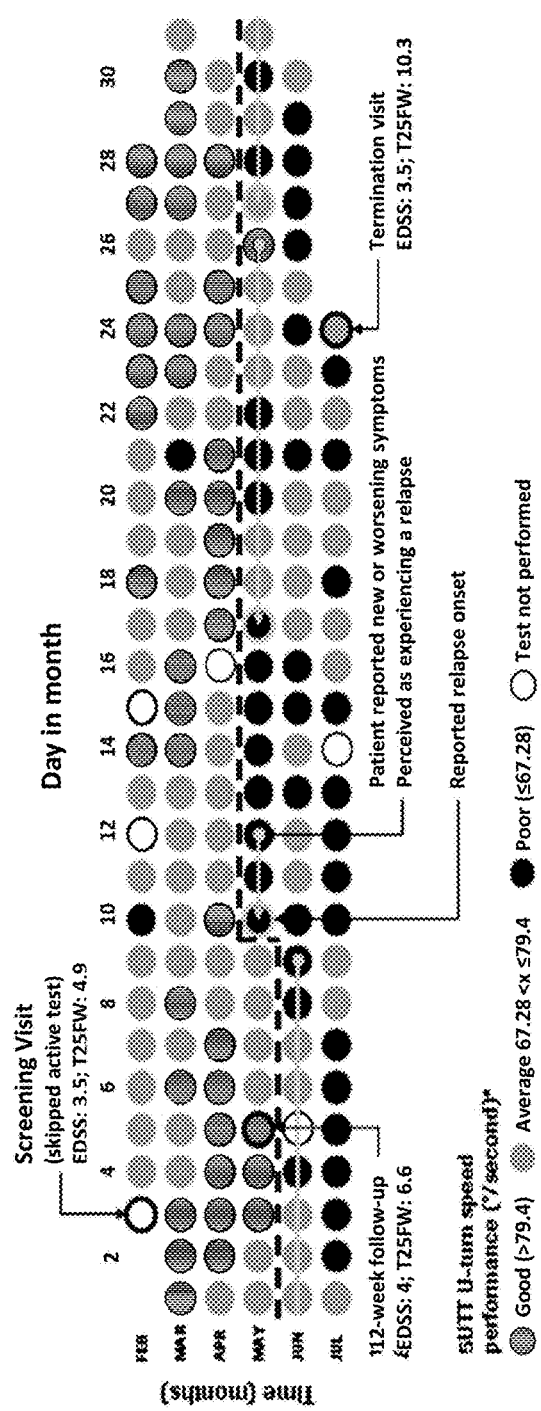
Fig. 4A
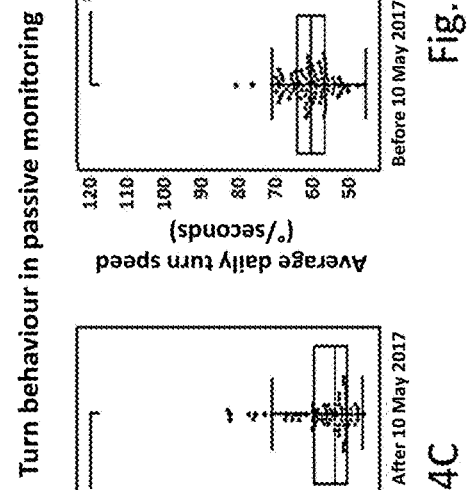
Fig. 4D
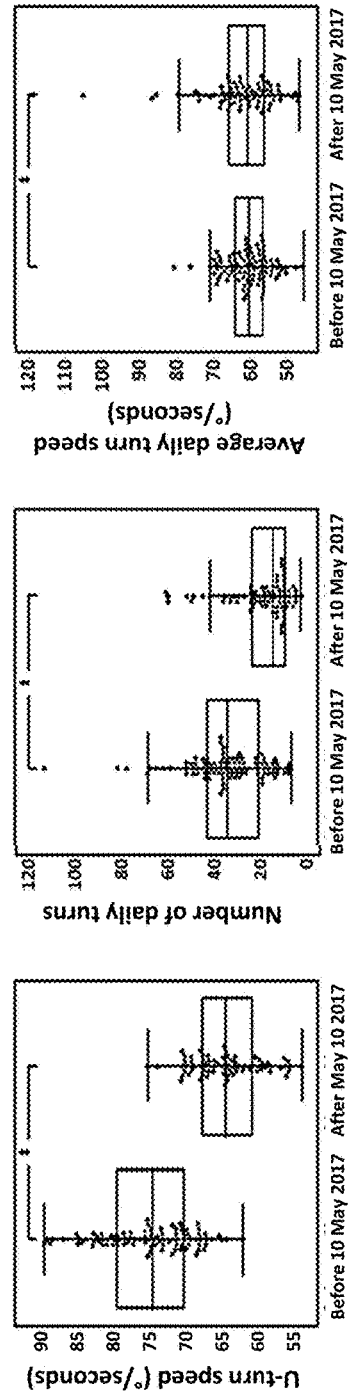
Fig. 4C
Fig. 4B

DIGITAL QUALIMETRIC BIOMARKERS FOR COGNITION AND MOVEMENT DISEASES OR DISORDERS

RELATED APPLICATIONS

This application is a continuation of PCT/EP2018/079284, filed Oct. 25, 2018, which claims priority to EP 18 171 569.9, filed May 9, 2018, and EP 17 198 323.2, filed Oct. 25, 2017, the entire disclosures of all of which are hereby incorporated herein by reference.

BACKGROUND

The present disclosure relates to the field of diagnostics. More specifically, it concerns a method for assessing a cognition and movement disease or disorder in a subject suspected to suffer therefrom comprising the steps of determining at least one qualimetric activity parameter for cognition and/or fine motoric activity from a dataset of cognition and/or fine motoric activity measurements obtained from said subject using a mobile device and comparing the determined at least one qualimetric activity parameter to a reference, whereby the cognition and movement disease or disorder will be assessed. The present disclosure also relates to a method for identifying whether a subject will benefit from a therapy for a cognition and movement disease or disorder comprising the aforementioned steps and the further step of identifying the subject as a subject that benefits from the therapy if the cognition and movement disease or disorder is assessed. The present disclosure contemplates a mobile device comprising a processor, at least one sensor and a database as well as software which is tangibly embedded to said device and, when running on said device, carries out the disclosed method, a system comprising a mobile device comprising at least one sensor and a remote device comprising a processor and a database as well as software which is tangibly embedded to said device and, when running on said device, carries out the method and the use of the mobile device or system according to the disclosure for assessing a cognition and movement disease or disorder in a subject.

Cognition and movement diseases and disorders are typically characterized by impaired cognitive and/or motoric functions. The diseases and disorders are less frequent but nevertheless typically accompanied by severe complications for the affected patients in daily life. Various cognition and movement disorders may result in life-threatening conditions and are finally mortal.

The diseases and disorders have in common that impaired function of the central nervous system, the peripheral nervous system and/or the muscular system results in cognition and movement disabilities. The movement disabilities may be primary disabilities due to direct impairments of muscle cells and function or may be secondary disabilities caused by impairments of muscle control by the peripheral and/or central nervous system central, in particular, the pyramidal, extrapyramidal, sensory or cerebellar system. The impairment may involve damage, degradation, intoxication or injury of nervous and/or muscular cells.

Typical cognition and movement diseases and disorders include but are not limited to multiple sclerosis (MS), neuromyelitis optica (NMO) and NMO spectrum disorders, stroke, a cerebellar disorder, cerebellar ataxia, spastic paraplegia, essential tremor, myasthenia and myasthenic syndromes or other forms of neuromuscular disorders, muscular dystrophy, myositis or other muscular disorders, a peripheral neuropathy, cerebral palsy, extrapyramidal syndromes, Parkinson's disease, Huntington's disease, Alzheimer's disease, other forms of dementia, leukodystrophies, autism spectrum disorders, attention-deficit disorders (ADD/ADHD), intellectual disabilities as defined by DSM-5, impairment of cognitive performances and reserve related to aging, a polyneuropathy, motor neuron diseases and amyotrophic lateral sclerosis (ALS).

Among the most commonly known and severe diseases and disorders there are MS, stroke, Alzheimer's disease, Parkinson's disease, Huntington's disease and ALS.

Multiple sclerosis (MS) is a severe neurodegenerative disease which at present cannot be cured. Affected by this disease are approximately 2 to 3 million individuals worldwide. It is the most common disease of the central nervous system (CNS) that causes prolonged and severe disability in young adults. There is evidence supporting the concept that a B- and T cell-mediated inflammatory process against self-molecules within the white matter of the brain and spinal cord causes the disease. However, its etiology is still not well understood. It has been found that myelin-reactive T cells are present in both MS patients and healthy individuals. Accordingly, the primary abnormality in MS may involve more likely an impaired regulatory mechanism leading to an enhanced T cell activation status and less stringent activation requirements. The pathogenesis of MS includes activation of encephalitogenic, i.e., autoimmune myelin-specific T cells outside the CNS, followed by an opening of the blood-brain barrier, T cell and macrophage infiltration, microglia activation and demyelination. The latter causes irreversible neuronal damage (see, e.g., Aktas 2005, Neuron 46, 421-432, Zamvil 2003, Neuron 38:685-688).

It was shown more recently that besides T cells, B lymphocytes (expressing CD20 molecule) may play a central role in MS and influence the underlying pathophysiology through at least four specific functions:

1. Antigen presentation: B cells can present self neuroantigens to T cells and activate them (Crawford A, et al. J Immunol 2006;176(6):3498-506; Bar-Or A, et al. Ann Neurol 2010;67(4):452-61)
2. Cytokine production: B cells in patients with MS produce abnormal proinflammatory cytokines, which can activate T cells and other immune cells (Bar-Or A, et al. Ann Neurol 2010;67(4):452-61; Lisak R P, et al. J Neuroimmunol 2012;246(1-2):85-95)
3. Autoantibody production: B cells produce autoantibodies that may cause tissue damage and activate macrophages and natural killer (NK) cells (Weber M S, et al. Biochim Biophys Acta 2011;1812(2):239-45)
4. Follicle-like aggregate formation: B cells are present in ectopic lymphoid follicle-like aggregates, linked to microglia activation, local inflammation, and neuronal loss in the nearby cortex (Serafini B, et al. Brain Pathol 2004;14(2):164-74; Magliozzi R, et al. Ann Neurol 2010;68(4):477-93)

Although there is sound knowledge about the mechanisms responsible for the encephalitogenicity, far less is known regarding the control mechanisms for regulating harmful lymphocyte responses into and within the CNS in a subject.

MS diagnosis is based at present on clinical investigations by a medical practitioner. Such investigations involve testing of the capabilities of a patient for certain physical activities. Several tests have been developed and are routinely applied by medical practitioners. These tests aim at assessing walking, balance, and other motoric abilities.

Examples of currently applied tests are the Expanded Disability Status Scale (EDSS, www.neurostatus.net) or Multiple Sclerosis Functional Composite (MSFC). These tests require the presence of a medical practitioner for evaluation and assessment purposes and are currently performed ambulant at doctor's offices or hospitals. Very recently, there have been some efforts in monitoring MS patients using smartphone devices in order to collect data of MS patients in a natural setting (Bove 2015, Neurol Neuroimmunol Neuroinflamm 2 (6):e162).

Further, diagnostic tools are used in MS diagnosis. Such tools include neuroimaging, analysis of cerebrospinal fluid and evoked potentials. Magnetic resonance imaging (MRI) of the brain and spinal cord can visualize demyelination (lesions or plaques). Contrast agents containing gadolinium can be administered intravenously to mark active plaques and, differentiate acute inflammation from the existence of older lesions which are not associated with symptoms at the moment of the evaluation. The analysis of cerebrospinal fluid obtained from a lumbar puncture can provide evidence of chronic inflammation of the central nervous system. The cerebrospinal fluid can be analyzed for oligoclonal immunoglobulin bands, which are an inflammation marker present in 75-85% of people with MS (Link 2006, J Neuroimmunol. 180 (1-2): 17-28). However, none of the aforementioned techniques is specific to MS. Therefore, ascertainment of diagnosis may require repetition of clinical and MRI investigations to demonstrate dissemination in space and in time of the disease which is a prerequisite to MS diagnosis.

There are several treatments approved by regulatory agencies for relapsing-remitting multiple sclerosis which modify the course of the disease. These treatments include interferon beta-1a, interferon beta-1b, glatiramer acetate, mitoxantrone, natalizumab, fingolimod, teriflunomide, dimethyl fumarate, alemtuzumab, and daclizumab. The interferons and glatiramer acetate are first-line treatments that reduce relapses by approximately 30% (see, e.g., Tsang 2011, Australian family physician 40 (12): 948-55). Natalizumab reduces the relapse rate more than the interferons, however, due to issues of adverse effects it is a second-line agent reserved for those who do not respond to other treatments or patients with severe disease (see, e.g., Tsang 2011, loc. cit.). Treatment of clinically isolated syndrome (CIS) with interferons decreases the chance of progressing to clinically definite MS (Compston 2008, Lancet 372(9648): 1502-17). Efficacy of interferons and glatiramer acetate in children has been estimated to be roughly equivalent to that of adults (Johnston 2012, Drugs 72 (9): 1195-211).

Recently, new monoclonal antibodies such as ocrelizumab, alemtuzumab and daclizumab have shown potential as therapeutics for MS. The anti-CD20 B-cell targeting monoclonal antibody ocrelizumab has shown beneficial effects in both relapsing and primary progressive forms of MS in one phase 2 and 3 phase III trials (NCT00676715, NCT01247324, NCT01412333, NCT01194570).

MS is a clinically heterogeneous inflammatory disease of the CNS. Therefore, diagnostic tools are needed that allow a reliable diagnosis and identification of the present disease status and can, thus, aid in accurate treatment, in particular, for those patients suffering for progressing forms of MS. Improvements in monitoring of disease progression are also highly desired.

Stroke may occur as an ischemic stroke where the blood support is impaired due to obstruction of blood vessels or as hemorrhagic stroke resulting from injury of vessels and bleeding.

Signs and symptoms of a stroke may include typically one-sided movement/motoric or sensory impairments, problems walking, speaking, hearing, spinning vertigo or abnormalities of vision (Donnan 2008, Lancet. 371 (9624): 1612-23). Said signs and symptoms often appear immediately or soon after the stroke has occurred. If symptoms last less than one or two hours it is known as a transient ischemic attack. Hemorrhagic strokes may also be accompanied by severe headache. The symptoms of a stroke can be permanent. Long term comorbid complications may include pneumonia or loss of bladder control.

The early diagnosis and treatment of stroke is decisive for the outcome. Current stroke diagnosis requires imaging techniques such as magnetic resonance imaging (MRI) scanning, Doppler ultrasound, or angiography, as well as neurological examination by a medical practitioner (see, e.g., Harbison 1999, Lancet. 353 (9168): 1935; Kidwell 1998, Prehospital Emergency Care. 2 (4): 267-73; Nor 2005, Lancet Neurology. 4 (11): 727-34).

There are more than 10 million people affected by stroke every year. In the developed world, stroke management has become more efficient due to stroke units. However, these specialized centers are not present in less developed parts of the world outside of urban regions. The early detection of the disorder has a major influence on the outcome of stroke in patients. Accordingly, there is a need for early detection of signs and symptoms of stroke outside of the competent stroke units and hospitals. Beyond stroke detection there is also a crucial need for properly assessing mid- to long-term disability outcomes associated with acute stroke treatment intervention, as well as spontaneous and rehabilitation program-related recovery.

Alzheimer's disease is a severe and mortal neurodegenerative disease accompanied by dementia and associated problems. In fact, Alzheimer's disease is responsible for 60 to 70% of all cases of dementia. An early symptom of the disease is a reduced short-term memory. Subsequent symptoms include social symptoms such as withdrawal from family and society, as well as physical symptoms such as loss of body functions (Burns 2009, The BMJ. 338: b158).

Diagnosis of Alzheimer's disease is based on imaging techniques such as CT, MRI, SPECT or PET. Moreover, neurological assessments are carried out by medical practitioners including tests for assessment of cognitive functions (Pasquier 1999, Journal of Neurology 246 (1):6-15). Typical tests include tests where people are instructed to copy drawings similar to the one shown in the picture, remember words, read, and subtract serial numbers. Usually, caregivers are required for the diagnosis since the Alzheimer's disease patient him/herself is unaware of his/her deficits. There is no efficient disease-modifying treatment or cure yet for Alzheimer's disease. However, for efficient disease management, a reliable and early diagnosis is helpful.

Alzheimer's disease affects about 50 million people worldwide and may be one of the most frequent neurodegenerative diseases in the elderly. Accordingly, there is a need for early detection of signs and symptoms for a proper management of the disease as well as a need for monitoring of disease progression.

Parkinson's disease is a neurodegenerative disease of the central nervous system that pivotally affects the motoric system. Typical symptoms are resting tremor, postural instability, shaking, rigidity, slowness of movement, and difficulties with walking. Dementia and depression and sensory, autonomous nervous system and sleeping problems may also occur at more severe stages of the disease. The motoric problems are caused by degeneration of neurons in the substantia nigra of the midbrain resulting in a significant alteration of dopaminergic neurotransmission. There is no cure for the Parkinson's disease available yet.

Diagnosis of Parkinson's disease is based on neurological assessments together with imaging methods, such as CT, MRI, PET or SPECT scanning. Neurological criteria for the diagnosis of the disease include the assessment of bradykinesia, rigidity, resting tremor and postural instability (Jankovic 2008, Journal of Neurology, Neurosurgery, and Psychiatry. 79 (4): 368-376).

More than 50 million people are affected by Parkinson's disease. There is a need for an early and reliable diagnosis of this neurodegenerative disease as well as monitoring disease progression.

Huntington's disease is an inherited disorder that results in death of neurons in the central nervous system and, in particular, in the brain. The earliest symptoms are often subtle problems with mood or mental abilities. However, general impairment of coordination and an unsteady gait typically occurs afterwards (Dayalu 2015, Neurologic Clinics. 33 (1): 101-14) In its advanced stages, uncoordinated body movements become apparent and physical abilities gradually worsen until coordinated movement becomes difficult and the person is unable to speak. The cognitive capabilities are also impaired and may decline into dementia (Frank 2014, The Journal of the American Society for Experimental NeuroTherapeutics. 11 (1): 153-60) The specific symptoms may, however, individually vary. There is no cure for Huntington's disease available yet.

Since Huntington's disease is inherited in a dominant autosomal manner, genome testing for CAG repeats in the huntingtin (HTT) alleles is recommended for individuals being genetically at risk, i.e., patients with a corresponding family history of the disease. Moreover, diagnosis of the disease involves DNA analysis, but also imaging methods such as CT, MRI, PET or SPECT scanning in order to determine cerebral atrophy, as well as neurological assessment by a medical practitioner. In particular, the neurological assessments can be carried out according to the criteria for the unified Huntington's diseases rating scale system (Rao 2009, Gait Posture. 29 (3): 433-6).

Huntington's disease is less frequent than Alzheimer's disease and Parkinson's disease. However, it is still a cognition and movement disease or disorder affecting a significant proportion of people with severe and life-threatening complications. There is a need for an early and reliable diagnosis of this neurodegenerative disease as well as monitoring disease progression.

ALS is a neurodegenerative disease that involves cell death of the lower and upper motor neurons that control voluntary muscle contraction (Zarei 2015, Surgical Neurology International. 6: 171). ALS is characterized by stiff muscles, muscle twitching, amyotrophy, and gradually worsening weakness due to muscles decreasing in size resulting in difficulties in walking, speaking, swallowing, and breathing. Respiratory failure is usually the cause of death in patients suffering from ALS. There is no cure yet available for this mortal disease.

The diagnosis of ALS is difficult and requires ruling out other possible causes of symptoms and signs such as muscle weakness, muscle atrophy, impaired swallowing or breathing, cramping, or stiffness of affected muscles, and/or slurred and nasal speech. Besides neurological assessment by medical practitioners, the diagnosis typically involves EMG, measuring nerve conductive velocity or MRI. Laboratory tests including muscle biopsy are also available.

Nevertheless, there is a need for an early and reliable diagnosis of this neurodegenerative disease as well as monitoring of disease progression.

The aforementioned cognition and movement diseases and disorders are prominent examples which shall illustrate the need for an early and reliable diagnosis of the disease or disorder conditions, in particular, in daily life situations as well as for a monitoring of the disease condition and/or progression. However, such a reliable and efficient diagnosis currently requires the presence of a medical practitioner for neurological assessments or application of expensive and time consuming imaging methods in, e.g., hospitals. These drawbacks apply mutatis mutandis for the other cognition and movement diseases and disorders. Therefore, there is a need for less expensive, reliable and effective diagnostic tools and measures which can be carried out in a simple manner during daily life situations by the affected patients.

SUMMARY

The present disclosure relates to a method for assessing a cognition and movement disease or disorder in a subject suspected to suffer therefrom, the method comprising the steps of:
a) determining at least one qualimetric activity parameter for cognition and/or fine motoric activity from a, typically preexisting, dataset of cognition and/or fine motoric activity measurements from said subject using a mobile device; and
b) comparing the determined at least one qualimetric activity parameter to a reference, whereby the cognition and movement disease or disorder will be assessed.

Typically, the method further comprises the step of (c) assessing the cognition and movement disease or disorder in a subject based on the comparison carried out in step (b).

In some embodiments, the method may also comprise, prior to step (a), the step of obtaining from the subject using a mobile device a dataset of activity measurements during predetermined activity performed by the subject. However, typically the method is an ex vivo method carried out on an existing dataset of cognition or fine motoric activity measurements of a subject which does not require any physical interaction with the said subject, i.e., a method of data analysis and evaluation performed on an existing dataset. Typically, the method is a computer-implemented method.

The method according to this disclosure may essentially consist of the aforementioned steps or it may include additional steps.

The method may be carried out on the mobile device by the subject once the dataset of activity measurements has been acquired. Thus, the mobile device acquiring the dataset and the device evaluating the dataset may be physically identical, i.e., the same device. Such a mobile device shall have a data acquisition unit which typically comprises means for data acquisition, i.e., means which detect or measure either quantitatively or qualitatively physical and/or chemical parameters and transform them into electronic signals transmitted to the evaluation unit in the mobile device used for carrying out the method according to the disclosure. The data acquisition unit comprises means for data acquisition, i.e., means which detect or measure either quantitatively or qualitatively physical and/or chemical parameters and transform them into electronic signals transmitted to the device being remote from the mobile device and used for carrying out the method according to the disclosure. Typically, said means for data acquisition comprise at least one sensor. It will be understood that more than one sensor can be used in the mobile device, i.e., at least two, at least three, at least four, at least five, at least six, at least seven, at least eight, at least nine or at least ten or even more different sensors. Typical sensors used for data acquisition are sensors such as gyroscope, magnetometer, accelerometer, proximity sensors, thermometer, humidity sensors, pedometer, heart rate detectors, fingerprint detectors, touch sensors, voice recorders, light sensors, pressure sensors, location data detectors, cameras, time recorders, sweat analysis sensors and the like. The evaluation unit typically comprises a processor and a database as well as software which is tangibly embedded to said device and, when running on said device, carries out the disclosed method. More typically, such a mobile device may also comprise a user interface, such as a screen, which allows for providing the result of the analysis carried out by the evaluation unit to a user.

Alternatively, the method may be carried out on a device being remote with respect to the mobile device that has been used to acquire the said dataset. In this case, the mobile device shall merely comprise means for data acquisition, i.e., means which detect or measure either quantitatively or qualitatively physical and/or chemical parameters and transform them into electronic signals transmitted to the device being remote from the mobile device and used for carrying out the method according to the disclosure. Typically, said means for data acquisition comprise at least one sensor. It will be understood that more than one sensor can be used in the mobile device, i.e., at least two, at least three, at least four, at least five, at least six, at least seven, at least eight, at least nine or at least ten or even more different sensors. Typical sensors used for data acquisition are sensors such as gyroscope, magnetometer, accelerometer, proximity sensors, thermometer, humidity sensors, pedometer, heart rate detectors, fingerprint detectors, touch sensors, voice recorders, light sensors, pressure sensors, location data detectors, cameras, time recorders, sweat analysis sensors and the like. Thus, the mobile device and the device used for carrying out the method may be physically different devices. In this case, the mobile device may communicate with the device used for carrying out the method of the present disclosure by any means for data transmission. Such data transmission may be achieved by a permanent or temporary physical connection, such as coaxial, fiber, fiber-optic, twisted-pair or 10 BASE-T cables. Alternatively, it may be achieved by a temporary or permanent wireless connection using, e.g., radio waves, such as Wi-Fi, LTE, LTE-advanced or Bluetooth. Accordingly, for carrying out the disclosed method, the only requirement is the presence of a dataset of activity measurements obtained from a subject using a mobile device. The said dataset may also be transmitted or stored from the acquiring mobile device on a permanent or temporary memory device which subsequently can be used to transfer the data to the device used for carrying out the method. The remote device which carries out the method in this setup typically comprises a processor and a database as well as software which is tangibly embedded to said device and, when running on said device, carries out the method. More typically, the said device may also comprise a user interface, such as a screen, which allows for providing the results of the analysis carried out by the evaluation unit to a user. Thus, the mobile device and the remote device in this setup form a system for carrying out the method.

The term "assessing" as used herein refers to assessing whether a subject suffers from the cognition and movement disease or disorder, or not, or whether a disease or disorder as referred to herein or individual symptoms thereof worsen or improve over time or based on certain stimulation, or not. Accordingly, assessing as used herein includes identifying progression of the said cognition and movement disease or disorder or one or more symptoms accompanying it, identifying improvement of the said cognition and movement disease or disorder or one or more symptoms accompanying it, monitoring the said cognition and movement disease or disorder or one or more symptoms accompanying it, determining efficacy of a therapy of the said cognition and movement disease or disorder or one or more symptoms accompanying it, and/or diagnosing the said cognition and movement disease or disorder or one or more symptoms accompanying it. As will be understood by those skilled in the art, such an assessment, although preferred to be, may usually not be correct for 100% of subjects. The term, however, requires that a statistically significant portion of subjects can be correctly assessed and, thus, identified as suffering from the cognition and movement disease or disorder. Whether a portion is statistically significant can be determined by the person skilled in the art using various well-known statistical evaluation tools, e.g., determination of confidence intervals, p-value determination, Student's t-test, Mann-Whitney test, etc. Details may be found in Dowdy and Wearden, Statistics for Research, John Wiley & Sons, New York 1983. Typically envisaged confidence intervals are at least 50%, at least 60%, at least 70%, at least 80%, at least 90%, at least 95%. The p-values are, typically, 0.2, 0.1, 0.05. Thus, the method of the present disclosure, typically, aids the assessment of cognition and movement diseases or disorders by providing a means for evaluating a dataset of activity measurements.

The term "the cognition and movement disease or disorder" as used herein relates to diseases that are accompanied by impaired cognition and/or movement disabilities. Typically, these diseases or disorders are caused by impaired function of the central nervous system, the peripheral nervous system or the muscular system. The impairment may involve damage or injury of nervous and/or muscular cells such as damages caused by neurodegenerative diseases such as multiple sclerosis, Alzheimer's disease, Chorea Huntington, Parkinson's disease or others. Typically, the cognition and movement disorder is a disease or disorder of the central and/or peripheral nervous system affecting the pyramidal, extrapyramidal, sensory or cerebellar system, or a neuromuscular disease or is a muscular disease or disorder. More typically, the said disease or disorder is selected from the group consisting of: multiple sclerosis (MS), neuromyelitis optica (NMO) and NMO spectrum disorders, stroke, a cerebellar disorder, cerebellar ataxia, spastic paraplegia, essential tremor, myasthenia and myasthenic syndromes or other forms of neuromuscular disorders, muscular dystrophy, myositis or other muscular disorders, a peripheral neuropathy, cerebral palsy, extrapyramidal syndromes, Parkinson's disease, Huntington's disease, Alzheimer's disease, other forms of dementia, leukodystrophies, autism spectrum disorders, attention-deficit disorders (ADD/ADHD), intellectual disabilities as defined by DSM-5, impairment of cognitive performances and reserve related to aging, Parkinson's disease, Huntington's disease, a polyneuropathy, motor neuron diseases and amyotrophic lateral sclerosis (ALS).

Multiple sclerosis (MS) is a typical cognition and movement disease or disorder according to the present disclosure. There are four standardized subtype definitions of MS which are also encompassed by the term as used in accordance with this disclosure: relapsing-remitting, secondary progressive, primary progressive and progressive relapsing. The term relapsing forms of MS is also used and encompasses relapsing-remitting and secondary progressive MS with superimposed relapses. The relapsing-remitting subtype is characterized by unpredictable relapses followed by periods of months to years of remission with no new signs of clinical disease activity. Deficits suffered during attacks (active status) may either resolve or leave sequelae. This describes the initial course of 85 to 90% of subjects suffering from MS. Secondary progressive MS describes those with initial relapsing-remitting MS, who then begin to have progressive neurological decline between acute attacks without any definite periods of remission. Occasional relapses and minor remissions may appear. The median time between disease onset and conversion from relapsing remitting to secondary progressive MS is about 19 years. The primary progressive subtype describes about 10 to 15% of subjects who never have remission after their initial MS symptoms. It is characterized by progression of disability from onset, with no, or only occasional and minor, remissions and improvements. The age of onset for the primary progressive subtype is later than other subtypes. Progressive relapsing MS describes those subjects who, from onset, have a steady neurological decline but also suffer clear superimposed attacks. It is now accepted that this latter progressive relapsing phenotype is a variant of primary progressive MS (PPMS) and diagnosis of PPMS according to McDonald 2010 criteria includes the progressive relapsing variant.

Symptoms associated with MS include changes in sensation (hypoesthesia and par-aesthesia), muscle weakness, muscle spasms, difficulty in moving, difficulties with co-ordination and balance (ataxia), problems in speech (dysarthria) or swallowing (dysphagia), visual problems (nystagmus, optic neuritis and reduced visual acuity, or diplopia), fatigue, acute or chronic pain, bladder, sexual and bowel difficulties. Cognitive impairment of varying degrees as well as emotional symptoms of depression or unstable mood are also frequent symptoms. The main clinical measure of disability progression and symptom severity is the Expanded Disability Status Scale (EDSS). Further symptoms of MS are well known in the art and are described in the standard text books of medicine and neurology, such as for instance Bradley W G, et al. Neurology in Clinical Practice (5th ed. 2008).

Progressing MS as used herein refers to a condition, where the disease and/or one or more of its symptoms get worse over time. Typically, the progression is accompanied by the appearance of active statuses. The said progression may occur in all subtypes of the disease. However, typically progressing MS shall be determined in accordance with the present disclosure in subjects suffering from relapsing-remitting MS.

However, the method can be applied, in particular, in the context of:
  identifying clinical disease activity (i.e., relapse occurrence),
  disability progression,
  primary progressive MS disease course, as defined by established consensus criteria such as but not exclusively the McDonald Criteria 2010 (Polman 2011, Ann Neurol 69:292-302), and/or the Lublin et al. criteria 2013 (Lublin 2014, Neurology 83: 278-286),
  secondary progressive MS disease course, as defined by established consensus criteria such as but not exclusively the McDonald Criteria 2010 (Polman loc. cit.), and/or the Lublin et al. criteria 2013 (Lublin loc. cit.),
  primary progressive MS, as defined by established consensus criteria such as but not exclusively the McDonald Criteria 2010 (Polman loc. cit.), and/or the Lublin et al. criteria 2013 (Lublin loc. cit.), and/or
  secondary progressive MS, as defined by established consensus criteria such as but not exclusively the McDonald Criteria 2010 (Polman loc. cit.), and/or the Lublin et al. criteria 2013 (Lublin loc. cit.).

Moreover, it is suitable for risk assessments in MS patients and, in particular, for:
  Risk prediction models estimating probabilities of disease activity (i.e., relapse and/or new or enlarging lesions on T2 or Fluid Attenuating Inversion Recovery ("FLAIR") weighted brain or spinal cord MRI, and/or gadolinium-enhancing lesions on brain or spinal cord MRI),
  risk prediction models estimating probabilities of disability progression in patients with a diagnosis of multiple sclerosis (MS), as measured for instance but not exclusively by the Expanded Disability Status Scale neurostatus (EDSS), the Multiple Sclerosis Functional Composite (MSFC), and its components the Timed 25-foot walk test or the 9-hole peg test, and/or
  risk prediction models estimating probabilities of emergence of secondary progressive MS disease course in relapsing-onset MS as defined by established consensus criteria such as, but not exclusively, the McDonald Criteria 2010 (Polman loc. cit.), and/or the Lublin et al. criteria 2013 (Lublin loc. cit.).
  risk prediction models estimating probabilities of emergence of specific MRI signs of primary or secondary progressive MS disease course as defined, for instance, but not exclusively, by the presence of slowly expanding lesions (SELs) on T2 or FLAIR weighted brain or spinal cord MRI, or signs of meningeal inflammation detected on FLAIR-weighted brain or spinal cord MRI after injection of gadolinium-based contrast agents.

Furthermore, the method can be applied in the context of:
  Developing algorithmic solutions using, for instance, machine-learning and pattern recognition techniques to estimate probabilities of disease-modifying treatment (DMT) response or failure as evaluated by the risk of ongoing disease activity (i.e., relapse and/or new or enlarging lesions on T2 or FLAIR weighted brain or spinal cord MRI, and/or gadolinium-enhancing lesions on brain or spinal cord MRI) in patients with a diagnosis of multiple sclerosis (MS) treated with specific DMTs,
  developing algorithmic solutions using, for instance, machine-learning and pattern recognition techniques to estimate probabilities of DMT response or failure as evaluated by the risk of ongoing disability progression in patients with a diagnosis of multiple sclerosis (MS) treated with specific DMTs, as measured, for instance, but not exclusively, by the Expanded Disability Status Scale (EDSS), the Timed 25-foot walk test or the 9-hole peg test, and/or
  developing algorithmic solutions using, for instance, machine-learning and pattern recognition techniques to estimate probabilities of DMT response or failure as evaluated by the risk of worsening in brain MRI measures of neural tissue damage and neurodegeneration such as, but not exclusively, the whole brain volume, brain parenchymal fraction, whole grey matter volume, cortical grey matter volume, volume of specific cortical areas, deep grey matter volume, thalamic volume, corpus callosum surface, white matter volume, third ventricle volume, total brain T2 lesion volume, total brain T1 lesion volume, total brain FLAIR lesion volume in patients with a diagnosis of multiple sclerosis (MS) treated with specific DMTs, algorithmic solutions using, for instance, machine-learning and pattern recognition techniques to estimate probabilities of emergence of secondary progressive MS disease course in relapsing-onset MS as defined by established consensus criteria such as, but not exclusively, the McDonald Criteria 2010 (Polman loc. cit.), and/or the Lublin et al. criteria 2013 (Lublin loc. cit.).

Neuromyelitis optica (NMO, previously known as Devic disease) and neuromyelitis optica spectrum disorders (NMOSD) are inflammatory disorders of the central nervous system characterized by severe, immune-mediated demyelination and axonal damage predominantly targeting the optic nerves and spinal cord. Traditionally considered a variant of multiple sclerosis, NMO is now recognized as a distinct clinical entity based on unique immunologic features. The discovery of a disease-specific serum NMO-IgG antibody that selectively binds aquaporin-4 (AQP4) has led to increased understanding of a diverse spectrum of disorders. NMO and NMOSD are characterized by severe relapsing attacks of optic neuritis and transverse myelitis which, unlike the attacks in multiple sclerosis, commonly spare the brain in the early stages. The spectrum of NMO is traditionally restricted to the optic nerves and the spinal cord. The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

A stroke as referred to herein refers to an impairment of the blood flow in the central nervous system, particularly in the brain. Stroke may be ischemic in nature, caused by obstruction of a blood vessel and consequent lack of blood flow into a brain tissue area or may be hemorrhagic in nature caused by brain injury and subsequent bleeding. Symptoms of stroke depend on the affected brain area and typically may include one or more of the following: one-sided inability to move or to feel, problems understanding or speaking, dizziness, or partial loss of vision. Symptoms of hemorrhagic stroke may also include severe headache. In any event, for the treatment of stroke, the time period between the event and the treatment is crucial, in particular, in order to avoid long-term effects on cognition or other central nervous system functions. In some cases the symptoms of stroke may be rather mild and may not be easy to diagnose without suitable test equipment. The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

A cerebellar disease according to this disclosure encompasses any disease which affects the function of the cerebellum. The cerebellum is involved in motor control and learning. Animals and humans with cerebellar dysfunction show, above all, problems with motor control, on the same side of the body as the damaged part of the cerebellum. They continue to be able to generate motor activity, but it loses precision, producing erratic, uncoordinated, or incorrectly timed movements. Typical manifestations of motoric problems arising from the cerebellum include hypotonia, dysmetria, dysarthria, dysdiadochokinesia, intentional tremor or gait impairments. Typically, the disorders causing the aforementioned disabilities are also called cerebellar ataxias. Other diseases affecting the cerebellum include degenerative disease such as olivopontocerebellar atrophy, Machado-Joseph disease, ataxia telangiectasia, Friedreich's ataxia, Ramsay Hunt syndrome type I, paraneoplastic cerebellar degeneration or prion diseases, or may be congenital malformation or underdevelopment (hypoplasia) of the cerebellar vermis, such as Dandy-Walker syndrome or Joubert syndrome. In addition, cerebellar atrophy may also cause cerebellar diseases and may occur in Huntington's disease, multiple sclerosis, essential tremor, progressive myoclonus epilepsy, Niemann-Pick disease, as a result of exposure to toxins including heavy metals or pharmaceutical or recreational drugs or from an acute deficiency of vitamin B1 (thiamine) as seen in beriberi and in Wernicke-Korsakoff syndrome or from vitamin E deficiency. The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Spastic paraplegia, as used herein, refers to a group of inherited diseases accompanied by progressive stiffness and spasticity in the lower limbs. The diseases may also affect the optic nerve, the retina, cause cataracts, ataxia, epilepsy, cognitive impairment, peripheral neuropathy, and deafness. The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Essential tremor, as used herein, refers to a movement disorder involving tremors of the arms, hands, and fingers. Sometimes, other body parts and the voice may also be affected by tremors. Essential tremor is typically an action tremor (i.e., it occurs if the affected muscle is used) or a postural tremor (i.e., it is present with sustained muscular tone). The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Myasthenia, as used herein, refers to a neuromuscular disease also called myasthenia gravis characterized by frequently occurring muscle weakness and fatigue. The muscle weakness becomes more pronounced during exercise and less pronounced at periods of rest. It is caused by circulating autoantibodies that block nicotinic acetylcholine receptors. These antibodies prevent motor neurons from transmitting signals towards the muscles. There are other forms of myasthenia related neuromuscular disease, such as ocular myasthenia or Lambert-Eaton myasthenia syndrome. Said other forms of neuromuscular disorders are also envisaged by the present disclosure as cognition and movement disorders and diseases. The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Muscular dystrophy, as referred to herein, relates to a weakening of muscles caused by defects or death of muscle cells and tissue. Typically, muscle proteins such as dystrophin may become greatly reduced in muscle dystrophy. Types of muscular dystrophy include, but are not limited to, Becker muscular dystrophy, congenital muscular dystrophy, Duchenne muscular dystrophy, distal muscular dystrophy, Emery-Dreifuss muscular dystrophy, facioscapulohumeral muscular dystrophy, limb-girdle muscular dystrophy, and myotonic muscular dystrophy. Moreover, also encompassed by the present disclosure are forms of myositis or other muscular disorders. The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Peripheral neuropathy, as referred to herein, refers to a disease wherein the proper function of peripheral nerves is impaired. Typically, the nerves envisaged in accordance with the present disclosure are those required for movements or sensation. These neuropathies are also called motor neuropathy or sensory neuropathy. Motor neuropathy may cause impaired balance and coordination or, most typically, muscle weakness. Sensory neuropathy may cause numbness to touch and vibration, or reduced position sense causing poorer coordination and balance, but also reduced sensitivity to temperature change and pain, spontaneous tingling or burning pain, or skin allodynia. Neuropathies may also further be classified as mononeuropathy, wherein essentially a single nerve is affected, and polyneuropathies affecting various nerves in different parts of the body. Different causes for neuropathies have been described involving severe disease, such as diabetes, immune disease, infections, physical injuries, chemotherapy, radiation therapy, cancer, alcoholism, Beriberi, hypothyroidism, porphyria, vitamin B12 deficiencies, or excessive vitamin B6. The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Polyneuropathy is understood as damage or a disorder affecting peripheral nerves in roughly the same areas on both sides of the body. Polyneuropathies may be classified in different ways, such as by cause, by speed of progression, by the parts of the body involved or by part of the nerve cell (axon, myelin sheath, or cell body) that is mainly affected. Polyneuropathy can further be classified as acute polyneuropathy, for example caused by infections, autoimmune reactions, toxins, certain drugs or cancer, and chronic polyneuropathy, for example caused by diabetes mellitus, excessive alcohol consumption or degeneration of nerves. Symptoms of polyneuropathy include weakness, numbness, or burning pain which usually begins in the hands and feet and may progress to the arms, legs and sometimes to other parts of the body (Burns 2011, Neurology 76.7 Supplement 2: S6-S13). A number of different disorders are known to cause polyneuropathy, for example, diabetes and some types of Guillain-Barré syndrome. Diagnosis of polyneuropathy is commonly based on physical examinations and further clinical tests including, for example, electromyography, nerve conduction studies, muscle biopsy or certain antibody tests. The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Cerebral palsy (CP) is a group of permanent movement disorders. CP usually appears in early childhood and is caused by abnormal development or damage to the parts of the brain that control movement, balance, and posture. Symptoms include poor coordination, stiff muscles, weak muscles, tremors, seizures, a decreased ability to think or reason, problems with sensation, vision, hearing, swallowing, and speaking. According to the Centers for Disease Control and Prevention (CDC), CP is the most common movement disorder in children and has a prevalence of about 2.11 per 1,000 live births. The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Extrapyramidal syndromes (EPS) are considered to be drug-induced movement disorders. The term "Extrapyramidal symptoms" is derived from the fact that they are symptoms of disorders in the extrapyramidal system that normally regulates posture and skeletal muscle tone. Symptoms may be acute or tardive and include dystonia (continuous spasms and muscle contractions), akathisia (motor restlessness), parkinsonism (characteristic symptoms such as rigidity), bradykinesia (slowness of movement), tremor, and tardive dyskinesia (irregular, jerky movements. Extrapyramidal syndromes are most commonly caused by antipsychotic or antidepressant drugs such as haloperidol, fluphenazine, duloxetine, sertraline, escitalopram, fluoxetine, and bupropion. The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Alzheimer's disease (AD) is a chronic neurodegenerative disease. The disease course of AD can be divided into four stages, with a progressive pattern of cognitive and functional impairment: Pre-dementia, Early stage, Moderate stage, and Advanced stage.

The pre-dementia stage of the disease has also been termed mild cognitive impairment (MCI) and includes early symptoms of AD such as short-term memory loss and difficulties in planning or solving problems (Waldemar 2007, European Journal of Neurology 14.1: e1-e26; Backman 2004, Journal of internal medicine 256.3: 195-204). In the early stage of AD, symptoms such as problems with language, executive functions, perception (agnosia) and execution of movements (apraxia) become apparent. As the disease progresses, behavioral and neuropsychiatric changes become more prevalent. The moderate phase of AD includes the inability to recall vocabulary, loss of reading and writing skills, impairment of coordination of complex motor sequences resulting for example in an increased risk of falling, urinary incontinence, impairment of long-term memory, illusionary misidentifications and other delusional symptoms. Advanced symptoms of AD include reduction of language to simple phrases or even single words, eventually leading to complete loss of speech, severe reduction in muscle mass and mobility and loss of bodily functions. 4

AD is considered to be the cause of 60% to 70% of cases of dementia. Behavioral and psychological symptoms of dementia are considered to constitute a major clinical component of AD (Robert 2005, European Psychiatry 20.7: 490-496). Although the speed of progression of AD can vary, the average life expectancy following diagnosis of AD is about three to nine years (Todd 2013, International journal of geriatric psychiatry 28.11: 1109-1124).

The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Dementia, as referred to herein, includes a variety of brain diseases that cause a decrease in the ability to think and remember, often accompanied with language and motor skill problems. As mentioned above, the most common type of dementia is Alzheimer's disease. Other types include, for example, vascular dementia, Lewy body dementia, frontotemporal dementia, normal pressure hydrocephalus, Parkinson's disease, syphilis, and Creutzfeldt-Jakob disease. Known risk factors for developing dementia include high blood pressure, smoking, diabetes, and obesity. The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Leukodystrophies are a group of disorders that are characterized by degeneration of the white matter in the brain. Leukodystrophies are thought to be caused by imperfect growth or development of the myelin sheath or by loss of myelin due to inflammation in the central nervous system. The degeneration of white matter can be seen in an MRI and used to diagnose leukodystrophies (Cheon 2002, Radiographics 22.3: 461-476). Symptoms of leukodystrophies are usually dependent on the age of onset, which is predominantly in infancy and early childhood. Symptoms include decreased motor function, muscle rigidity, impairment of sight and hearing, ataxia and mental retardation. Leukodystrophy disorders include, for example, X-linked adrenoleukodystrophy, Krabbe Disease, Metachromatic Leukodystrophy (MLD), Canavan Disease and Alexander Disease. The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Autism spectrum disorder (ASD) characterizes a group of complex neurological and developmental disorders. ASD affects the structure and function of the brain and nervous system. Typical characteristics of ASD include social problems such as difficulty in communicating and interacting with others, repetitive behaviors, limited interests or activities and facial expressions, movements, gestures that do not match what is being said. According to the Centers for Disease Control and Prevention (CDC) around 1 in 68 children has been identified with some form of ASD. The diagnosis of ADS may be difficult and is commonly based on the Diagnostic and Statistical Manual of Mental Disorders (DSM). In the past, Asperger's syndrome and Autistic Disorder were considered to be separate disorders. However, in May 2013, a new version of the Diagnostic and Statistical Manual of Mental Disorders (DSM-5), the common manual from the American Psychiatric Association used to diagnose different mental health conditions, was released. The DSM-5 manual now only includes the range of characteristics and severity within one category, called Autism Spectrum Disorder (ASD), and does not highlight subcategories of a larger disorder anymore (previous subcategories were: Autistic disorder, Asperger syndrome, Childhood disintegrative disorder, Pervasive developmental disorder not otherwise specified). According to DSM-5 guidelines, people whose symptoms were previously diagnosed as Asperger's syndrome or Autistic Disorder are now included as part of the category called Autism Spectrum Disorder (ASD). The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Attention-deficit disorders, also referred to as attention deficit disorder (ADD) or Attention deficit hyperactivity disorder (ADHD), refer to a group of neurodevelopmental disorders.

According to the newest new version of the Diagnostic and Statistical Manual of Mental Disorders (DSM-5), several symptoms must be present before age 12 for the diagnosis of Attention-deficit disorders. Typical symptoms of ADD or ADHD include symptoms of inattention such as difficulty following instructions or organizing tasks, symptoms of hyperactivity or impulsivity such as difficulty remaining seated or awaiting turns (e.g., answering before questions have been completed, interruption of conversations). The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Intellectual disability (intellectual developmental disorder), as a DSM-5 diagnostic term, replaces "mental retardation" used in previous editions of the manuals. In DSM-5, the diagnosis of intellectual disability (intellectual developmental disorder) is revised from the DSM-IV diagnosis of mental retardation (American Psychiatric Association, Diagnostic and statistical manual of mental disorders (DSM-5®), American Psychiatric Pub, 2013.) The revised disorder reflects the manual's move away from a multiaxial approach to evaluating conditions. Intellectual disability as defined by DSM-5 involves impairments of general mental abilities that impact adaptive functioning in three domains, or areas: (1) the conceptual domain includes skills in language, reading, writing, math, reasoning, knowledge, and memory; (2) the social domain refers to empathy, social judgment, interpersonal communication skills, the ability to make and retain friendships, and similar capacities; (3) the practical domain centers on self-management in areas such as personal care, job responsibilities, money management, recreation, and organizing school and work tasks. While intellectual disability does not have a specific age requirement, an individual's symptoms must begin during the developmental period and are diagnosed based on the severity of deficits in adaptive functioning. The disorder is considered chronic and often co-occurs with other mental conditions like depression, attention-deficit/hyperactivity disorder, and autism spectrum disorder. The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Impairment of cognitive performances and reserve related to aging refers to any age-related decline of cognitive performance such as the ability to think and remember and/or any age-related effects on brain size (also referred as "brain reserve") or neural count (also referred to as "cognitive reserve"). Cognitive decline, for example in speeded abilities, executive function, and memory, is believed to typify normal aging (Gunstad 2006, Journal of Geriatric Psychiatry and Neurology 19.2: 59-64). The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Parkinson's disease (PD) is a progressive disorder of the central nervous system that mainly affects the motor system. Typical symptoms include shaking, rigidity, slowness of movement, difficulty with walking. Other symptoms, including sensory, sleep, and emotional problems as well as thinking and behavioral problems, may also occur. Depression and anxiety issues are also commonly observed in the advanced stages of the disease. The cause of Parkinson's disease is currently unknown, but the motor symptoms of the disease are thought to result from the death of cells in the substantia nigra leading to a decrease in dopamine in these areas. However, some of the non-motor symptoms are often present at the time of diagnosis and can precede motor symptoms. Diagnosis of PD is mainly based on the clinical assessment of symptoms combined with other tests such as neuroimaging being used to rule out other diseases. The occurrence of Parkinson's disease is most common in people over the age of 60, affecting males more often than females. The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Huntington's disease (HD), also referred to as Huntington's chorea, is an inherited disorder caused by an autosomal dominant mutation in the Huntingtin gene (HTT). HD is a fatal disease caused by death of brains cells. Symptoms of Huntington's disease can begin at any age from infancy to old age, although they usually become noticeable between the age of 35 and 44 years. Early symptoms include changes in personality, cognition, and physical skills (Walker 2007, The Lancet 369.9557: 218-228). The most characteristic initial physical symptoms are random and uncontrollable movements referred to as chorea. Further symptoms include seizures, abnormal facial expression, difficulties in chewing, swallowing and speaking. Diagnosis of HD is usually based on the clinical assessment of symptoms as well as genetic testing. The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Amyotrophic lateral sclerosis (ALS), the most frequent form of motor neuron disease (MND), is a late-onset fatal neurodegenerative disease affecting motor neurons. ALS occurs with an incidence of about $1/100,000$. Most ALS cases are sporadic, but 5-10% of the cases are familial ALS. Both sporadic and familial ALS (FALS) are associated with degeneration of cortical and spinal motor neurons. Typical symptoms include muscle weakness and atrophy throughout the body and impairment of cognitive functions. The diagnosis of ALS commonly includes a clinical examination and series of diagnostic tests, often ruling out other diseases that mimic ALS. For ALS to be diagnosed, usually symptoms of both upper and lower motor neuron damage that cannot be attributed to other causes must be present. The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

Neuroleptic malignant syndrome (NMS) is a life-threatening neurological disorder most often caused by an adverse reaction to neuroleptic or antipsychotic drugs such as haloperidol, droperidol, promethazine, chlorpromazine, clozapine, olanzapine, risperidone, quetiapine, or ziprasidone. Symptoms include muscle cramps, tremors, fever, symptoms of autonomic nervous system instability such as unstable blood pressure and alterations in mental status (agitation, delirium, or coma). The muscular symptoms in NMS are most likely caused by blockade of the dopamine receptor D2, leading to abnormal function of the basal ganglia, similar to that seen in Parkinson's disease. Moreover, an elevated level of plasma creatine kinase is associated with NMS (Strawn 2007, American Journal of Psychiatry 164.6: 870-876). The method of the present disclosure can also typically be applied mutatis mutandis for those purposes referred to in accordance with MS. In particular, the method may be applied for assessing the disease, including the aspects described elsewhere in detail, making risk assessments, establishing risk prediction models and/or developing algorithmic solutions using, for instance, machine-learning and pattern recognition techniques.

The term "subject" as used herein refers to animals and, typically, to mammals. In particular, the subject is a primate and, most typically, a human. The subject in accordance with the present disclosure suffers from or may be suspected to suffer from a cognition and movement disease or disorder, i.e., the subject may already show some or all of the symptoms associated with the said disease.

The term "qualimetric activity parameter for cognition and/or fine motoric activity" as used herein refers a single or composite measure of intra-performance fluctuations in at least one qualitative feature of cognitive and/or fine motoric functioning and integrity during the completion of specific cognitive and/or motoric tasks. Such qualimetric parameters measure 'how' the nervous system functions or performs during a given task in contrast to performance tests that only measure the capacity to complete a task with a specific overall performance. Accordingly, a qualimetric parameter as referred to herein is, typically, a measure of the quality with which a task can be performed, e.g., it is based on the correctness of performed tasks and the time required to perform a task or a series of iterating tasks. Thus, a qualimetric parameter may be, typically, a time parameter, such as the duration of a task or the time difference between the performances of iterating tasks or a parameter depending on the time, such as the velocity, or it may be a parameter reflecting movement accuracy. Particular cognition and/or fine motoric activities from which qualimetric parameters can be derived in accordance with the present disclosure are listed elsewhere herein in more detail.

The term "at least one" means that one or more parameters, such as qualimetric activity parameters, may be determined in accordance with this disclosure, i.e., at least two, at least three, at least four, at least five, at least six, at least seven, at least eight, at least nine or at least ten or even more different parameters. Thus, there is no upper limit for the number of different parameters which can be determined in accordance with the method of the present disclosure. Typically, however, there will be between one and three different parameters per dataset of activity measurement determined.

The term "dataset of activity measurements" refers, in principle, to the entirety of data acquired by the mobile device from a subject during activity measurements or any subset of said data useful for deriving a qualimetric activity parameter. Details are also found elsewhere herein. In particular, the activity measurements in connection with the term "dataset of cognition and/or fine motoric activity measurements", as used in accordance with the present disclosure, comprise measurements of datasets during performances of an Information Processing Speed (IPS) test, a pinching test performed on a sensor surface of the mobile device and/or from a U-turn test (UTT), a 2-minute walk test (2MWT), a static balance test (SBT) or continuous analysis of gait (CAG) from passive monitoring as described elsewhere herein in detail. Typically, the cognition and/or fine motoric activity measured by these respective tests is attention, information processing speed, visual scanning, and/or hand motoric activity. The dataset is a preexisting dataset which means that the method does typically not require data acquisition from the subject.

In the following, particular envisaged activity tests and means for measuring by a mobile device in accordance with the method are specified.

(1) Cognitive Qualimetric Activity Parameters from a Computer-Implemented Information Processing Speed (IPS) Test The aim of the information processing speed testing is to detect impairment of key neurocognitive functions that underlie an iterative visual substitution task, including sustained attention, visual scanning, and recent memory. Information processing in this instance is composed of different steps, starting with the input of visual information into the sensory system that secondarily extends to the output, i.e., responding by pressing a key on the smartphone touchscreen. The major steps in this process are (1) transmission of afferent visual sensory information, (2) the completion of the cognitive substitution task, and, (3) execution of an efferent motor output (Costa 2017).

The symbol digit modalities test (SDMT, Smith 1968, 1982) or the processing speed test (PST, Rao 2017) do not account for any measurement of the relative weight of the reaction time or motor output time in the overall test performance. The IPS test was developed, in accordance with the present method, to enable specific assessment of the speed of symbol/digit substitution tasks by subtracting from the overall performance the reaction time, visual processing time as well as the motor output time, measured separately.

The symbol set of the IPS test consists of 9 different abstract symbols which follow a simple design scheme and are assigned to nine keys, i.e., digits 1 to 9.

To account for participants' reaction time and the time it takes to produce the efferent motor output, a 15-second digit/digit matching exercise will be done after the symbol/digit substitution task. The digits will be presented in an analogue rotation scheme for the numbers as the symbols in the prior substitution task and will be embedded in the same user interface.

For the symbol/digit substitution task of the IPS test, 120 abstract symbols will be displayed in sequence in a maximum of 90 seconds total. The legend key (round Robin alternation of 3 or more versions) showing the nine symbols with their respective matching digits from 1 to 9 will be displayed alongside for reference. The study participant is asked to provide as many correct responses as possible by typing for each iterative symbol the matching key as fast as possible on a numeric keypad on the smartphone's screen during 90 seconds.

The number of correct responses to the symbol matching and baseline test will be displayed to the patient.

Typical cognitive qualimetric activity parameters can be derived from the Information Processing Speed (IPS) test, which aims at detecting and measuring impairment of key neurocognitive functions that underlie an iterative visual substitution task, including sustained attention, visual scanning, and recent memory. The digit to symbol substitution tasks are known to correlate with brain atrophy in conditions of mild cognitive impairment and the IPS test performed on a mobile device (differently from similar tests such as SDMT (Smith 1968, 1982) or PST (Rao 2017)) enables separate measurement of the cognitive substitution task performance while adjusting for any influence of the visual processing and motor execution time.

Typical cognitive qualimetric activity parameters derived from the IPS test and captured as continuous outcome variables reflecting intra-test fluctuations that measure cognitive integrity are selected from the group consisting of:

1) the elapsed time before (from n-1) a response,
2) the elapsed time before (from n-1) a correct response,
3) the elapsed time before (from n-1) an incorrect response,
4) the elapsed time between (from prior correct response) correct responses,
5) the elapsed time between (from prior incorrect response) incorrect responses, and 6) the parameters (1), (2), and (3) applied to specific symbols or clusters of symbols when the sequence of symbols is modified to evaluate working memory and learning within the task.

It will be understood that one or more of these qualimetric parameters can be determined in accordance with the present disclosure. Typically, one, two, three or all of these parameters are to be determined.

More typically, qualimetric parameters of interest derived from the IPS test are one or more of the following:

1. Number of correct responses
   a. Total number of overall correct responses (CR) in 90 seconds
   b. Number of correct responses from time 0 to 30 seconds ($CR_{0-30}$)
   c. Number of correct responses from time 30 to 60 seconds ($CR_{30-60}$)
   d. Number of correct responses from time 60 to 90 seconds ($CR_{60-90}$)
   e. Number of correct responses from time 0 to 45 seconds ($CR_{0-45}$)
   f. Number of correct responses from time 45 to 90 seconds ($CR_{45-90}$)
   g. Number of correct responses from time i to j seconds ($CR_{i-j}$), where i,j are between 1 and 90 seconds and i<j.
2. Number of errors
   a. Total number of errors (E) in 90 seconds
   b. Number of errors from time 0 to 30 seconds ($E_{0-30}$)
   c. Number of errors from time 30 to 60 seconds ($E_{30-60}$)
   d. Number of errors from time 60 to 90 seconds ($E_{60-90}$)
   e. Number of errors from time 0 to 45 seconds ($E_{0-45}$)
   f. Number of errors from time 45 to 90 seconds ($E_{45-90}$)
   g. Number of errors from time i to j seconds ($E_{i-j}$), where i,j are between 1 and 90 seconds and i<j.
3. Number of responses
   a. Total number of overall responses (R) in 90 seconds
   b. Number of responses from time 0 to 30 seconds ($R_{0-30}$)
   c. Number of responses from time 30 to 60 seconds ($R_{30-60}$)
   d. Number of responses from time 60 to 90 seconds ($R_{60-90}$)
   e. Number of responses from time 0 to 45 seconds ($R_{0-45}$)
   f. Number of responses from time 45 to 90 seconds ($R_{45-90}$)
4. Accuracy rate
   a. Mean accuracy rate (AR) over 90 seconds: AR=CR/R
   b. Mean accuracy rate (AR) from time 0 to 30 seconds: $AR_{0-30} = CR_{0-30}/R_{0-30}$
   c. Mean accuracy rate (AR) from time 30 to 60 seconds: $AR_{30-60} = CR_{30-60}/R_{30-60}$
   d. Mean accuracy rate (AR) from time 60 to 90 seconds: $AR_{60-90} = CR_{60-90}/R_{60-90}$
   e. Mean accuracy rate (AR) from time 0 to 45 seconds: $AR_{0-45} = CR_{0-45}/R_{0-45}$
   f. Mean accuracy rate (AR) from time 45 to 90 seconds: $AR_{45-90} = CR_{45-90}/R_{45-90}$
5. End of task fatigability indices
   a. Speed Fatigability Index (SFI) in last 30 seconds: $SFI_{60-90} = CR_{60-90}/\max(CR_{0-30}, CR_{30-60})$
   b. SFI in last 45 seconds: $SFI_{45-90} = CR_{45-90}/CR_{0-45}$
   c. Accuracy Fatigability Index (AFI) in last 30 seconds: $AFI_{60-90} = AR_{60-90}/\max(AR_{0-30}, AR_{30-60})$
   d. AFI in last 45 seconds: $AFI_{45-90} = AR_{45-90}/AR_{0-45}$
6. Longest sequence of consecutive correct responses
   a. Number of correct responses within the longest sequence of overall consecutive correct responses (CCR) in 90 seconds
   b. Number of correct responses within the longest sequence of consecutive correct responses from time 0 to 30 seconds ($CCR_{0-30}$)
   c. Number of correct responses within the longest sequence of consecutive correct responses from time 30 to 60 seconds ($CCR_{30-60}$)
   d. Number of correct responses within the longest sequence of consecutive correct responses from time 60 to 90 seconds ($CCR_{60-90}$)
   e. Number of correct responses within the longest sequence of consecutive correct responses from time 0 to 45 seconds ($CCR_{0-45}$)
   f. Number of correct responses within the longest sequence of consecutive correct responses from time 45 to 90 seconds ($CCR_{45-90}$)
7. Time gap between responses
   a. Continuous variable analysis of gap (G) time between two successive responses
   b. Maximal gap (GM) time elapsed between two successive responses over 90 seconds
   c. Maximal gap time elapsed between two successive responses from time 0 to 30 seconds ($GM_{0-30}$)
   d. Maximal gap time elapsed between two successive responses from time 30 to 60 seconds ($GM_{30-60}$)
   e. Maximal gap time elapsed between two successive responses from time 60 to 90 seconds ($GM_{60-90}$)
   f. Maximal gap time elapsed between two successive responses from time 0 to 45 seconds ($GM_{0-45}$)
   g. Maximal gap time elapsed between two successive responses from time 45 to 90 seconds ($GM_{45-90}$)
8. Time Gap between correct responses
   a. Continuous variable analysis of gap (Gc) time between two successive correct responses
   b. Maximal gap time elapsed between two successive correct responses (GcM) over 90 seconds
   c. Maximal gap time elapsed between two successive correct responses from time 0 to 30 seconds ($GcM_{0-30}$)
   d. Maximal gap time elapsed between two successive correct responses from time 30 to 60 seconds ($GcM_{30-60}$)
   e. Maximal gap time elapsed between two successive correct responses from time 60 to 90 seconds ($GcM_{60-90}$)
   f. Maximal gap time elapsed between two successive correct responses from time 0 to 45 seconds ($GcM_{0-45}$)
   g. Maximal gap time elapsed between two successive correct responses from time 45 to 90 seconds ($GcM_{45-90}$)
9. Fine finger motor skill function parameters captured during IPS test
   a. Continuous variable analysis of duration of touchscreen contacts (Tts), deviation between touchscreen contacts (Dts) and center of closest target digit key, and mistyped touchscreen contacts (Mts) (i.e., contacts not triggering key hit or triggering key hit but associated with secondary sliding on screen), while typing responses over 90 seconds
   b. Respective variables by epochs from time 0 to 30 seconds: $Tts_{0-30}$, $Dts_{0-30}$, $Mts_{0-30}$
   c. Respective variables by epochs from time 30 to 60 seconds: $Tts_{30-60}$, $Dts_{30-60}$, $MtS_{30-60}$ d. Respective variables by epochs from time 60 to 90 seconds: $Tts_{60-90}$, $Dts_{60-90}$, $MtS_{60-90}$
e. Respective variables by epochs from time 0 to 45 seconds: $Tts_{0-45}$, $Dts_{0-45}$, $Mts_{0-45}$
f. Respective variables by epochs from time 45 to 90 seconds: $Tts_{45-90}$, $Dts_{45-90}$, $Mts_{45-90}$ 10. Symbol-specific analysis of performance by single symbol or cluster of symbols
    a. CR for each of the 9 symbols individually and all their possible clustered combinations
    b. AR for each of the 9 symbols individually and all their possible clustered combinations
    c. Gap time (G) from prior response to recorded responses for each of the 9 symbols individually and all their possible clustered combinations
    d. Pattern analysis to recognize preferential incorrect responses by exploring the type of mistaken substitutions for the 9 symbols individually and the 9 digit responses individually 11. Learning and cognitive reserve analysis
    a. Change from baseline (baseline defined as the mean performance from the first 2 administrations of the test) in CR (overall and symbol-specific as described in (10) between successive administrations of IPS tests
    b. Change from baseline (baseline defined as the mean performance from the first 2 administrations of the test) in AR (overall and symbol-specific as described in (10) between successive administrations of IPS tests
    c. Change from baseline (baseline defined as the mean performance from the first 2 administrations of the test) in mean G and GM (overall and symbol-specific as described in (10) between successive administrations of IPS tests
    d. Change from baseline (baseline defined as the mean performance from the first 2 administrations of the test) in mean Gc and GcM (overall and symbol-specific as described in (10) between successive administrations of IPS tests
    e. Change from baseline (baseline defined as the mean performance from the first 2 administrations of the test) in $SFI_{60-90}$ and $SFI_{45-90}$ between successive administrations of IPS tests
    f. Change from baseline (baseline defined as the mean performance from the first 2 administrations of the test) in $AFI_{60-90}$ and $AFI_{45-90}$ between successive administrations of IPS tests
    g. Change from baseline (baseline defined as the mean performance from the first 2 administrations of the test) in Tts between successive administrations of IPS tests
    h. Change from baseline (baseline defined as the mean performance from the first 2 administrations of the test) in Dts between successive administrations of IPS tests
    i. Change from baseline (baseline defined as the mean performance from the first 2 administrations of the test) in Mts between successive administrations of IPS tests In yet another embodiment, the IPS test shall be applied to determine baseline, cognitive and information processing speed, as well as oculomotor and motor function qualimetric activity parameters. Thereby, a response time for performing a task on the mobile device may be dissected and the contribution of the individual parts of the nervous system involved in the response can be determined. This is particularly advantageous since it has been found that in conventional SDMT, parts or functions of the nervous system which are affected by a disease may be compensated by parts or functions which are not affected. Thereby, false negative diagnoses may occur based on SDMT data. For example, a patient suffering from a disease such as MS may compensate for bad hand motor performance with superior cognitive and information processing speed. When measuring the overall response time for performing an SDMT task, such a patient may not perform worse, or only insignificantly worse, than a healthy subject, although suffering from the disease.

Therefore, in yet another embodiment, the cognitive qualimetric activity parameters to be analyzed may be derived from a computer-implemented IPS test.

In step i) the computer implemented IPS test shall determine the information processing speed by measuring the response time for symbol matching tasks using test symbols which are not familiar (e.g., no naïve numbers or symbols) to the subject who is performing the task. Test symbols which are useful for the IPS test, typically, show little similarity to letters or mathematical notation and should, therefore, also be independent of influences such as cultural background, reading and writing capabilities or educational standards. Such test symbols can, therefore, also be used for children or subjects with low educational attainment (e.g., illiterate people). Moreover, in order to improve visual recognition, the test symbols follow a simple design principle with less detail. More typically, the symbols may be designed as symbol pairs having characteristic features at opposite sides of a mirror axis parallel to the reading direction or orthogonal to it (e.g., left/right, up/down features) or as recognizable singleton symbols with rotational symmetry, directional orientation or characteristic edges. Typical test symbols are described and shown in the accompanying examples below.

The test is performed, typically, by showing the subject on a display the test symbol and a legend which allocates different test symbols shown during the test to naïve numbers or other naïve symbols such as letters. These naïve numbers or other naïve symbols are also present on the keypad such that the subject performing the test can press the key which carries the naïve number or naïve symbol being allocated to the test symbol. It will be understood that the response time in the IPS test for this task depends on the reaction time, the processing time for hand motor output and the time for cognitive information processing.

In the step i) of IPS testing described before, iterations of fixed test symbol matching sequences, wherein each sequence consists of matching tasks for at least 6 different test symbols, can be performed. The test symbol matching sequences may also comprise more than 6 and, typically, 7, 8 or 9 different test symbols.

Typically, the said iterations are followed by a new randomized test symbol matching sequence. An improvement in response time between the first and the last iteration indicates cognitive learning capabilities of the subject or a standard test response time and the response time in a randomized symbol matching sequence run. Typically, at least two, at least three, at least four iterations of test symbol matching sequences are performed and, more typically, three test symbol matching sequences are performed. Moreover, during the iterations, typically, the test symbol matching can be carried out as in standard clinical SDM tests. Typically, the legend for the symbols, the size of the symbols, the keypad and other parameters displayed on the mobile device used for carrying out the IPS test are kept at constant conditions as far as the dimension, appearance, contrast, etc.

are concerned in order to avoid sensory influences which are not related to the information processing speed. Typical examples for the implementation of an automated IPS test are described in the examples further below.

The IPS test in step ii) determines a baseline information processing speed by measuring a baseline response time. In one non-limiting embodiment, said baseline response time can be determined by measuring the time for matching a naïve number or symbol to the matching naïve number or symbol on a keypad of the mobile device. More typically, the naïve number or symbol shall be selected such that the individual which carries out the test can perform the matching without substantial cognitive effort. More typically, numbers from 0 to 9 may be used as naïve numbers. Such a baseline response time using naïve number or symbol matching will be mainly dependent on the reaction time and processing time for hand motor output. Cognitive tasks play only a minor role and do not contribute significantly to the baseline response time. Thereby, the information processing speed determined in the subsequent steps can be de-convoluted by said baseline response time into reaction time and processing time for hand motor output and time for cognitive information processing. It will be understood that the aforementioned step i) can be performed before or after the step ii).

Thus, the difference in response time between a task comprising reaction time, processing time for hand motor output and time for cognitive information processing (e.g., a test matching different non-naïve test symbols to a legend, which assigns said different test symbols to naïve symbols such as naïve numbers or letters, by pressing the respective key on a keypad) and a task comprising reaction time and processing time for hand motor output (a baseline task, e.g., matching a naïve number or symbol to the matching naïve number or symbol on a keypad) is determined as one cognitive qualimetric activity parameter being part of the dataset to be analyzed by the method. Moreover, the IPS test also aims at determining learning capabilities by comparing the response time required for performing a test task at the end of a run of identical test symbol matching sequences to the response time required for performing a randomized symbol matching sequence run.

Thus, in an embodiment of the disclosed method, a computer-implemented method for automatically assessing information processing speed (IPS) is performed in the test subject comprising the steps of:
i) determining at least one first qualimetric activity parameter for sensorial transmission, cognition and motoric output activity and at least one second qualimetric activity parameter for sensorial transmission and motoric output activity in a preexisting dataset of cognition and/or fine motoric activity measurements comprising cognitive oculomotor activity measurements obtained from said test subject;
ii) determining at least one third qualimetric activity parameter for cognition by comparing the first and the second qualimetric activity parameters to each other;
iii) assessing the information processing speed in a subject based on the first, second and third qualimetric activity parameters;
iv) providing the information processing speed as a qualimetric activity parameter for cognition and/or fine motoric activity in step a) of the method.

The term "information processing speed" as used herein refers to a neurological parameter indicating the speed of information processing. Information processing in this instance is composed of different steps, starting with the input of visual information into the sensory system and extending to the output, i.e., responding by pressing a key on the smartphone touchscreen. The major steps in this process are (1) transmission of afferent visual sensory information, i.e., sensorial transmission, (2) the completion of the cognitive substitution task, i.e., the cognitive information processing, and, (3) execution of an efferent motor output, i.e., the hand motor output. Information processing speed may be affected by cognitive impairments associated with neurological diseases or disorders including those mentioned specifically elsewhere herein or may be an indicator for the cognitive capabilities of a subject.

The term "assessing information processing speed" as used herein refers to assessing the information processing speed in a subject as a qualimetric parameter for cognition and/or fine motoric activity. The term includes absolute and relative determinations of the information processing speed. An absolute determination will be, typically, the determination of a parameter indicating the actual speed of information processing in a subject. A relative determination will be, typically, the determination of information processing speed relative to a reference, e.g., relative to a previously determined information processing speed in the test subject or relative to the information processing speed in a reference subject or a group thereof. As referred to herein, information processing speed comprises an assessment of the three major contributors: (1) transmission of afferent visual sensory information, i.e., sensorial transmission; (2) the completion of the cognitive substitution task, i.e., the cognitive information processing; and, (3) execution of an efferent motor output, i.e., the hand motor output, reflected by the at least one first, second and third activity parameters to be determined in accordance with the method.

Typically, the first, second and/or third qualimetric activity parameter is a time parameter, such as the performance time required to complete a task or a time parameter indicating a change in velocity when performing a task, such as improvement in velocity or worsening in velocity.

In an embodiment, thereby, a third qualimetric activity parameter for cognition by can be determined by comparing the first and the second qualimetric activity parameters to each other. The determined activity parameters can be de-convoluted by the baseline response time into a reaction time and a processing time for hand motor output and a time for cognitive information processing. For the deconvolution, any suitable mathematical operation may be used. For example, the third parameter may be provided by subtracting the second qualimetric activity parameter from the first qualimetric activity parameter. It will be understood that first and second parameters of comparable nature shall be use, e.g., a first and second time parameter, a first and second ratio of time parameters or a first and second score parameter, etc.

Thus, in the computer-implemented IPS test run on a mobile device, which is used to acquire the qualimetric activity parameters to be analyzed, the difference in response time between a task comprising reaction time, processing time for hand motor output and time for cognitive information processing (e.g., a test matching different non-naïve test symbols to a legend, which assigns said different test symbols to naïve symbols such as naïve numbers or letters, by pressing the respective key on a keypad) and a task comprising reaction time and processing time for hand motor output (a baseline task, typically, matching a naïve number or symbol to the matching naïve number or symbol on a keypad) is determined as one cognitive qualimetric activity parameter. Moreover, the IPS test also aims at determining learning capabilities by comparing the response time required for performing a test task at the end of an iteration of identical test symbol matching sequences and the response time required for performing a randomized symbol matching sequence run. Typically, this time comparison may also be determined as a qualimetric activity parameter in accordance with the method.

Accordingly, the present disclosure also provides for a method for assessing information processing speed comprising carrying out steps a) to c) for a dataset of oculomotor activity measurements for a first symbol matching task and a symbol matching task after one or more iterations, typically four iterations, of identical symbol matching tasks and determining the difference in information speed processing assessed for the dataset of the first oculomotor activity measurement and the dataset taken after the iterations. The difference in speed is an indicator for the cognitive learning capabilities of the subject. An improvement in speed is an indicator for normal or improved cognitive capabilities while a worsening is an indicator for cognitive impairment.

The term "dataset of oculomotor activity measurements", as used herein, refers to the entirety of data acquired by the mobile device from a subject during cognitive oculomotor activity measurements or any subset of said data useful for deriving a qualimetric activity parameter. Details are also found elsewhere herein. In particular, the activity measurements in connection with the term "dataset of cognitive oculomotor activity measurements", as used in accordance with the present disclosure, comprise measurements of datasets during performances of an Information Processing Speed (IPS) test as described in the accompanying examples, below. The dataset is a preexisting dataset, which means that the method does typically not require data acquisition from the subject.

Importantly, cognitive qualimetric activity parameters, as aforementioned, can be derived from any other cognitive test acquired from a mobile device and comprising single or composite measures of performance fluctuations in at least one qualitative feature of cognitive activity.

(2) Hand/Arm Function Qualimetric Activity Parameters from a Computer-Implemented Test Evaluating Fine Motoric Capabilities (Fine Motoric Assessments), in Particular, Hand/Arm Motor Functions and, in Particular, the Touchscreen-Based "Draw a Shape" and "Pinching" Tests Typical qualimetric parameters for hand/arm function can be derived from the "Draw a Shape" test and the "Pinching" test.

In yet another embodiment, the mobile device is adapted to perform or acquire data from fine motoric assessments and, in particular, hand/arm activity tests. Manual dexterity (hand motor function) characterizes an individual's ability to coordinate movement of the hand and fingers and manipulate objects in a timely manner. Manual dexterity greatly impacts a subject's performance in daily activities, completing work related tasks, and engaging in leisure activities.

Manual dexterity was identified in 2007 as a core construct for inclusion in the National Institutes of Health (NIH) Toolbox for the assessment of neurological and behavioral function, as part of the NIH Blueprint for Neuroscience Research initiative, which developed brief yet comprehensive instruments to measure motor, cognitive, sensory, and emotional function. After reviewing existing measures, experts recommended two candidate measures of manual dexterity: 1) 9-Hole Peg Test (9HPT), and 2) Grooved Pegboard Test (GPT) for potential inclusion in the NIH Toolbox because of their applicability across the life span, psychometric soundness, brevity (completion time for one trial is relatively short), and applicability in diverse settings.

Primarily, the 9HPT was selected because it met the most inclusion criteria and the test was easy to administer in all age groups, especially younger children. The time to administer the 9-hole peg test was brief (<5 min to measure for both hands) as required for inclusion in the NIH Toolbox. Existing literature supported 9HPT as a reliable and valid measure of finger dexterity, and as capable of assessing hand dexterity in various diagnostic groups (i.e., multiple sclerosis, stroke, cerebral palsy, cerebellar impairment, and Parkinson's disease).

Normative data for the 9HPT have been published across the age span including children and elderly adults and since the late 90 s. 9HPT represents the key component of functional upper limb assessment from the Multiple Sclerosis Functional Composite (MSFC) scale.

Moreover, in accordance with the present disclosure, two touchscreen-based application tests were developed, i.e., the so-called "Draw a Shape" and "Pinching" test, which aimed at replicating the characteristics of 9HPT and GPT on a user-friendly mobile device interface for enabling remote self-assessment of hand motor function in neurological disorders. The "Draw a Shape" and "Pinching" tests will evaluate upper limb motor function and manual dexterity (pinching, drawing) and will be sensitive to changes and abnormalities in pyramidal, extrapyramidal, sensory and cerebellar components of the upper limb nervous system but also to neuromuscular and myogenic alteration of upper limb function. The tests are, typically, performed daily but could alternatively be performed at lower (e.g., weekly or bi-weekly) frequency.

The aim of the "Draw a Shape" test is to assess fine finger control and stroke sequencing. The test is considered to cover the following aspects of impaired hand motor function: tremor and spasticity and impaired hand-eye coordination. The patients are instructed to hold the mobile device in the untested hand and draw on a touchscreen of the mobile device 6 pre-written alternating shapes of increasing complexity (linear, rectangular, circular, sinusoidal, and spiral; vide infra) with the second finger of the tested hand "as fast and as accurately as possible" within a maximum time of, for instance, 30 seconds. To draw a shape successfully, the patient's finger has to slide continuously on the touchscreen and connect indicated start and end points passing through all indicated check points and keeping within the boundaries of the writing path as much as possible.

The two linear shapes each have five checkpoints to connect; i.e., four segments. The square shape has nine checkpoints to connect; i.e., eight segments. The circular shape has 14 checkpoints to connect; i.e., 13 segments. The figure eight shape has 13 checkpoints to connect; i.e., 12 segments. The spiral shape has 22 checkpoints to connect; i.e., 21 segments. Completing the six shapes, then, implies successfully drawing a total of 62 segments.

The accuracy of the drawing and the time used to draw the shape will be reported to the patient. In addition the summed length of all drawings made will be reported and depicted with familiar objects (for example: size of a dog, horse, and building).

The test may be alternatingly performed with right and left hand. The user will be instructed on daily alternation. The two linear shapes each have a specific number "a" of checkpoints to connect, i.e., "a-1" segments. The square shape has a specific number "b" of checkpoints to connect, i.e., "b-1" segments. The circular shape has a specific number "c" of checkpoints to connect, i.e., "c-1" segments. The eight-shape has a specific number "d" of checkpoints to connect, i.e., "d-1" segments. The spiral shape has a specific number "e" of checkpoints to connect, "e-1" segments. Completing the 6 shapes then implies successfully drawing a total of "(2a+b+c+d+e−6)" segments.

Based on shape complexity, the linear and square shapes can be associated with a weighting factor (Wf) of 1, circular and sinusoidal shapes a weighting factor of 2, and the spiral shape with a weighting factor of 3. A shape which is successfully completed on the second attempt can be associated with a weighting factor of 0.5. These weighting factors are numerical examples that can be changed in the context of the present disclosure.

Typical Draw a Shape test qualimetric parameters of interest are one or more of the following list:

1. Shape completion performance scores:
   a. Number of successfully completed shapes (0 to 6) ($\Sigma Sh$) per test
   b. Number of shapes successfully completed at first attempt (0 to 6) ($\Sigma Sh_1$)
   c. Number of shapes successfully completed at second attempt (0 to 6) ($\Sigma Sh_2$)
   d. Number of failed/uncompleted shapes on all attempts (0 to 12) ($\Sigma F$)
   e. Shape completion score reflecting the number of successfully completed shapes adjusted with weighting factors for different complexity levels for respective shapes (0 to 10) ($\Sigma[Sh*Wf]$)
   f. Shape completion score reflecting the number of successfully completed shapes adjusted with weighting factors for different complexity levels for respective shapes and accounting for success at first vs. second attempts (0 to 10) ($\Sigma[Sh_1*Wf]+\Sigma[Sh_2*Wf*0.5]$)
   g. Shape completion scores as defined in (1)(e), and (1)(f) may account for speed of test completion by, for example, being multiplied by 30/t, where t would represent the time in seconds to complete the test.
   h. Overall and first attempt completion rate for each 6 individual shapes based on multiple testing within a certain period of time: ($\Sigma Sh_1$)/($\Sigma Sh_1+\Sigma Sh_2+\Sigma F$) and ($\Sigma Sh_1+\Sigma Sh_2$)/($\Sigma Sh_1+\Sigma Sh_2+\Sigma F$).

2. Segment completion and celerity performance scores/measures: (analysis based on best of two attempts [highest number of completed segments] for each shape, if applicable)
   a. Number of successfully completed segments (0 to [2a+b+c+d+e-6]) ($\Sigma Se$) per test
   b. Mean celerity ([C], segments/second) of successfully completed segments: $C=\Sigma Se/t$, where t would represent the time in seconds to complete the test (max 30 seconds)
   c. Segment completion score reflecting the number of successfully completed segments adjusted with weighting factors for different complexity levels for respective shapes ($\Sigma[Se*Wf]$)
   d. Speed-adjusted and weighted segment completion score ($\Sigma[Se*Wf]*30/t$), where t would represent the time in seconds to complete the test.
   e. Shape-specific number of successfully completed segments for linear and square shapes ($\Sigma SeLs$)
   f. Shape-specific number of successfully completed segments for circular and sinusoidal shapes ($\Sigma Secs$)
   g. Shape-specific number of successfully completed segments for spiral shape ($\Sigma Ses$)
   h. Shape-specific mean linear celerity for successfully completed segments performed in linear and square shape testing: $C_L=\Sigma SeLs/t$, where t would represent the cumulative epoch time in seconds elapsed from starting to finishing points of the corresponding successfully completed segments within these specific shapes.
   i. Shape-specific mean circular celerity for successfully completed segments performed in circular and sinusoidal shape testing: $C_C=\Sigma Secs/t$, where t would represent the cumulative epoch time in seconds elapsed from starting to finishing points of the corresponding successfully completed segments within these specific shapes.
   j. Shape-specific mean spiral celerity for successfully completed segments performed in the spiral shape testing: $C_S=\Sigma Ses/t$, where t would represent the cumulative epoch time in seconds elapsed from starting to finishing points of the corresponding successfully completed segments within this specific shape.

3. Drawing precision performance scores/measures: (analysis based on best of two attempts [highest number of completed segments] for each shape, if applicable)
   a. Deviation (Dev) calculated as the sum of overall area under the curve (AUC) measures of integrated surface deviations between the drawn trajectory and the target drawing path from starting to ending checkpoints that were reached for each specific shapes divided by the total cumulative length of the corresponding target path within these shapes (from starting to ending checkpoints that were reached).
   b. Linear deviation ($Dev_L$) calculated as Dev in (3)(a) but specifically from the linear and square shape testing results.
   c. Circular deviation ($Dev_C$) calculated as Dev in (3)(a) but specifically from the circular and sinusoidal shape testing results.
   d. Spiral deviation ($Dev_S$) calculated as Dev in (3)(a) but specifically from the spiral shape testing results.
   e. Shape-specific deviation ($Dev_{1-6}$) calculated as Dev in (3)(a) but from each of the 6 distinct shape testing results separately, only applicable for those shapes where at least 3 segments were successfully completed within the best attempt.
   f. Continuous variable analysis of any other methods of calculating shape-specific or shape-agnostic overall deviation from the target trajectory.

The aim of the Pinching test is to assess fine distal motor manipulation (gripping and grasping) and control by evaluating accuracy of pinch closed finger movement. The test is considered to cover the following aspects of impaired hand motor function: impaired gripping/grasping function, muscle weakness, and impaired hand-eye coordination. The patients are instructed to hold the mobile device in the untested hand and, by touching the screen with two fingers from the same hand (typically, thumb and second or, more typically, thumb and third finger), to squeeze or pinch as many round shapes (e.g., pictures of tomatoes) as they can during 30 seconds. The number of successfully pinched shapes (e.g., tomatoes) will be reported to the patient. In addition, the total number of pinched tomatoes will be reported in familiar, easy to understand symbols (for example, tomato equivalent as ketchup bottles). Impaired fine motor manipulation will affect the performance. The test will be alternatingly performed with right and left hand. The user will be instructed on daily alternation.

Typical hand/arm function qualimetric activity parameters derived from the pinching test and captured as continuous outcome variables reflecting intra-test fluctuations that measure hand/arm function integrity and manual dexterity are selected from the group consisting of:
1) elapsed time between 2 successive pinching attempts, defined as double contact on the touchscreen followed by a pinching attempt,
2) double touching asynchrony, measured as the lag time between first and second fingers touching the screen for all double contacts detected,
3) pinching target precision, measured as the distance from the equidistant point between the starting touch points of the two fingers at double contact to the center of the tomato shape, for all double contacts detected,
4) pinching finger movement asymmetry, measured as the ratio between respective distances slid by the two fingers (shortest/longest) from the double contact starting points until reaching pinch gap, for all double contacts successfully pinching,
5) pinching finger velocity, measured as the speed (mm/sec) of each one and/or both fingers sliding on the screen from time of double contact until reaching pinch gap, for all double contacts successfully pinching,
6) pinching finger asynchrony, measured as the ratio between velocities of respective individual fingers sliding on the screen (slowest/fastest) from the time of double contact until reaching pinch gap, for all double contacts successfully pinching, and
7) the continuous variable analysis of 1) to 6) over time, as well as their analysis by epochs of variable duration.

It will be understood that one or more of these qualimetric parameters can be determined in accordance with the present disclosure. Typically, one, two three or all of these parameters are to be determined.

Typical Pinching test qualimetric parameters of interest are:
1. Number of squeezed shapes
    a. Total number of tomato shapes squeezed in 30 seconds ($\Sigma Sh$)
    b. Total number of tomatoes squeezed at first attempt ($\Sigma Sh_1$) in 30 seconds (a first attempt is detected as the first double contact on screen following a successful squeezing if not the very first attempt of the test)
2. Pinching precision measures:
    a. Pinching success rate ($P_{SR}$), defined as $\Sigma Sh$ divided by the total number of pinching ($\Sigma P$) attempts (measured as the total number of separately detected double finger contacts on screen) within the total duration of the test.
    b. Double touching asynchrony (DTA), measured as the lag time between first and second fingers touching the screen for all double contacts detected.
    c. Pinching target precision ($P_{TP}$), measured as the distance from the equidistant point between the starting touch points of the two fingers at double contact to the center of the tomato shape, for all double contacts detected.
    d. Pinching finger movement asymmetry ($P_{FMA}$), measured as the ratio between the respective distances slid by the two fingers (shortest/longest) from the double contact starting points until reaching pinch gap, for all double contacts successfully pinching.
    e. Pinching finger velocity ($P_{FV}$), measured as the speed (mm/sec) of each one and/or both fingers sliding on the screen from time of double contact until reaching pinch gap, for all double contacts successfully pinching.
    f. Pinching finger asynchrony ($P_{FA}$), measured as the ratio between velocities of respective individual fingers sliding on the screen (slowest/fastest) from the time of double contact until reaching pinch gap, for all double contacts successfully pinching.
    g. Continuous variable analysis of 2a to 2f over time, as well as their analysis by epochs of variable duration (5-15 seconds)
    h. Continuous variable analysis of integrated measures of deviation from target drawn trajectory for all tested shapes (in particular the spiral and square).

(3) Ambulation Qualimetric Parameters from a Sensor-Based (e.g., Accelerometer, Gyroscope, Magnetometer, Global Positioning System (GPS)) and Computer Implemented Test for Measures of Ambulation Performance and Gait and Stride Dynamics, in Particular, the 2-Minute Walking Test (2MWT) and the U-Turn Test (UTT), Static Balance Test (SBT) and Tests for Ambulation Performance, Step/Stride Dynamics, and Upper Limb Motor Function while Walking Using Data Collected from Passive Continuous Analysis of Gait (CAG)

a) Two-Minute Walking Test (2MWT)

The aim of this test is to assess difficulties, fatigability or unusual patterns in long-distance walking by capturing gait features in a 2MWT. Data will be captured from smartphone sensors. A decrease of stride and step length, increase in stride duration, increase in step duration and asymmetry and less periodic strides and steps may be observed in the case of disability progression or emerging relapse (Hobart 2013). The patient will be instructed to "walk as fast and as long as you can for 2 minutes, but walk safely." The 2MWT is a simple test that is required to be performed indoor or outdoor, on even ground in a place where patients can walk straight for as far as ≥200 meters without U-turns. Patients are allowed to wear regular footwear and an assistive device and/or orthotic as needed. The number of steps walked in the course of two minutes will be reported to patient, as well as the total number of steps walked during all 2 Minute Walk Tests performed.

Typical ambulation qualimetric activity parameters derived from the 2MWT and captured as continuous outcome variables reflecting intra-test fluctuations that measure gait and balance integrity are selected from the group consisting of:
1) walking step time duration,
2) walking step velocity (step/second),
3) step asymmetry rate (difference of step duration between one step to the next divided by mean step duration), and
4) the step length and total distance walked through biomechanical modelling, 5) the deceleration index by epoch, 6) the 5) the asymmetry index by epoch.

It will be understood that one or more of these qualimetric parameters can be determined in accordance with the present disclosure. Typically, one, two three or all of these parameters are to be determined.

Further typical 2MWT qualimetric parameters of particular interest are one or more of the following list:
1. Surrogate of walking speed and spasticity:
   a. Total number of steps detected in, e.g., 2 minutes ($\Sigma S$)
   b. Total number of rest stops if any detected in 2 minutes ($\Sigma Rs$)
   c. Continuous variable analysis of walking step time (WsT) duration throughout the 2MWT
   d. Continuous variable analysis of walking step velocity (WsV) throughout the 2MWT (step/second)
   e. Step asymmetry rate throughout the 2MWT (mean difference of step duration between one step to the next divided by mean step duration): $SAR = mean\Delta(WsT_x - WsT_{x+1})/(120/\Sigma S)$
   f. Total number of steps detected for each epoch of 20 seconds ($\Sigma S_{t, t+20}$)
   g. Mean walking step time duration in each epoch of 20 seconds: $WsT_{t, t+20} = 20/\Sigma S_{t, t+20}$
   h. Mean walking step velocity in each epoch of 20 seconds: $WsV_{t, t+20} = \Sigma S_{t, t+20}/20$
   i. Step asymmetry rate in each epoch of 20 seconds: $SAR_{t, t+20} = mean\Delta_{t, t+20}(WsT_x - WsT_{x+1})/(20/\Sigma S_{t, t+20})$
   j. Step length and total distance walked through biomechanical modelling
2. Walking fatigability indices:
   a. Deceleration index: $DI = WsV_{100-120}/\max(WsV_{0-20}, WsV_{20-40}, WsV_{40-60})$
   b. Asymmetry index: $AI = SAR_{100-120}/\min(SAR_{0-20}, SAR_{20-40}, SAR_{40-60})$ b) U-Turn Test (UTT)

The aim of this test is to assess difficulties or unusual patterns in performing U-turns while walking a short distance at comfortable pace. The UTT is required to be performed indoor or outdoor, on even ground where patients are instructed to "walk safely and perform at least five successive U-turns going back and forward between two points a few meters apart." Gait feature data (change in step counts, duration and asymmetry during U-turns, U-turn duration) during this task will be captured from smartphone sensors. Patients are allowed to wear regular footwear and an assistive device and/or orthotic as needed. The speed of turning will be reported to the patient.

Typical ambulation qualimetric activity parameters indicate fluctuations of walking quality in the UTT and continuous analysis of gait from the passive monitoring, the turning speed from UTT, the number of daily turns while walking and the average daily turning speed. Intra-subject day-to-day monitoring of these qualimetric parameters allows for detecting, e.g., a multiple sclerosis relapse. Clear differences in active test U-turn speed measured with the UTT was observed according to the accompanying examples between prior to reporting a relapse and after.

Typical UTT qualimetric parameters of interest are:
1) Mean number of steps needed from start to end of complete U-turn ($\Sigma Su$)
2) Mean time needed from start to end of complete U-turn (Tu)
3) Mean walking step duration: $Tsu = Tu/\Sigma Su$
4) Turn direction (left/right)
5) Turning speed (degrees/sec)

It will be understood that one or more of these qualimetric parameters can be determined in accordance with the present disclosure. Typically, one, two three or all of these parameters are to be determined.

c) Continuous Analysis of Gait (CAG)

Continuous recording of gait feature data (step counts, duration, and asymmetry) captured from smartphone sensors will allow passive monitoring of daily volume and quality of walking dynamics. The radius of the patient's activities will be reported to the patient. This radius will be expressed in standard dimensions as well as in familiar, lay terms (for example, size of a football field). Continuous recording of gait feature data (step counts, duration, and asymmetry, as well as arm swing dynamic while walking) captured from sensors will allow passive monitoring of daily volume and quality of walking dynamics. Activity detection is a prior step to gait detection and analysis and activity analysis. It may be based on different, more or less complex approaches (Rai 2012, Zee: zero-effort crowdsourcing for indoor localization, Proceedings of the 18th annual international conference on Mobile computing and networking, ACM; Alsheikh, M. A., Selim, A., Niyato, D., Doyle, L., Lin, S., & Tan, H.-P 2015, Deep Activity Recognition Models with Triaxial Accelerometers, arXiv preprint arXiv:1511.04664; or Ordoriez, F. J., & Roggen, D. 2016, Deep Convolutional and LSTM Recurrent Neural Networks for Multimodal Wearable Activity Recognition, Sensors, 16(1), 115), which considers windows of one second as active if the standard deviation of the accelerometer signal is above 0.01 g). The test is typically performed daily.

Typical ambulation qualimetric activity parameters derived from the CAG and captured as continuous outcome variables reflecting intra-test fluctuations that measure gait and balance integrity are selected from the group:
1) the frequency distribution of the number of steps detected within each interval of continuous walk,
2) the walking step duration/velocity over time,
3) the step length variations over time derived through biomechanical modelling,
4) the elevation gain over time, and
5) the frequency distribution of the sit/stand transitions and turns.

It will be understood that one or more of these qualimetric parameters can be determined in accordance with the present disclosure. Typically, one, two, three or all of these parameters are to be determined.

Typical further CAG qualimetric parameters of interest are one or more of the following list:
Surrogate of daily walking range and speed:
   a. Total number of steps for each day of active recording ($\Sigma Sd$)
   b. Total cumulative time of detected walking for each day of active recording ($\Sigma T$)
   c. Total number of intervals of continuous walking for each day of active recording ($\Sigma Id$)
   d. Frequency distribution of the number of steps detected within each interval of continuous walking for each day of active recording ($\Delta Si$)
   e. Maximal number of steps in a single interval of continuous walking for each day of active recording (Scmax)
   f. Mean walking step time duration for each day of active recording: $WsT = \Sigma T/\Sigma Sd$
   g. Mean behavioral turning speed per day and in specific walking bouts or various duration
   h. Mean number of behavioral turns detected per day
   i. Mean step power
   j. Number and characteristics of stair climbs per day
   k. Number of bouts and characteristics of jogging time
   l. Number and characteristics of sit/stand transition per day m. Mean walking step velocity for each day of active recording: WsV=ΣSd/ΣT (step/min)
n. Step length and total distance walked per day derived through biomechanical modelling
o. Mean circadian pattern of gait activity features based on all combinations of stair climbs, jogging, walking, turns, sit/stand transition event detection
p. Variables a-o by time of the day d) Static Balance Test (SBT)

The aim of this test is to assess a person's static balance function according to one of the items (i.e., standing unsupported) of the widely used Berg Balance Scale (BBS), which is a 14-item objective measure designed to assess static balance and fall risk in adult populations (Berg 1992). Data will be captured from smartphone sensors. The patients are asked to stand still, unsupported, for 30 seconds with relaxed arms straight alongside the body if possible and with the smartphone kept in the running band in a median, frontal position. Individuals with increased risk of falling and/or impaired static balance function, may demonstrate altered postural control [sway] (Wai 2014). The variations in the balance movement will be reported to the patient in terms of the sway path length and depicted in symbols (for example: solid large rock, small rock). The animated sway path will be shown as an easy to understand representation of balance variation.

Typical ambulation qualimetric activity parameters derived from the SBT and captured as continuous outcome variables reflecting intra-test fluctuations that measure gait and balance integrity are selected from the group consisting of:
1) sway jerkiness: time derivative of acceleration [Mancini 2012],
2) sway path: total length of trajectory, and
3) sway range.

It will be understood that one or more of these qualimetric parameters can be determined in accordance with the present disclosure. Typically, one, two or all of these parameters are to be determined.

Typical further SBT qualimetric parameters of interest are one or more of the following list:
1. Sway jerkiness: time derivative of acceleration (Mancini 2012)
2. Sway path: total length of trajectory
3. Sway range It will be understood that the mobile device to be applied in accordance with the present disclosure may be adapted to perform one or more of the aforementioned activity tests. In particular, it may be adapted to perform at least one, at least two or all of these tests. Typically, combinations of tests may be implemented on the mobile device.

Moreover, in the method of the present disclosure at least one further parameter may be determined from data comprising general information obtained from the mobile device from the subject. General information may be retrieved from the subject in addition to the qualimetric parameters referred to above. This information is typically derived from answering mood scale questions, answering questions on quality of life and disease symptoms, in particular, by performing the 29-Item Multiple Sclerosis Impact Scale (MSIS29) questionnaire and/or the Multiple Sclerosis Symptom Tracker (MSST).

In the following, further particular envisaged activity tests and means for measuring by a mobile device in accordance with the method of the present disclosure are specified:

(4) A Computer-Implemented Test Evaluating Emotional Status and Well-being, in Particular, the Mood Scale Question (MSQ)

In an embodiment, the mobile device is adapted for performing or acquiring data from a Mood Scale Question (MSQ) Questionnaire. Depression in its various forms is a common symptom of MS patients and, if left untreated, it reduces quality of life, makes other symptoms—including fatigue, pain, cognitive changes—feel worse, and may be life-threatening (National MS Society). Therefore in order to assess patients' perceived overall state, they will be asked how they feel through a 5-item questionnaire on the mobile device. The questionnaire is typically performed daily.

Typical MSQ performance parameters of interest:
1. Proportion of days with excellent mood in the last week, month, and year.
2. Proportion of days with ≥good mood in the last week, month, and year.
3. Proportion of days with ≥decent mood in the last week, month, and year.
4. Proportion of days with horrible mood in the last week, month, and year.
5. Frequency distribution of response type by time of the day between 6-8 a.m., 8-10 a.m., 10-12 a.m., 12-14, 14-16, 16-18, 18-20, 20-24, 0-6 a.m. during the last month, and during the last year.

(5) A Computer-Implemented Test Evaluating Quality of Life, in Particular, the 29-Item Multiple Sclerosis Impact Scale (MSIS29)

In one embodiment, the mobile device is adapted for performing or acquiring data from the Multiple Sclerosis Impact Scale (MSIS)-29 test. To assess the impact of MS on the daily life of subjects, they will be asked to complete MSIS-29 (Hobart 2001, Brain 124: 962-73) biweekly on the mobile device, which is a 29-item questionnaire designed to measure the physical (items 1-20) and psychological (items 21-29) impact of MS from the patient's perspective (Hobart 2001, loc. cit.). We will use the second version of MSIS-29 (MSIS-29v2), which has four-point response categories for each item: "not at all," "a little," "moderately," and "extremely". MSIS-29 scores range from 29 to 116. Scores on the physical impact scale can range from 20 to 80 and on the psychological impact scale from 9 to 36, with lower scores indicating little impact of MS and higher scores indicating greater impact. Question items 4 and 5, as well as items 2, 6, and 15 of MSIS-29v2, related to ambulation/lower limb and hand/arm/upper limb physical functions, respectively, will also be subject to separate cluster analysis. The test is performed, typically, bi-weekly.

Typical MSIS-29 performance parameters of interest are:
1. MSIS-29 score (29-116)
2. MSIS-29 Physical Impact Score (20-80)
3. MSIS-29 Psychological Impact Score (9-36)
4. MSIS-29 ambulation/lower limb score (2-10)
5. MSIS-29 hand/arm/upper limb score (3-15)
6. Time-corrected/filtered MSIS-29 scores of 1.-5. based on minimum time needed to comprehend a posed question and provide an answer
7. Certainty weighted MSIS-29 scores of 1.-6. based on the number of changes to a given answer and the difference/variation between the answers provided
8. Fine finger motor skill function parameters captured during MSIS-29 a. Continuous variable analysis of duration of touchscreen contacts (Tts)
b. Continuous variable analysis of deviation between touchscreen contacts (Dts) and center of closest target digit key
c. Number of mistyped touchscreen contacts (Mts) (sum of contacts not triggering key hit or triggering key hit but associated with secondary sliding on screen) while typing responses.
9. Ratio of 8a, 8b, and 8c variables during versus corresponding variables of eSDMT (transformation/normalization of 8c to represent the projected number of Mts if MSIS-29 per 90 seconds)

(6) A Computer-Implemented Test Tracking Emerging New or Worsening Disease Symptoms, in Particular, the Multiple Sclerosis Symptom Tracker (MSST)

In yet another embodiment, the mobile device is adapted for performing or acquiring data from the Multiple Sclerosis Symptom Tracker (MSST). As the patient's perception of relapse occurrence and symptom variations may differ from clinically relevant symptom aggravation considered as a relapse, simple questions geared towards detecting new or worsening symptoms will be asked directly to the patients bi-weekly on the smartphone and synchronized with the MSIS-29 questionnaire. The patient has, in addition, the option to report symptoms and their respective calendar date of onset at any time. The MSST may, typically, be performed bi-weekly or on demand.

Typical MSST performance parameters of interest:
1. Number of reported episodes of "new or significantly worsening symptoms during the last two weeks" within the last month, and year (as per symptom onset date).
2. Proportion of total reported episodes of "new or significantly worsening symptoms during the last two weeks" that were considered to be "relapse(s)" vs. "not a relapse" vs. "unsure" within the last year.

(7) A Computer-Implemented Passive Monitoring of all or a Predetermined Subset of Activities of a Subject Performed During a Certain Time Window In yet another embodiment, the mobile device is adapted for performing or acquiring data from passive monitoring of all or a subset of activities. In particular, the passive monitoring may encompass monitoring one or more activities performed during a predefined window, such as one or more days or one or more weeks, selected from the group consisting of: measurements of gait, the amount of movement in daily routines in general, the types of movement in daily routines, general mobility in daily living and changes in moving behavior.

Typical passive monitoring performance parameters of interest are:
1. frequency and/or velocity of walking;
2. amount, ability and/or velocity to stand up/sit down, stand still and balance;
3. number of visited locations as an indicator of general mobility;
4. types of locations visited as an indicator of moving behavior.

It will be understood that the mobile device to be applied in accordance with the present disclosure may be adapted to perform one or more of the aforementioned further tests. In particular, it may be adapted to perform at least one, at least two, or all of these tests.

Moreover, the mobile device may be adapted to perform further cognition and movement disorder and disease tests such as computer-implemented versions of other cognitive tests and/or visual contrast acuity tests (such as low contrast letter acuity or Ishihara test; Ishihara test (see, e.g., Bove 2015).

Further data may be processed in the method of the present disclosure as well. These further data are typically suitable for further strengthening the identification of progressing MS in a subject. Typically, such data may be parameters from biochemical biomarkers for MS or data from imaging methods, such as cross-sectional and/or longitudinal Magnetic Resonance Imaging (MRI) measures of whole brain volume, brain parenchymal fraction, whole grey matter volume, cortical grey matter volume, volume of specific cortical areas, deep grey matter volume, thalamic volume, corpus callosum surface or thickness, white matter volume, third ventricle volume, total brain T2-weighted hyperintense lesion volume, total cortical lesion volume, total brain T1-weighted hypointense lesion volume, total brain FLAIR (Fluid Attenuation Inversion Recovery) lesion volume, total new and/or enlarging T2 and FLAIR lesion number and volume, as assessed using automated algorithmic solution software, such as, but not exclusively, MSmetrix™, or NeuroQuant™.

The term "mobile device" as used herein refers to any portable device which comprises a sensor and data-recording equipment suitable for obtaining the dataset of activity measurements. Typically, the mobile device comprises a sensor for measuring the activity. This may also require a data processor and storage unit as well as a display for electronically simulating an activity test on the mobile device. Moreover, from the activity of the subject, data shall be recorded and compiled to a dataset which is to be evaluated by the disclosed method either on the mobile device itself or on a second device. Depending on the specific setup envisaged, it may be necessary that the mobile device comprises data transmission equipment in order to transfer the acquired dataset from the mobile device to one or more further devices. Particularly well-suited as mobile devices according to the present disclosure are smartphones, smartwatches, wearable sensors, portable multimedia devices or tablet computers. Alternatively, portable sensors with data recording and, optionally, processing equipment may be used. Further, depending on the kind of activity test to be performed, the mobile device shall be adapted to display instructions for the subject regarding the activity to be carried out for the test. Particular envisaged activities to be carried out by the subject are described elsewhere herein and encompass the following tests: an Information Processing Speed (IPS) test, a pinching test performed on a sensor surface of the mobile device and/or a U-turn test (UTT), a 2-minute walk test (2MWT), a static balance test (SBT) or continuous analysis of gait (CAG) from passive monitoring, as well as other tests described in this specification.

At least one parameter and, in particular, a qualimetric parameter as referred to herein, can be determined by deriving a desired measured value from the dataset as the said parameter directly. Alternatively, the parameter may integrate one or more measured values from the dataset and, thus, may be a derived from the dataset by mathematical operations. Typically, the parameter is derived from the dataset by an automated algorithm, e.g., by a computer program which automatically derives the said parameter from the dataset of activity measurements when tangibly embedded on a data processing device fed by the said dataset.

The term "reference" as used herein refers to a discriminator which allows the identification of a subject with a cognition and movement disease or disorder. Such a discriminator may be a value for the parameter which indicates that subjects have cognition and movement disorders or diseases.

Such a value may be derived from one or more parameters, in particular, a qualimetric parameter as referred to herein, of subjects known to suffer from the cognition and movement disease or disorder to be investigated. Typically, the average or median may be used as a discriminator in such a case. If the determined parameter from the subject is identical to the reference or above a threshold derived from the reference, the subject can be identified as suffering from cognition and movement disease or disorder in such a case. If the determined parameter differs from the reference and, in particular, is below the said threshold, the subject shall be identified as not suffering from the cognition and movement disease or disorder, respectively.

Similarly, a value may be derived from one or more parameters, in particular, a qualimetric parameter as referred to herein, of subjects known not to suffer from a cognition and movement disease or disorder to be investigated. Typically, the average or median may be used as a discriminator in such a case. If the determined parameter from the subject is identical to the reference or below a threshold derived from the reference, the subject can be identified as not suffering from a cognition and movement disease or disorder in such a case. If the determined parameter differs from the reference and, in particular, is above the said threshold, the subject shall be identified as suffering from the cognition and movement disease or disorder.

As an alternative, the reference may be a previously determined parameter, in particular, a qualimetric parameter as referred to herein, from a dataset of activity measurements which has been obtained from the same subject prior to the actual dataset. In such a case, a determined parameter, determined from the actual dataset, which differs with respect to the previously determined parameter shall be indicative of either an improvement or worsening depending on the previous status of the disease and the kind of activity represented by the parameter. The skilled person knows, based on the kind of activity and previous parameter, how the said parameter can be used as a reference.

Comparing the determined at least one parameter, in particular, a qualimetric parameter as referred to herein, to a reference can be achieved by an automated comparison algorithm implemented on a data processing device, such as a computer. The values of a determined parameter and a reference for said determined parameter, as specified elsewhere herein in detail, are compared to each other. As a result of the comparison, it can be assessed whether the determined parameter is identical, differs from or is in a certain relation to the reference (e.g., is larger or lower than the reference). Based on said assessment, the subject can be identified as suffering from a cognition and movement disease or disorder ("rule-in"), or not ("rule-out"). For the assessment, the kind of reference will be taken into account as described elsewhere in connection with suitable references according to the disclosed method.

Moreover, by determining the degree of difference between a determined parameter and a reference, a quantitative assessment of a cognition and movement disease or disorder in a subject shall be possible. It is to be understood that an improvement, worsening or unchanged overall disease condition or of symptoms thereof can be determined by comparing an actually determined parameter to an earlier determined one used as a reference. Based on quantitative differences in the value of the said performance parameter, the improvement, worsening or unchanged condition can be determined and, optionally, also quantified. If other references, such as references from subjects suffering from the cognition and movement disease or disorder to be investigated are used, it will be understood that the quantitative differences are meaningful if a certain disease stage can be allocated to the reference collective. Relative to this disease stage, worsening, improvement or unchanged disease condition can be determined in such a case and, optionally, also quantified.

The said diagnosis, i.e., the identification of the subject as suffering from a cognition and movement disease or disorder, or not, is indicated to the subject or other person, such as a medical practitioner. Typically, this is achieved by displaying the assessment on a display of the mobile device or the evaluation device. Alternatively, a recommendation for a therapy, such as a drug treatment, or for a certain lifestyle, e.g., a certain nutritional diet or rehabilitation measures, is provided automatically to the subject or other person. To this end, the established diagnosis is compared to recommendations allocated to different diagnoses or assessments in a database. Once the established assessment matches one of the stored and allocated diagnoses or assessments, a suitable recommendation can be identified due to the allocation of the recommendation to the stored diagnoses or assessments matching the established diagnosis or assessment. Accordingly, it is, typically, envisaged that the recommendations and diagnoses are present in form of a relational database. However, other arrangements that allow for the identification of suitable recommendations are also possible and known to the skilled artisan.

Moreover, the one or more parameters may also be stored on the mobile device or indicated to the subject, typically, in real time. The stored parameters may be assembled into a time course or similar evaluation measures. Such evaluated parameters may be provided to the subject as feedback for activity capabilities investigated in accordance with the disclosed method. Typically, such a feedback can be provided in electronic format on a suitable display of the mobile device and can be linked to a recommendation for a therapy as specified above or rehabilitation measures.

Further, the evaluated parameters may also be provided to medical practitioners in doctors' offices or hospitals, as well as to other health care providers, such as developers of diagnostic tests or drug developers in the context of clinical trials, health insurance providers or other stakeholders of the public or private health care system.

Typically, the method of the present disclosure for assessing a subject suffering from a cognition and movement disease or disorder may be carried out as follows:

First, at least one qualimetric parameter of cognition and/or fine motoric activity is determined from an existing dataset of activity measurements obtained from said subject using a mobile device. Said dataset may be transmitted from the mobile device to an evaluating device, such as a computer, or may be processed in the mobile device in order to derive the said at least one parameter from the dataset.

Second, the determined at least one qualimetric parameter of cognition and/or fine motoric activity is compared to a reference by, e.g., using a computer-implemented comparison algorithm carried out by the data processor of the mobile device or by the evaluating device, e.g., the computer. The result of the comparison is assessed with respect to the reference used in the comparison and, based on the said assessment, the subject will be assessed with respect to the cognition and movement disease or disorder.

Third, the said assessment, e.g., the identification of the subject as being a subject suffering from cognition and movement disease or disorder, or not, is indicated to the subject or other person, such as a medical practitioner.

Alternatively, a recommendation for a therapy, such as a drug treatment, or for a certain lifestyle, e.g., a certain nutritional diet, is provided automatically to the subject or other person. To this end, the established assessment is compared to recommendations allocated to different assessments in a database. Once the established assessment matches one of the stored and allocated assessments, a suitable recommendation can be identified due to the allocation of the recommendation to the stored assessment matching the established assessment. Typical recommendations involve therapeutic measures as described elsewhere herein.

As yet another alternative or in addition, the at least one parameter underlying the assessment will be stored on the mobile device. Typically, it shall be evaluated together with other stored parameters by suitable evaluation tools, such as time course assembling algorithms, implemented on the mobile device which can assist with electronically identifying rehabilitation or therapy recommendation as specified elsewhere herein.

The disclosure, in light of the above, also specifically contemplates a method of assessing a cognition and movement disease or disorder in a subject comprising the steps of:
a) obtaining from said subject using a mobile device a dataset of cognition and/or fine motoric activity measurements during predetermined activity performed by the subject;
b) determining at least one qualimetric parameter of cognition and/or fine motoric activity determined from said dataset of activity measurements obtained from said subject using a mobile device;
c) comparing the determined at least one qualimetric parameter of cognition and/or fine motoric activity to a reference; and
d) assessing the cognition and movement disease or disorder in a subject based on the comparison carried out in step (c).

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it should be understood that all terms used throughout this disclosure and claims, regardless of whether said terms are preceded by the phrases "one or more", "at least one", or the like, should not receive a singular interpretation unless it is made explicit herein. That is, all terms used in this disclosure and claims should generally be interpreted to mean "one or more" or "at least one." For example, the term "qualimetric activity parameter" shall be interpreted as "one or more qualimetric activity parameters".

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "particularly," "more particularly," "specifically," "more specifically," "typically," and "more typically" or similar terms are used in conjunction with additional/alternative features, without restricting alternative possibilities. Thus, features introduced by these terms are additional/alternative features and are not intended to restrict the scope of the claims in any way. The disclosure may, as the skilled person will recognize, be performed by using alternative features. Similarly, features introduced by "in an embodiment of the disclosure" or similar expressions are intended to be additional/alternative features, without any restriction regarding alternative embodiments, without any restrictions regarding the scope of the disclosure and without any restriction regarding the possibility of combining the features introduced in such way with other additional/alternative or non-additional/alternative features.

Advantageously, it has been found in the studies underlying the present disclosure that qualimetric parameters of fine motoric activity, optionally together with other performance parameters of motoric and cognitive capabilities, obtained from datasets measured during certain activities of patients suspected to be or suffering from a cognition and movement disease or disorder can be used as digital biomarkers for assessing, e.g., identifying or monitoring, those patients. In particular, it was shown in the studies underlying the present disclosure that the qualimetric parameters used as biomarkers are superior compared to other (conventional) cognition or fine motoric activity parameters since they do not merely serve as a measure for the capability of performing a certain task but rather reflect how a system, e.g., the nervous system and/or motoric system, performs overall by measuring the fluctuations in the performance of a series of tasks. Accordingly, the results obtained are more robust and reliable than those being dependent on individual activity parameters. In the studies underlying the present disclosure, it was advantageously found, in particular, that a hand/arm function qualimetric activity parameter measuring fluctuations of manual dexterity in the pinching task performance during the Pinching test, (see FIG. 3, interim analysis of clinical trial NCT02952911) is more capable of detecting abnormal function than the corresponding in-clinic performance test, i.e., the 9-hole peg test (9HPT). In fact, when assessing NCT02952911 study patients with MS who had presumably normal hand/arm function according to 9HPT, the qualimetric parameters of the Pinching test were able to discriminate patients with MS from healthy controls (see FIG. 3). As a further example, it was found that, advantageously, ambulation qualimetric activity parameters measuring fluctuations of walking quality (turning speed) in the daily UTT (see FIG. 4, interim analysis of clinical trial NCT02952911) can identify worsening acute disability suggestive of MS disease progression and/or activity that in-clinic performance tests did not detect or could not accurately date in time of onset. Clear differences in active test U-turn speed measured with the 5UTT was observed in this example between prior to reporting a potential 'relapse' through the symptom tracker and after (see FIG. 4, panel b). Turning behavior in passive continuous analysis of gait (CAG), another ambulation qualimetric parameter, was also different before versus after 'relapse' onset/reporting for the number of daily turns (see FIG. 4, panel c).

The said datasets investigated by the disclosed method may have been acquired from the patients in a convenient manner by using mobile devices, such as the omnipresent smart phones, portable multimedia devices or tablet computers. The evaluation of the datasets in accordance with the method can be carried out on the same mobile device or it can be carried out on a separate remote device. Moreover, by using such mobile devices, recommendations on lifestyle or therapy can be provided to the patients directly, i.e., without the consultation of a medical practitioner in a doctor's office or hospital. Using the method of the present disclosure, the life conditions of patients can be adjusted more precisely to the actual disease status due to the use of actual determined parameters by the method of the disclosure. Thereby, drug treatments can be selected that are more efficient or dosage regimens can be adapted to the current status of the patient. It is to be understood that the method of the disclosure is, typically, a data evaluation method which requires an existing dataset of cognition or fine motoric activity measurements from a subject. Within this dataset, the method determines at least one cognition or fine motoric activity parameter which can be used for assessing a cognition and movement disease or disorder, i.e., which can be used as a digital biomarker for said disease or disorder.

Accordingly, the method of the present disclosure may be used for:
  assessing the disease condition;
  monitoring patients, in particular, in a real life, daily situation and on large scale;
  supporting patients with lifestyle and/or therapy recommendations;
  investigating drug efficacy, e.g., also during clinical trials;
  facilitating and/or aiding therapeutic decision making;
  supporting hospital management;
  supporting rehabilitation measure management;
  supporting health insurance assessments and management; and/or
  supporting decisions in public health management;
  identification/assessment of subclinical, subtle changes in information processing speed;
  assessing disease modifying therapies and treatments (DTMs); and/or
  assessing cognitive capabilities in general The explanations and definitions for the terms made above apply mutatis mutandis to the embodiments described herein below.

In the following, particular embodiments of the method of the present disclosure are described:

In an embodiment of the method of the present disclosure, said cognition and movement disease or disorder is a disease or disorder of the central and/or peripheral nervous system affecting the pyramidal, extrapyramidal, sensory or cerebellar system, or a neuromuscular disease or is a muscular disease or disorder.

In yet another embodiment, said cognition and movement disease or disorder is selected from the group consisting of: multiple sclerosis, stroke, a cerebellar disorder, cerebellar ataxia, spastic paraplegia, essential tremor, myasthenia or other forms of neuromuscular disorders, muscular dystrophy, myositis or other muscular disorders, a peripheral neuropathy, cerebral palsy, extrapyramidal syndromes, Alzheimer's disease, other forms of dementia, leukodystrophies, autism spectrum disorders, attention-deficit disorders (ADD/ADHD), intellectual disabilities as defined by DSM-5, impairment of cognitive performance and reserve related to aging, Parkinson's disease, Huntington's disease, a polyneuropathy, and amyotrophic lateral sclerosis.

In particular, it has been found that the subjects suffering from NMO and NMOSD, cerebellar ataxia, spastic paraplegia, essential tremor, myasthenia or other forms of neuromuscular disorders, muscular dystrophy, myositis or other muscular disorders, or a peripheral neuropathy may be identified efficiently by using fine motoric activity datasets obtained from the draw a shape and/or squeeze a shape tests. Subjects suffering from cerebral palsy, extrapyramidal syndromes, Alzheimer's disease, other forms of dementia, leukodystrophies, autism spectrum disorders, attention-deficit disorders (ADD/ADHD), intellectual disabilities as defined by DSM-5, impairment of cognitive performances and reserve related to aging may be identified efficiently from fine motoric activity datasets obtained from the eSDMT test. The remaining disease or disorders may be identified by fine motoric activity datasets from any tests or from the combination of all tests efficiently. Accordingly, depending on the cognition and movement disease or disorder to be investigated, the mobile device may be individually configured for obtaining datasets from a suitable combination of tests.

In another embodiment of the method, the at least one qualimetric activity parameter is a cognitive qualimetric activity parameter indicative for fluctuations in neurocognitive functions, a hand/arm function qualimetric activity parameter indicative of fluctuations in manual dexterity or an ambulation qualimetric activity parameter indicative of movement fluctuations.

In another embodiment of the method of the present disclosure, the cognition and/or fine motoric activity measurements comprise data from an Information Processing Speed (IPS) test, a pinching test performed on a sensor surface of the mobile device and/or from a U-turn test (UTT), a 2-minute walk test (2MWT), a static balance test (SBT) or continuous analysis of gait (CAG) from passive monitoring.

In another embodiment, said dataset of cognition activity measurements comprises data from an Information Processing Speed (IPS) test on a sensor surface of the mobile device.

In yet another embodiment, in addition, at least one performance parameter from a dataset of activity measurements is determined to be indicative of the subject's other motoric capabilities and function, walking, color vision, attention, dexterity and/or cognitive capabilities, quality of life, fatigue, mental state, mood, vision and/or cognition.

In a further embodiment of the method, in addition, at least one performance parameter from a dataset of activity measurements is selected from the group consisting of: visual contrast acuity tests (such as low contrast letter acuity or Ishihara test), and Mood Scale Question (MSQ), MISI-29.

In an embodiment of the method of the present disclosure, said mobile device has been adapted to carry out one or more of the tests referred to above for cognition and/or fine motoric activity measurements and, preferably, all of these tests.

In yet another embodiment, said mobile device is comprised in a smartphone, smartwatch, wearable sensor, portable multimedia device or tablet computer.

In a further embodiment of the method, said reference is at least one qualimetric activity parameter for cognition and/or fine motoric activity derived from a dataset of cognition and/or fine motoric activity measurements obtained from the said subject at a time point prior to the time point when the dataset of cognition and/or fine motoric activity measurements referred to in step a) has been obtained from the subject. Typically, a worsening between the determined at least one qualimetric activity parameter and the reference is indicative of a subject that suffers from the cognition and movement disease or disorder.

In another embodiment of the method, said reference is at least one qualimetric activity parameter for cognition and/or fine motoric activity derived from a dataset of cognition and/or fine motoric activity measurements obtained from a subject or group of subjects known to suffer from the cognition and movement disease or disorder. Typically, a determined at least one qualimetric activity parameter being essentially identical compared to the reference is indicative of a subject that suffers from the cognition and movement disease or disorder.

In a further embodiment of the method, said reference is at least one qualimetric activity parameter for cognition and/or fine motoric activity derived from a dataset of cognition and/or fine motoric activity measurements obtained from a subject or group of subjects known not to suffer from the cognition and movement disease or disorder. Typically, a determined qualimetric activity parameter being worsened compared to the reference is indicative of a subject that suffers from the cognition and movement disease or disorder.

The present disclosure also contemplates a computer program, computer program product or computer readable storage medium having tangibly embedded said computer program, wherein the computer program comprises instructions that, when run on a data processing device or computer, carry out the method of the present disclosure as specified above. Specifically, the present disclosure further encompasses:

a computer or computer network comprising at least one processor, wherein the processor is adapted to perform the method according to one of the described embodiments, a computer loadable data structure that is adapted to perform the method according to one of the embodiments described herein while the data structure is being executed on a computer, a computer script, wherein the computer program is adapted to perform the method according to one of the embodiments described in this description while the program is being executed on a computer, a computer program comprising program means for performing the method according to one of the described embodiments while the computer program is being executed on a computer or on a computer network, a computer program comprising program means according to the preceding embodiment, wherein the program means are stored on a storage medium readable to a computer, a storage medium, wherein a data structure is stored on the storage medium and wherein the data structure is adapted to perform the method according to one of the embodiments described herein after having been loaded into a main and/or working storage of a computer or of a computer network, a computer program product having program code, wherein the program code can be stored or are stored on a storage medium, for performing the method according to one of the embodiments described in this description, if the program code are executed on a computer or on a computer network, a data stream signal, typically encrypted, comprising a dataset of cognition or fine motoric activity measurements obtained from the subject using a mobile device, and a data stream signal, typically encrypted, comprising the at least one qualimetric parameter of cognition or fine motoric activity derived from the dataset of cognition or fine motoric activity measurements obtained from the subject using a mobile device.

The present disclosure, further, relates to a method for determining at least one qualimetric parameter of cognition or fine motoric activity from a dataset of cognition or fine motoric activity measurements obtained from said subject using a mobile device a) deriving at least one qualimetric parameter of cognition or fine motoric activity from a, typically, preexisting dataset of cognition or fine motoric activity measurements obtained from said subject using a mobile device; and b) comparing the determined at least one qualimetric parameter to a reference, wherein, typically, said qualimetric parameter of cognition or fine motoric activity can aid in assessing a cognition and movement disease or disorder in said subject.

The present disclosure also relates to a method for recommending a therapy for a cognition and movement disease or disorder comprising the steps of the aforementioned method (i.e., the method for identifying a subject as suffering from a cognition and movement disease or disorder) and the further step of recommending the therapy if the cognition and movement disease or disorder is assessed.

The term "a therapy for a cognition and movement disease or disorder" as used herein refers to all kinds of medical treatments, including drug-based therapies, surgeries, psychotherapy, physical therapy and the like. The term also encompasses, lifestyle recommendations, rehabilitation measures, and recommendations of nutritional diets. Typically, the method encompasses recommendation of a drug-based therapy and, in particular, a therapy with a drug known to be useful for the treatment of the cognition and movement disease or disorder. Such drugs may be a therapy with one or more drugs selected from the group consisting of: interferon beta-1a, interferon beta-1b, glatiramer acetate, mitoxantrone, natalizumab, fingolimod, teriflunomide, dimethyl fumarate, alemtuzumab, daclizumab, thrombolytic agents, such as recombinant tissue plasmin activator, acetylcholinesterase inhibitors, such as tacrine, rivastigmine, galantamine or donepezil, NMDA receptor antagonists, such as memantine, non-steroidal anti-inflammatory drugs, dopa carboxylase inhibitors, such as levodopa, tolcapone or entacapone, dopamine antagonists, such as bromocriptine, pergolide, pramipexole, ropinirole, piribedil, cabergoline, apomorphine or lisuride, MAO-B inhibitors, such as safinamide, selegiline or rasagiline, amantadine, anticholinergics, tetrabenazine, neuroleptics, benzodiazepines, and riluzole. Moreover, the aforementioned method may comprise in yet another embodiment the additional step of applying the recommended therapy to the subject.

Moreover, encompassed in accordance with the present disclosure is a method for determining efficacy of a therapy against a cognition and movement disease or disorder comprising the steps of the aforementioned method (i.e., the method for identifying a subject as suffering from a cognition and movement disease or disorder). The method for determining efficacy comprises the further step of determining a therapy response is effective if improvement of the cognition and movement disease or disorder occurs in the subject upon therapy or determining it is a failure of response if worsening of the cognition and movement disease or disorder occurs in the subject upon therapy, or if the cognition and movement disease or disorder remains unchanged.

The term "improvement" as referred to in accordance with the present disclosure relates to any improvement of the overall disease or disorder condition or of individual symptoms thereof. Likewise, a "worsening" means any worsening of the overall disease or disorder condition or individual symptoms thereof. Since the course of some cognition and movement disorders may be associated typically with a worsening of the overall disease or disorder condition and symptoms thereof, the worsening referred to in connection with the aforementioned method is an unexpected or untypical worsening which goes beyond the normal course of disease or disorder progression. Unchanged, in this context, may thus also mean that the overall disease or disorder condition and the symptoms accompanying it are within the normal cause of disease or disorder progression.

Further, the present disclosure contemplates a method of monitoring a cognition and movement disease or disorder in a subject comprising determining whether the cognition and movement disease or disorder improves, worsens or remains unchanged in a subject by carrying out the steps of the aforementioned method of the disclosure (i.e., the method for identifying a subject as suffering from a cognition and movement disease or disorder) at least two times during a predefined monitoring period.

The term "predefined monitoring period" as used herein refers to a predefined time period in which activity measurements are carried out at least two times. Typically, such a period may range from days to weeks to months to years depending on the course of disease or disorder progression to be expected for the individual subject. Within the monitoring period, the activity measurements and parameters are determined at a first time point, which is usually the start of the monitoring period, and at least one further time point. However, it is also possible that there is more than one further time point for activity measurements and parameter determination. In any event, the fine motoric activity parameter(s) determined from the activity measurements of the first time point are compared to such parameters of subsequent time points. Based on such a comparison, quantitative differences can be identified which will be used to determine a worsening, improvement or unchanged disease condition during the predefined monitoring period.

The present disclosure relates to a mobile device comprising a processor, at least one sensor and a database, as well as software, which is tangibly embedded to said device and, when running on said device, carries out any one of the disclosed methods.

Further contemplated is a system comprising a mobile device with at least one sensor and a remote device with a processor and a database as well as software, which is tangibly embedded to said device and, when running on said device, carries out any one of the methods of this disclosure, wherein said mobile device and said remote device are operatively linked to each other.

"Operatively linked to each other" it is to be understood as meaning that the devices are connected as to allow data transfer from one device to the other device. Typically, it is envisaged that at least the mobile device, which acquires data from the subject, is connect to the remote device carrying out the steps of the methods of the disclosure such that the acquired data can be transmitted for processing to the remote device. However, the remote device may also transmit data to the mobile device such as signals controlling or supervising its proper function. The connection between the mobile device and the remote device may be achieved by a permanent or temporary physical connection, such as coaxial, fiber, fiber-optic or twisted-pair, 10 BASE-T cables. Alternatively, it may be achieved by a temporary or permanent wireless connection using, e.g., radio waves, such as Wi-Fi, LTE, LTE-advanced or Bluetooth. Further details may be found elsewhere in this specification. For data acquisition, the mobile device may comprise a user interface such as a screen or other equipment for data acquisition. Typically, the activity measurements can be performed on a screen of a mobile device, wherein it will be understood that the said screen may have different sizes including, e.g., a 5.1 inch screen.

Also, the present disclosure relates to the use of the mobile device or the system of the present disclosure for identifying a subject suffering from a cognition and movement disease or disorder.

The present disclosure also contemplates the use of the mobile device or the system for monitoring a subject suffering from a cognition and movement disease or disorder, in particular, in a real life, daily situation and on large scale.

Yet, it will be understood that the present disclosure contemplates the use of the mobile device or the system for investigating drug efficacy, e.g., also during clinical trials, in a subject suffering from a cognition and movement disease or disorder.

Further, the present disclosure contemplates the use of the mobile device or the system according to the present disclosure for facilitating and/or aiding therapeutic decision making for a subject suffering from a cognition and movement disease or disorder.

Furthermore, the present disclosure provides for the use of the mobile device or the system for supporting hospital management, rehabilitation measure management, health insurance assessments and management and/or supporting decisions in public health management with respect to subjects suffering from a cognition and movement disease or disorder.

Encompassed by the present disclosure is furthermore the use of the mobile device or the system according to the present disclosure for supporting a subject suffering from a cognition and movement disease or disorder with lifestyle and/or therapy recommendations.

Further particular embodiments are also listed as follows:

Embodiment 1

A method for assessing a cognition and movement disease or disorder in a subject suspected to suffer therefrom comprising the steps of:
a) determining at least one qualimetric activity parameter for cognition and/or fine motoric activity in a, typically, preexisting, dataset of cognition and/or fine motoric activity measurements obtained from said subject using a mobile device; and
b) comparing the determined at least one qualimetric activity parameter to a reference, whereby the cognition and movement disease or disorder will be assessed.

Embodiment 2

The method of embodiment 1, wherein said cognition and movement disease or disorder is a disease or disorder of the central and/or peripheral nervous system affecting the pyramidal, extrapyramidal, sensory or cerebellar system, or a neuromuscular disease or is a muscular disease or disorder.

Embodiment 3

The method of embodiment 1 or 2, wherein said cognition and movement disease or disorder is selected from the group consisting of: multiple sclerosis (MS), neuromyelitis optica (NMO) and NMO spectrum disorders, stroke, a cerebellar disorder, cerebellar ataxia, spastic paraplegia, essential tremor, myasthenia and myasthenic syndromes or other forms of neuromuscular disorders, muscular dystrophy, myositis or other muscular disorders, a peripheral neuropathy, cerebral palsy, extrapyramidal syndromes, Parkinson's disease, Huntington's disease, Alzheimer's disease, other forms of dementia, leukodystrophies, autism spectrum disorders, attention-deficit disorders (ADD/ADHD), intellectual disabilities as defined by DSM-5, impairment of cognitive performances and reserve related to aging, Parkinson's disease, Huntington's disease, a polyneuropathy, motor neuron diseases and amyotrophic lateral sclerosis (ALS).

Embodiment 4

The method of any one of embodiments 1 to 3, wherein the at least one qualimetric activity parameter is a cognitive qualimetric activity parameter indicative for fluctuations in neurocognitive functions, a hand/arm function qualimetric activity parameter indicative for fluctuations in manual dexterity or an ambulation qualimetric activity parameter indicative for movement fluctuations.

Embodiment 5

The method of any one of embodiments 1 to 4, wherein the said dataset of cognition and/or fine motoric activity measurements comprises data from a pinching test performed on a sensor surface of the mobile device and/or from a U-turn test (UTT), a 2-minute walk test (2MWT), a static balance test (SBT) or continuous analysis of gait (CAG) from passive monitoring.

Embodiment 6

The method of any one of embodiments 1 to 5, wherein the said dataset of cognition activity measurements comprises data from an Information Processing Speed (IPS) test on a sensor surface of the mobile device.

Embodiment 7

The method of embodiment 6, wherein information processing speed is determined as a qualimetric activity parameter by a computer-implemented method for automatically assessing information processing speed (IPS) in the test subject comprising the steps of:
  i) determining at least one first qualimetric activity parameter for sensorial transmission, cognition and motoric output activity and at least one second qualimetric activity parameter for sensorial transmission and motoric output activity in a preexisting dataset of cognition and/or fine motoric activity measurements comprising cognitive oculomotor activity measurements obtained from said test subject;
  ii) determining at least one third qualimetric activity parameter for cognition by comparing the said first and the said second qualimetric activity parameters to each other;
  iii) assessing the information processing speed in a subject based on the at least one first, second and third qualimetric activity parameters;
  iv) providing the said information processing speed as qualimetric activity parameter for cognition and/or fine motoric activity in step a) of the method.

Embodiment 8

The method of any one of embodiments 1 to 7, wherein said mobile device has been adapted for carrying out on the subject one or more of the tests referred to in embodiment 4 or 5, preferably, all tests referred to in these embodiments.

Embodiment 9

The method of embodiment 8, wherein said mobile device is comprised in a smartphone, smartwatch, wearable sensor, portable multimedia device or tablet computer.

Embodiment 10

The method of any one of embodiments 1 to 9, wherein said reference is at least one qualimetric activity parameter for cognition and/or fine motoric activity derived from a dataset of cognition and/or fine motoric activity measurements obtained from the said subject at a time point prior to the time point when the dataset of cognition and/or fine motoric activity measurements referred to in step a) has been obtained from the subject.

Embodiment 11

The method of embodiment 10, wherein a worsening between the determined at least one qualimetric activity parameter and the reference is indicative of a subject that suffers from the cognition and movement disease or disorder.

Embodiment 12

The method of any one of embodiments 1 to 9, wherein said reference is at least one qualimetric activity parameter for cognition and/or fine motoric activity derived from a dataset of cognition and/or fine motoric activity measurements obtained from a subject or group of subjects known to suffer from the cognition and movement disease or disorder.

Embodiment 13

The method of embodiment 12, wherein a determined at least one qualimetric activity parameter being essentially the same as the reference is indicative of a subject that suffers from the cognition and movement disease or disorder.

Embodiment 14

The method of any one of embodiments 1 to 9, wherein said reference is at least one qualimetric activity parameter for cognition and/or fine motoric activity derived from a dataset of cognition and/or fine motoric activity measurements obtained from a subject or group of subjects known not to suffer from the cognition and movement disease or disorder.

Embodiment 15

The method of embodiment 14, wherein a determined at least one qualimetric activity parameter being worsened compared to the reference is indicative of a subject that suffers from the cognition and movement disease or disorder.

Embodiment 16

A method for recommending a therapy for a cognition and movement disease or disorder comprising the steps of the method of any one of embodiments 1 to 15 and the further step of recommending the therapy if the cognition and movement disease or disorder is assessed.

Embodiment 17

A method for determining efficacy of a therapy against a cognition and movement disease or disorder comprising the steps of the method of any one of embodiments 1 to 15 and the further step of determining a therapy response if improvement of the cognition and movement disease or disorder occurs in the subject undergoing therapy or determining a failure of response if worsening of the cognition and movement disease or disorder occurs in the subject undergoing therapy or if the cognition and movement disease or disorder remains unchanged.

Embodiment 18

A method of monitoring a cognition and movement disease or disorder in a subject comprising determining whether the cognition and movement disease or disorder improves, worsens or remains unchanged in a subject by carrying out the steps of the method of any one of embodiments 1 to 15 at least two times during a predefined monitoring period.

Embodiment 19

A mobile device comprising a processor, at least one sensor and a database as well as software which is tangibly embedded to said device and, when running on said device, carries out the method of any one of embodiments 1 to 18.

Embodiment 21

A system comprising a mobile device comprising at least one sensor and a remote device comprising a processor and a database as well as software which is tangibly embedded to said device and, when running on said device, carries out the method of any one of embodiments 1 to 18, wherein said mobile device and said remote device are operatively linked to each other.

Embodiment 21

A mobile device of the embodiment 19 or the system of embodiment 21 for use in identifying a subject suffering from a cognition and movement disease or disorder.

Embodiment 22

A mobile device of embodiment 19 or the system of embodiment 20 for use in monitoring a subject suffering from a cognition and movement disease or disorder, in particular, in a real life, daily situation and on large scale, for investigating drug efficacy, e.g., also during clinical trials, in a subject suffering from a cognition and movement disease or disorder, for facilitating and/or aiding therapeutic decision making for a subject suffering from a cognition and movement disease or disorder, for supporting hospital management, rehabilitation measure management, health insurance assessments and management and/or supporting decisions in public health management with respect to subjects suffering from a cognition and movement disease or disorder or for supporting a subject suffering from a cognition and movement disease or disorder with lifestyle and/or therapy recommendations.

All references cited throughout this specification are herewith incorporated by reference with respect to their entire disclosure content and with respect to the specific disclosure contents mentioned in the specification.

BRIEF DESCRIPTION OF DRAWINGS

The above-mentioned aspects of exemplary embodiments will become more apparent and will be better understood by reference to the following description of the embodiments taken in conjunction with the accompanying drawings, wherein.

Performance based on patient's UTT U-turn speed distribution. $*p<0.05$; $\dagger p<0.01$; $\ddagger p<0.001$. EDSS, Expanded Disability Status Scale; MS, multiple sclerosis; T25FW, Timed 25-Foot Walk.

FIGS. 4A-4D show examples of ambulation qualimetric activity parameters measuring fluctuations in walking quality in the UTT and continuous analysis of gait from the passive monitoring. The turning speed from UTT, the number of daily turns while walking and the average daily turning speed are depicted in the graphs (interim analysis of NCT02952911) to illustrate the ability of intra-subject day-to-day monitoring of these qualimetric parameters to detect a multiple sclerosis relapse. Clear differences in active test U-turn speed measured with the UTT was observed in this example between prior to reporting a relapse and after (Wilcoxon rank sum test; FIG. 4B). Turning behavior in passive monitoring was also different before versus after relapse onset/reporting for the number of daily turns (FIG. 4C), while the average daily turn speed remained unchanged (FIG. 4D).

Figure 5A:
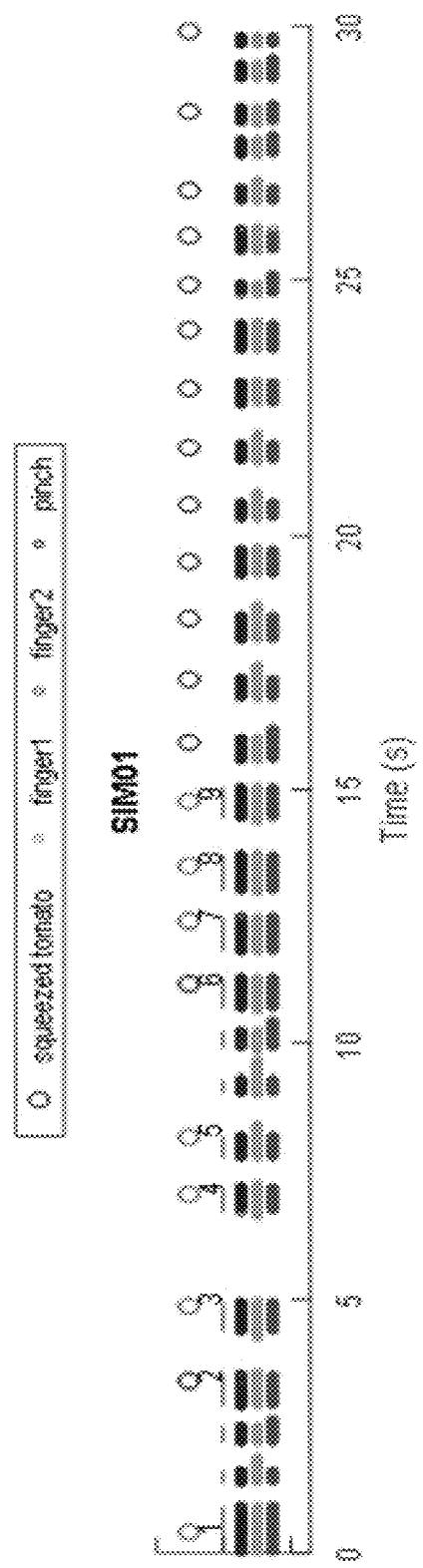
Figure 5B:
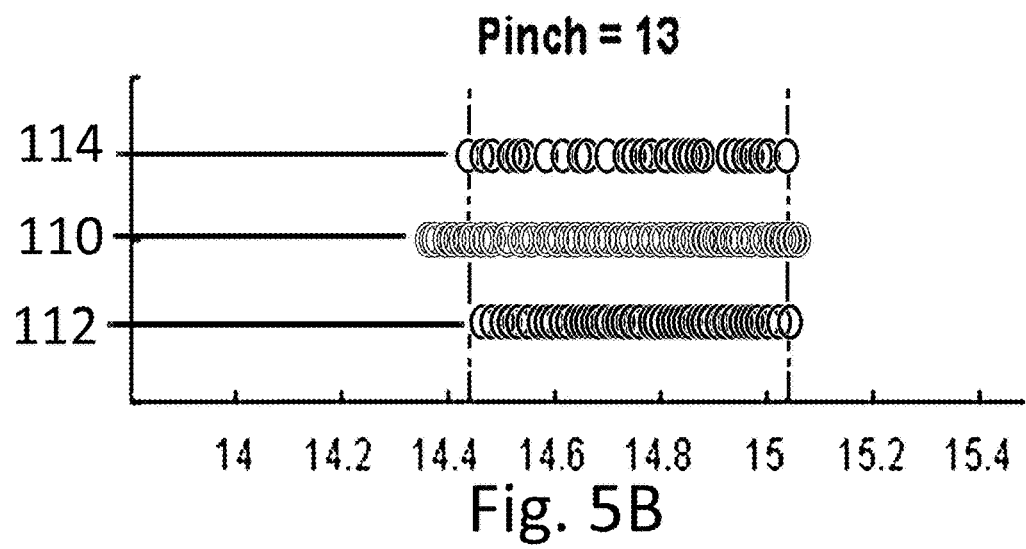
Figure 5C:
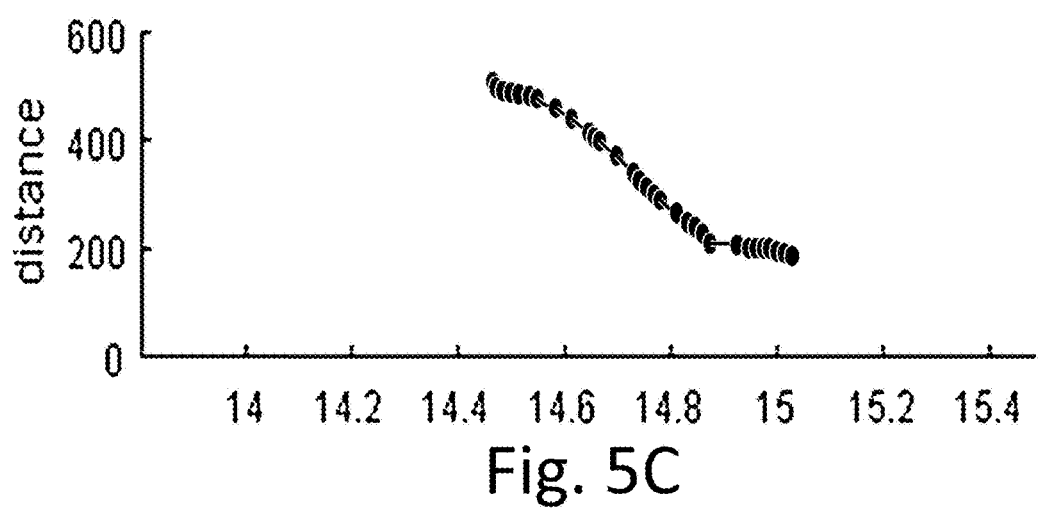
Figure 5D:
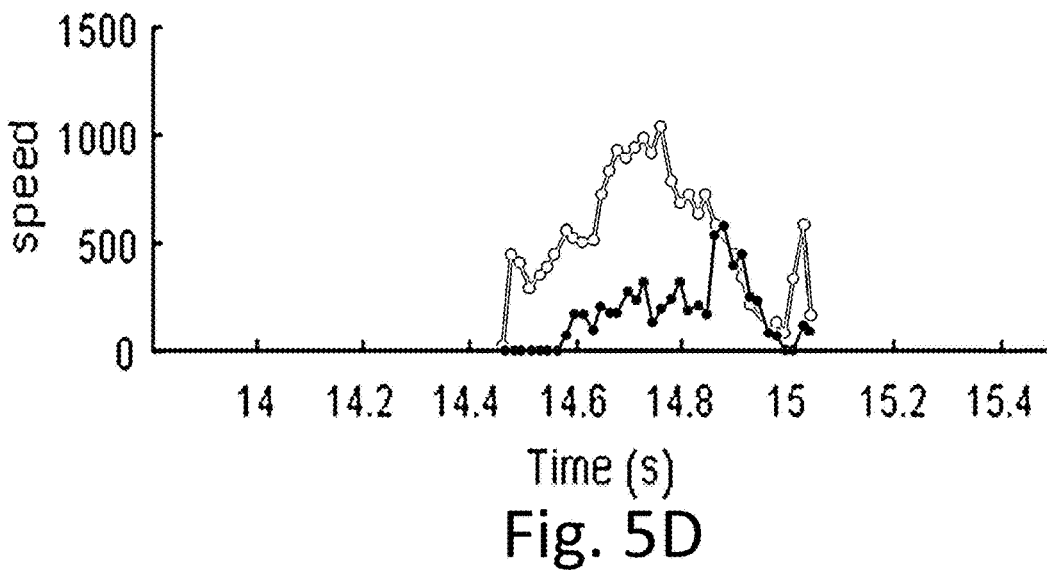
Figure 5E:
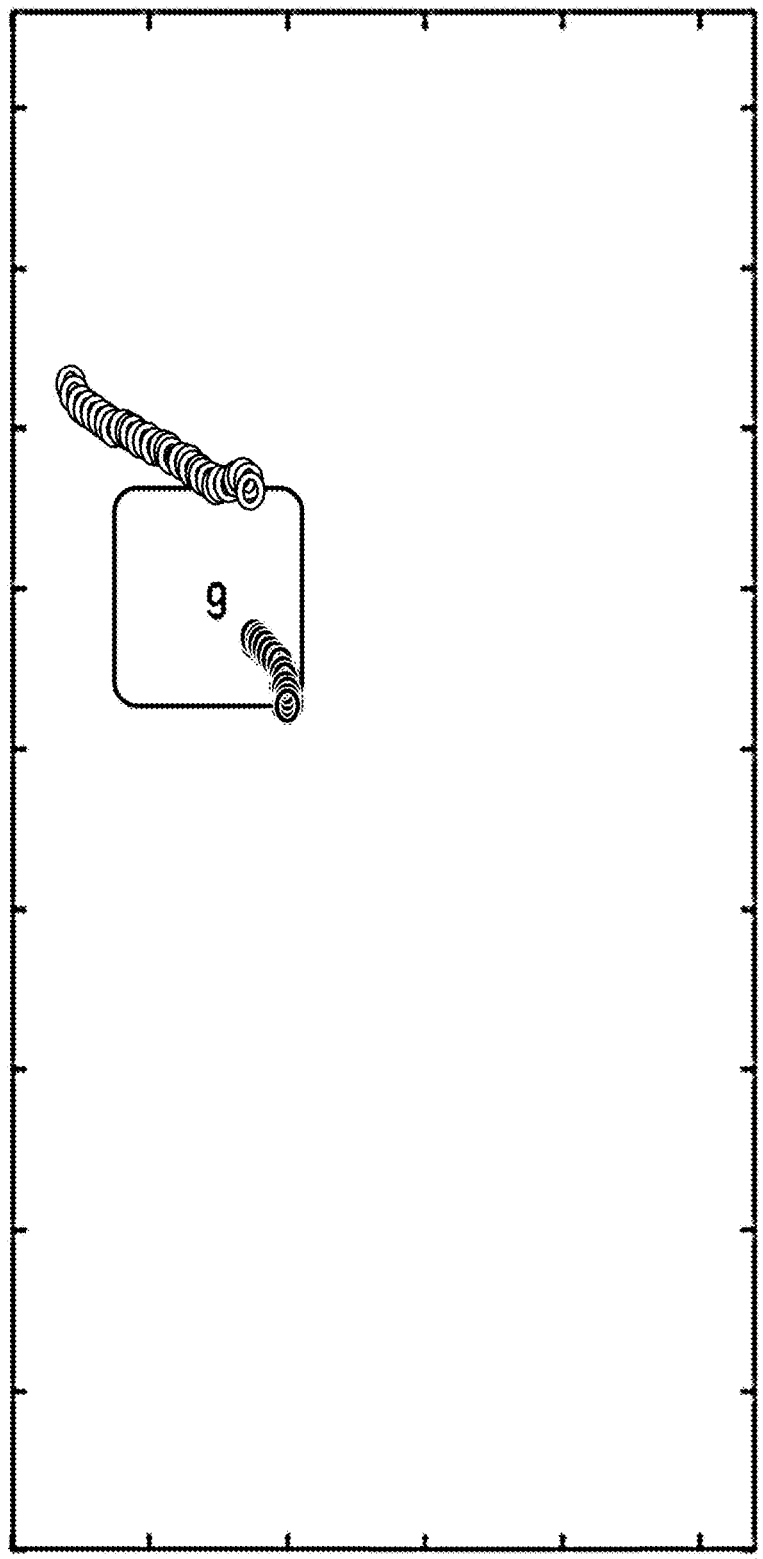

FIGS. 5A-5E show Pinching test qualimetric activity parameters, i.e., an illustration of pinching test qualimetric data. FIG. 5A shows an overview of a subject performing the test for 30 seconds. Circles 110 in FIG. 5B illustrate the touch events from the first finger and circles 112 show the second finger touch events. Circles 114 in FIG. 5B show whenever two contact points with the display were made at the same time. The dotted lines show the start and end of a pinch attempt, respectively. FIG. 5C shows the distance between the two pinching fingers. The speed of individual fingers is depicted in FIG. 5D. FIG. 5E depicts the location of the 9th tomato that is successfully pinched with the 13th pinch at first attempt. The circles show the finger movement trajectory on the touch screen. The box color indicates that the pinch attempt was successful.

Figure 6A:
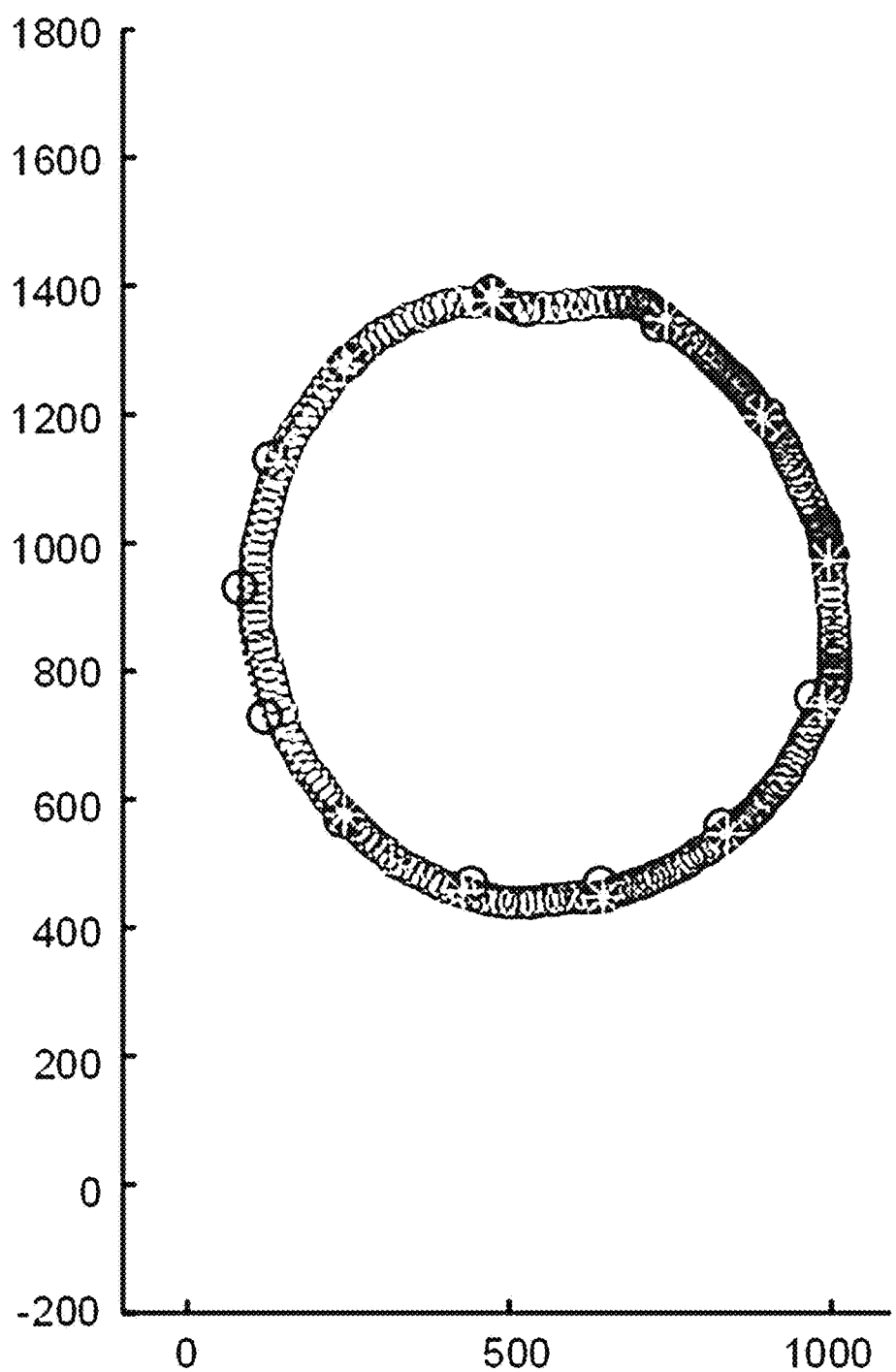
Figure 6B:
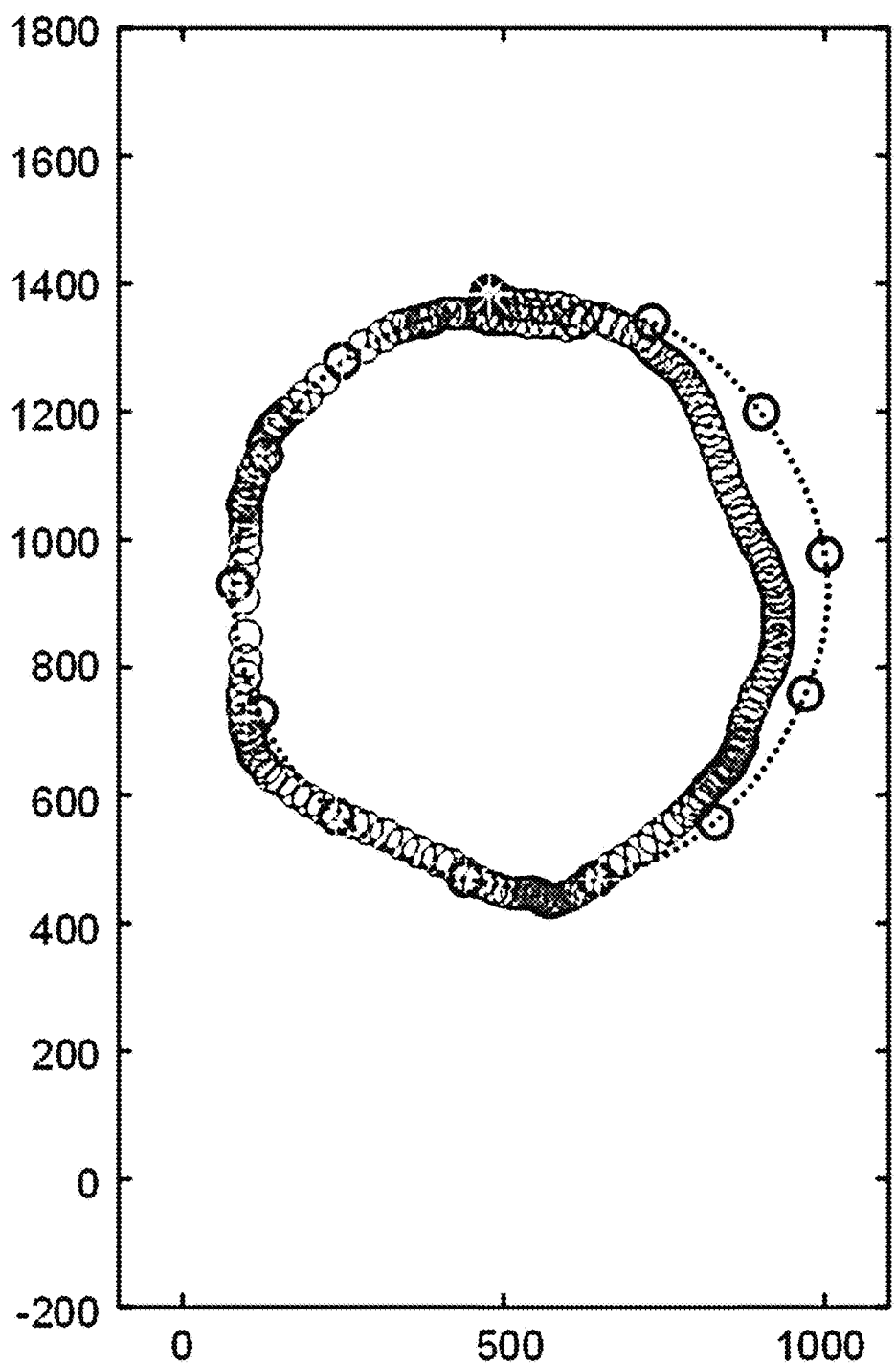

FIGS. 6A and 6B show the Draw a shape test qualimetric activity parameter, i.e., examples of touch traces for a circle shape from two subjects. Solid black circles indicate waypoints that subjects have to pass through. Each asterisk represents the closest trace point to each waypoint. FIG. 6A shows the baseline subject, chosen based on good 9HPT performance. FIG. 6B depicts a subject with poor 9HPT.

Figure 7A:
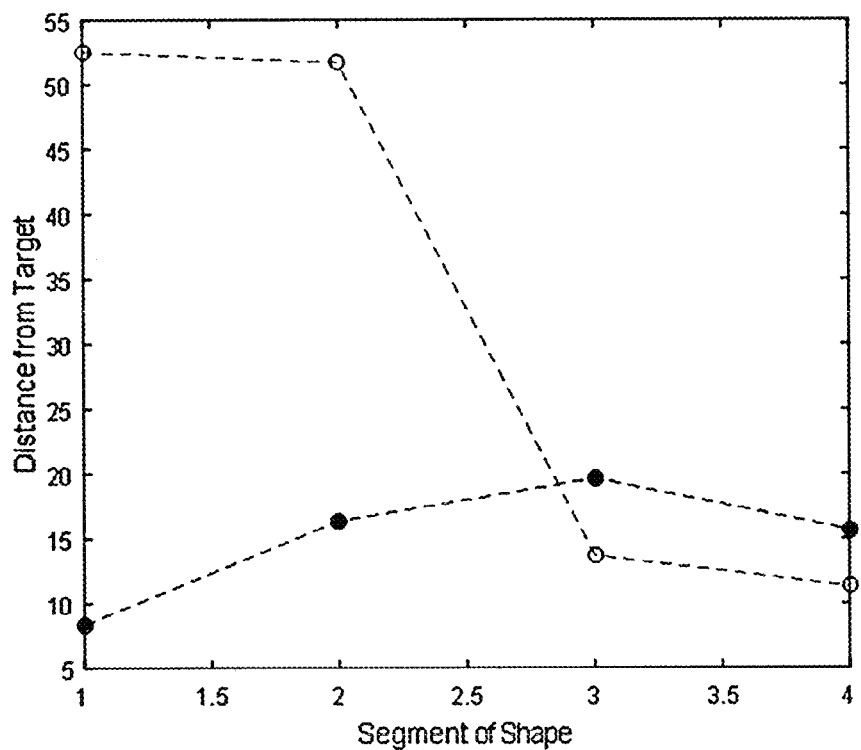
Figure 7B:
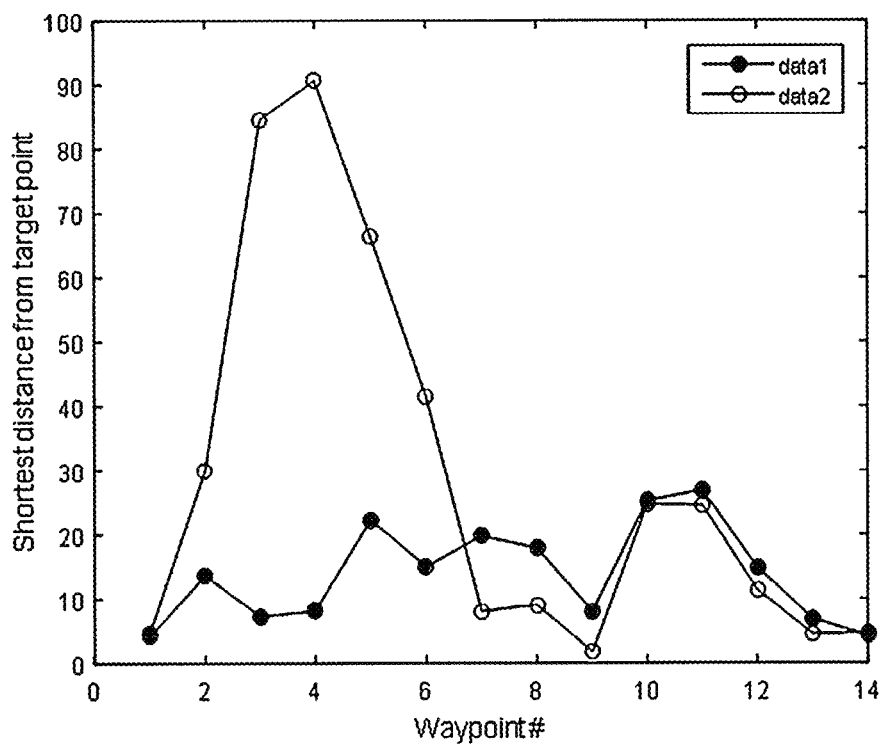
Figure 7C:
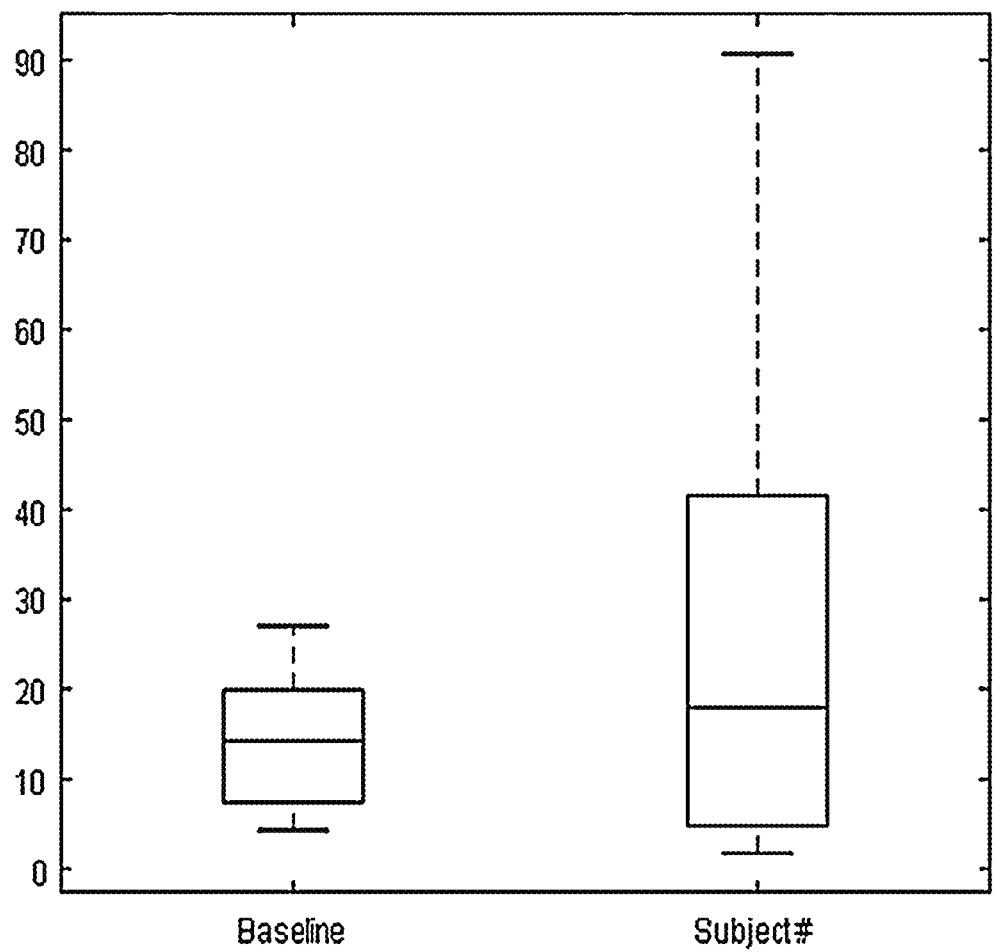

FIGS. 7A-7C show Draw a shape test qualimetric activity parameters, i.e., the tracing performance for examples shown in FIGS. 6A-6B. Error distances per each waypoint of circle shape are shown in FIG. 7A. FIG. 7B shows shape-specific segmentation into sectors, and subsequent error per sector. FIG. 7C shows the range of error distances per subject, including median and IQR.

Figure 8A:
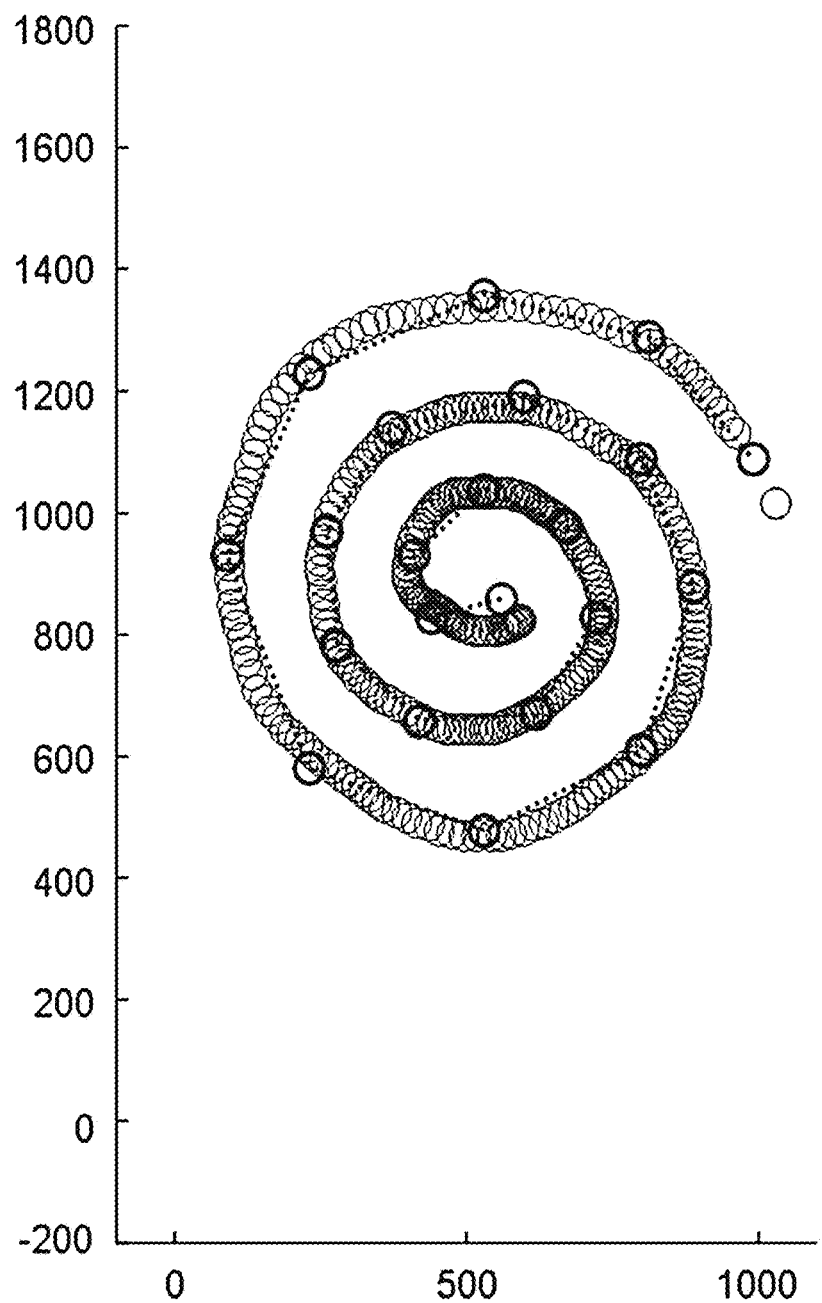
Figure 8B:
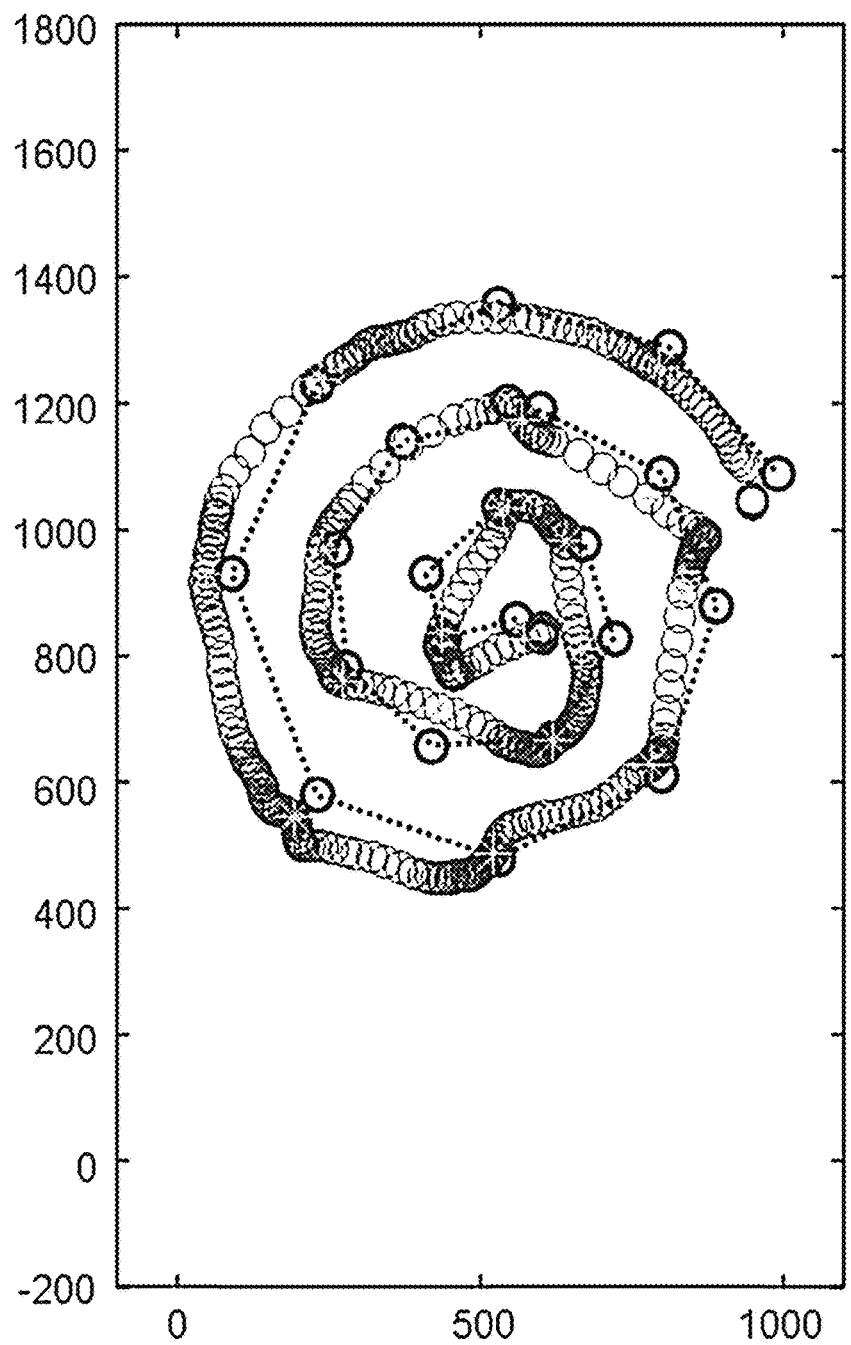

FIGS. 8A-8B show Draw a shape test qualimetric activity parameters, i.e., examples of touch traces for a spiral shape from two subjects. Solid black circles indicate waypoints that subjects have to pass through. Each asterisk represents the closest trace point to each waypoint. FIG. 8A shows the baseline subject, chosen based on good 9HPT performance. FIG. 8B depicts a subject with poor 9HPT.

Figure 9A:
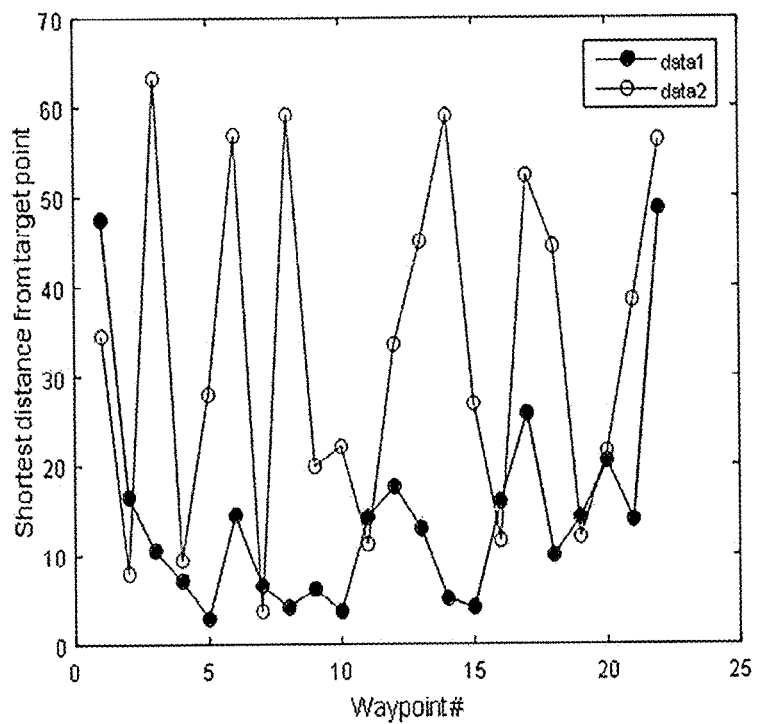
Figure 9B:
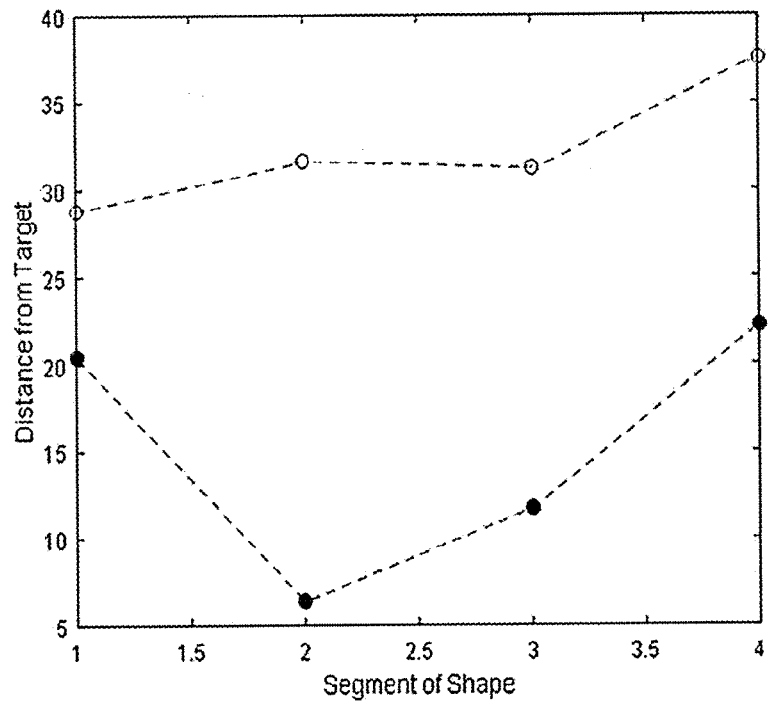
Figure 9C:
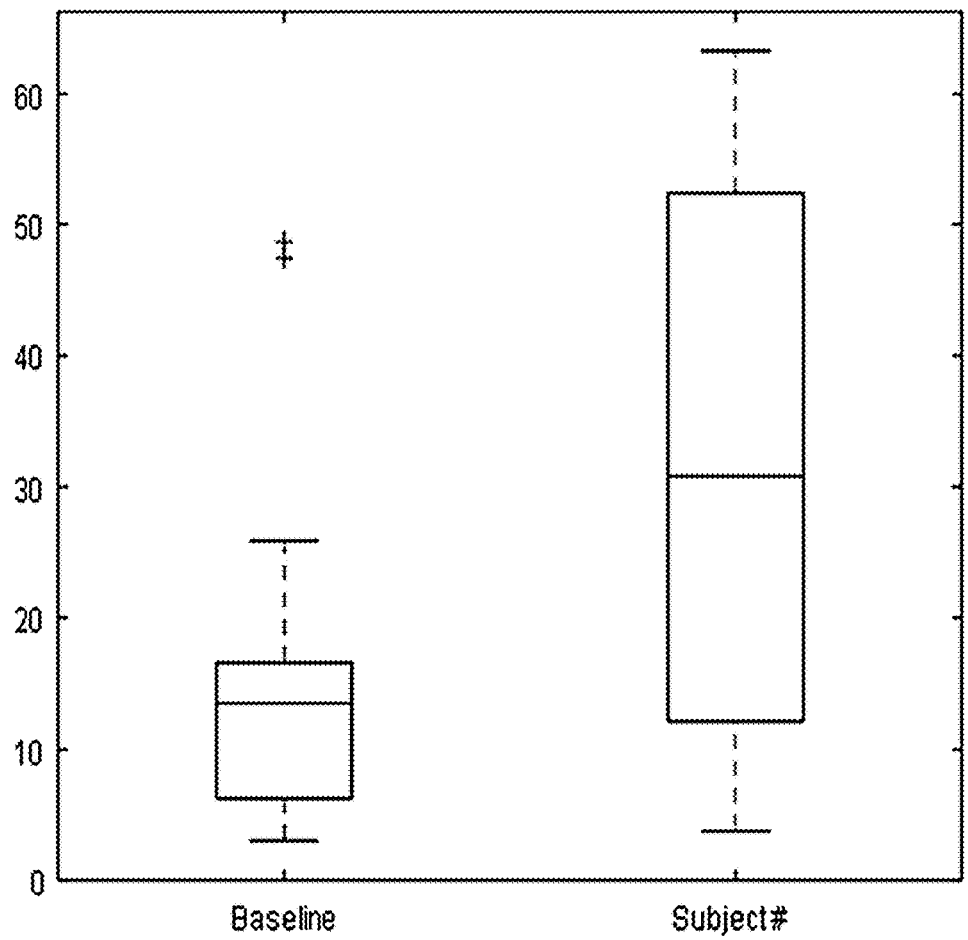

FIGS. 9A-9C show Draw a shape test qualimetric activity parameters, i.e., the tracing performance for examples shown in FIGS. 8A-8B. Error distances per each waypoint of spiral shape are shown in FIG. 9A. FIG. 9B shows shape specific segmentation into sectors, and subsequent error per sector. FIG. 9C shows the range of error distances per subject, including median and IQR.

Figure 10A:
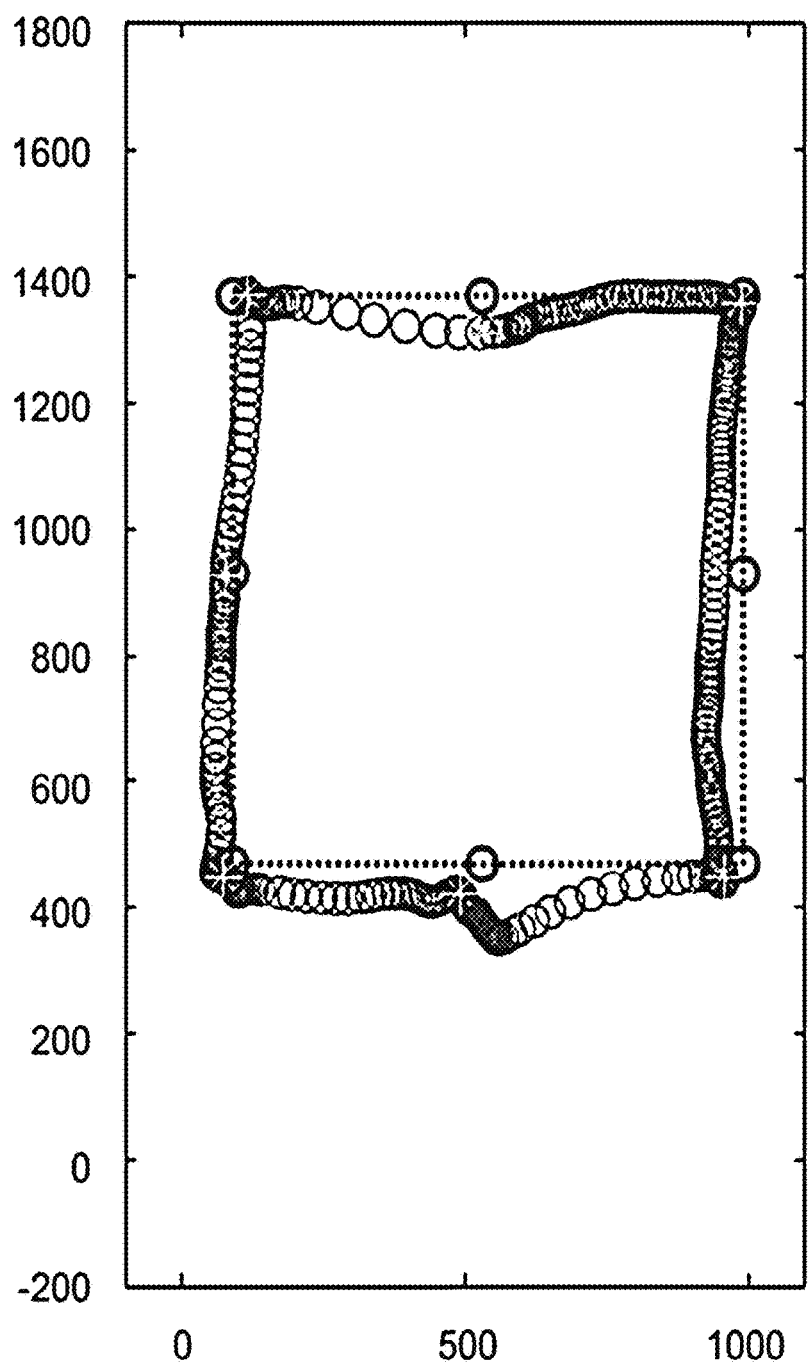
Figure 10B:
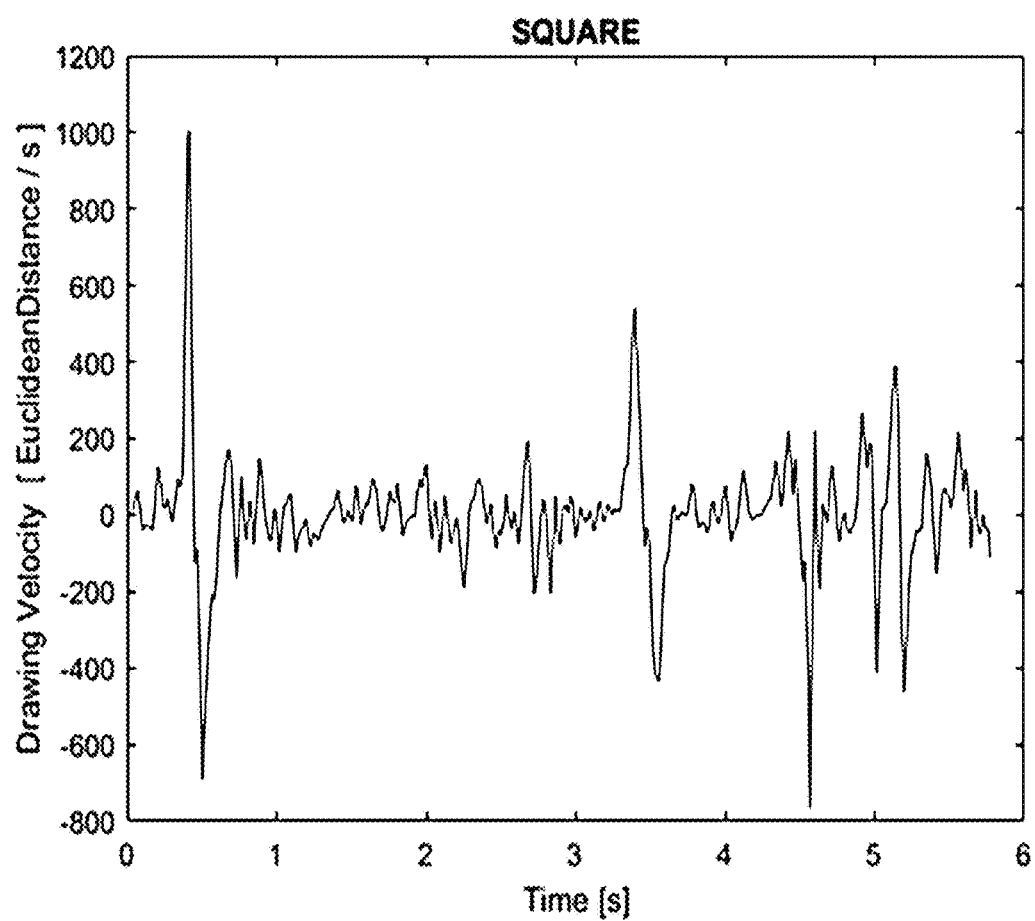
Figure 10C:
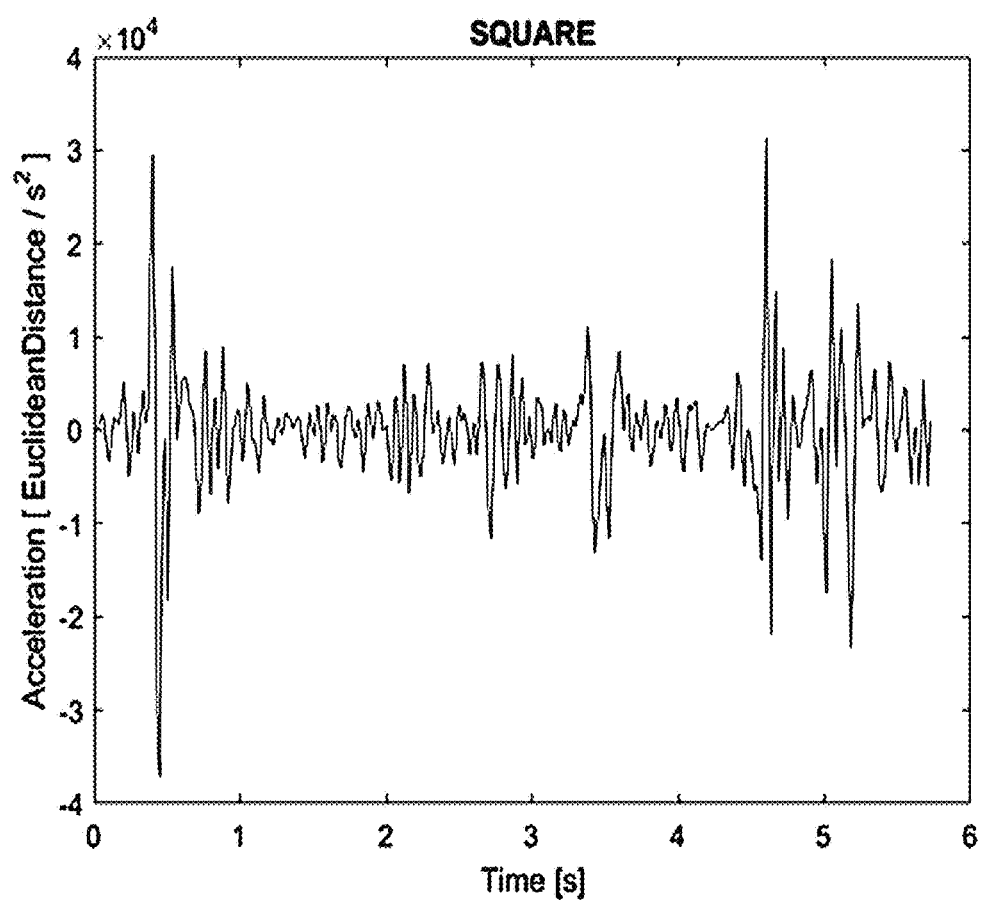

FIGS. 10A-10C show Draw-a-shape test qualimetric activity parameters, i.e., the collective spatial and temporal characteristics of a subject's drawing performance through visual, velocity and acceleration analysis. Velocity is calculated as the change in Euclidean distance between consecutive points over time; Acceleration is the rate of change of velocity over time. Through this shape and subject-specific complementary analysis to a spatial analysis of points drawn, a subject's fine temporal performance characteristics can be studied. FIG. 10A shows a visual tracing of a specified shape. FIG. 10B shows a velocity tracing of the Draw-a-shape task over time to complete [s]; and FIG. 10C shows acceleration tracing of Draw-a-Shape task over time to complete [s].

Figure 11:
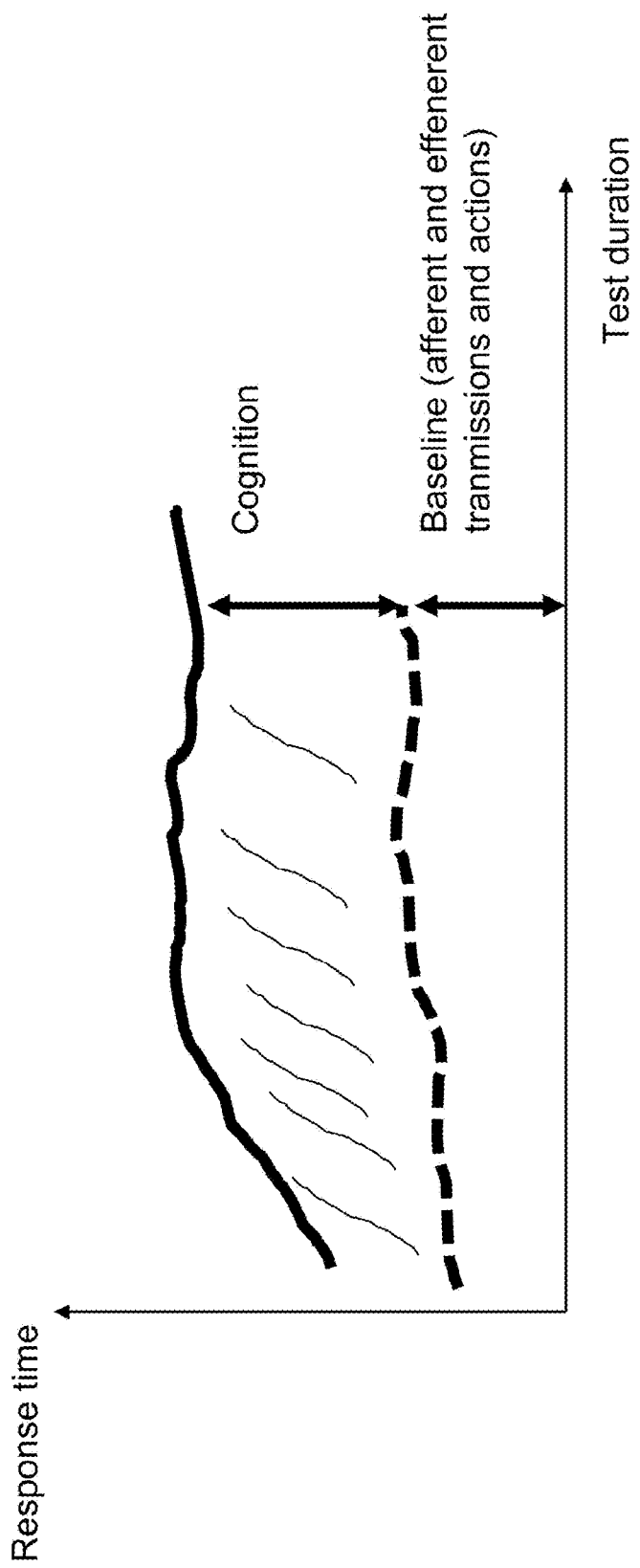

FIG. 11 shows schematically the variation of the response time in total and the baseline variation during the test performance. The difference between baseline and total response time accounts for cognitive activities.

Figure 12:

FIG. 12 shows the change in performance observed after several iterations of matching tasks. Performance increases in healthy volunteers and patients for matching tasks while baseline performance remains unaffected.

Figure 13A:
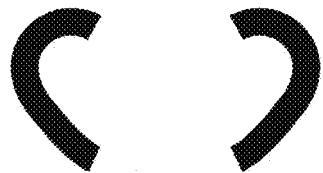
Figure 13B:
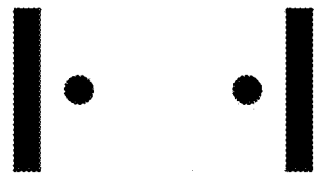
Figure 13C:
Figure 13D:
Figure 13E:
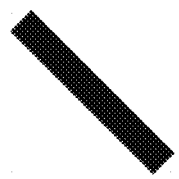
Figure 13F:
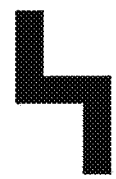

FIGS. 13A-13F show symbols useful for the IPS matching test. FIGS. 13A, 13B and 13C are symbol pairs, FIGS. 13D, 13E and 13F are singletons. FIG. 13A symbol is rounded, allows for strong association, and mirroring matches in reading direction; FIG. 13B symbol is segmented, results in confusing visual inspection, and mirroring in reading direction; FIG. 13C symbol is strongly edged, allows for strong association, has a prominent mirror axis perpendicular to the reading direction; FIG. 13D symbol has rotational symmetry, allows for easy visual inspection; FIG. 13E symbol is directional and reverse to reading axis; FIG. 13F symbol is edged, has two mirror axes in reading direction.

Figure 14A:
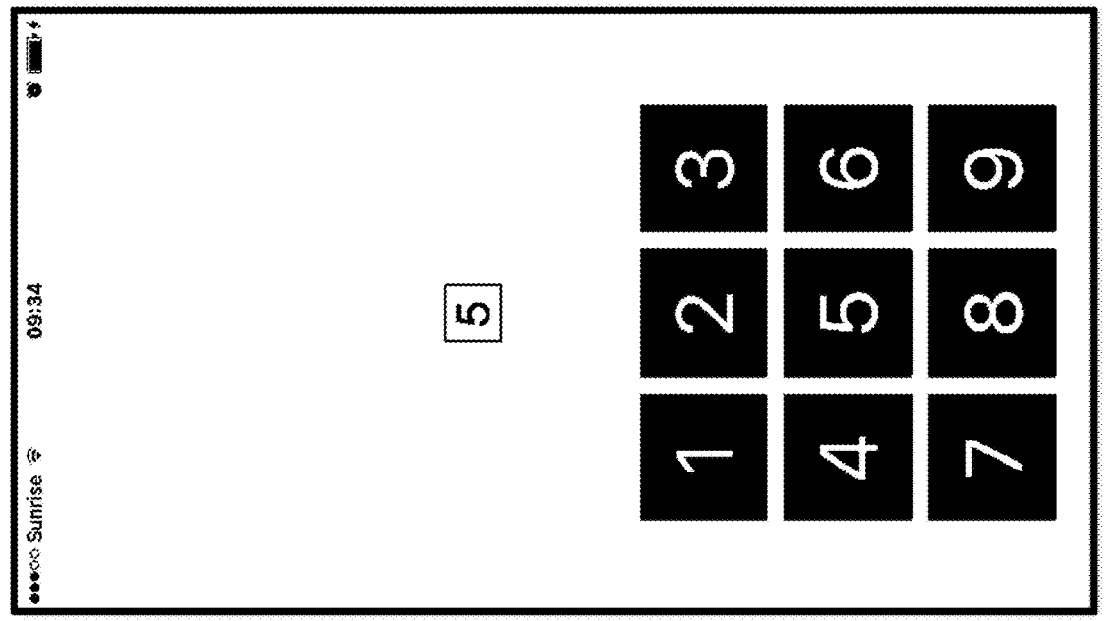
Figure 14B:
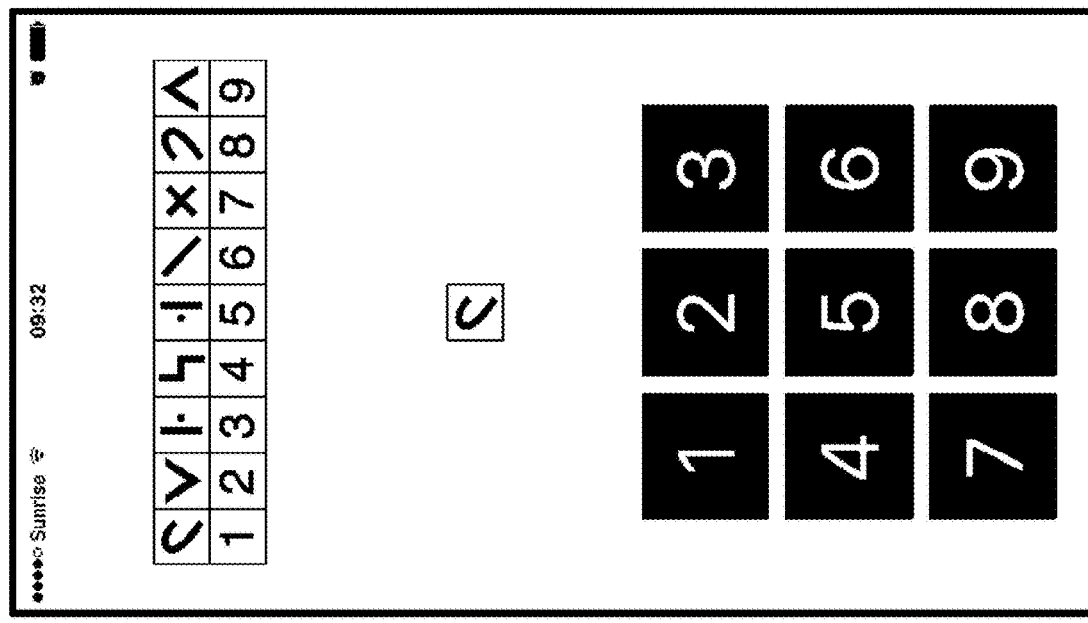

FIGS. 14A and 14B show IPS test setting on a display of a mobile device for symbol matching (FIG. 14A) and baseline task performance (FIG. 14B).

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Example 1: A Computer-Implemented (Electronic) Cognition-Information Processing Speed (IPS) Test a) IPS Test The aim of the information processing speed testing is to detect impairment of key neurocognitive functions that underlie an iterative visual substitution task, including sustained attention, visual scanning, and recent memory. Information processing in this instance is composed of different steps, starting with the input of visual information into the sensory system that secondarily extends to the output, i.e., responding by pressing a key on the smartphone touchscreen. The major steps in this process are (1) transmission of afferent visual sensory information, (2) the completion of the cognitive substitution task, and (3) execution of an efferent motor output (Costa 2017).

The symbol digit modalities test (SDMT, Smith 1968, 1982) or the processing speed test (PST, Rao 2017) do not account for any measurement of the relative weight of the reaction time or motor output time in the overall test performance. The IPS test has been developed to enable specific assessment of the speed of the symbol/digit substitution task by subtracting from the overall performance the reaction time, visual processing time, as well as the motor output time, which are measured separately.

The symbol set of the IPS test consists of 9 different abstract symbols which follow a simple design scheme and are assigned to nine keys, i.e., digits 1 to 9.

To account for participants' reaction time and the time it takes to produce the efferent motor output, a 15-second digit/digit matching exercise is done after the symbol/digit substitution task. The digits are presented in an analogue rotation scheme for the numbers as the symbols in the prior substitution task and are embedded in the same user interface.

For the symbol/digit substitution task of the IPS test, 120 abstract symbols will be displayed in sequence in a maximum of 90 seconds total. The legend key (round Robin alternation of 3 or more versions), showing the nine symbols with their respective matching digits from 1 to 9, will be displayed alongside for reference. The study participant is asked to provide as many correct responses as possible by typing, for each iterative symbol, the matching key as fast as possible on a numeric keypad on the smartphone's screen during 90 seconds.

The number of correct responses to symbol matching and the baseline test will be displayed to the patient.

b) Results

Examples of cognitive qualimetric activity parameters were developed from the above described Information Processing Speed (IPS) test, which is aimed at detecting and measuring impairment of key neurocognitive functions that underlie an iterative visual substitution task, including sustained attention, visual scanning, and recent memory. The digit to symbol substitution tasks are known to correlate with brain atrophy in conditions of mild cognitive impairment and the IPS test performed on a mobile device (differently from similar tests such as SDMT (Smith 1968, 1982) or PST (Rao 2017)) enables separate measurement of the cognitive substitution task performance while adjusting for any influence of the visual processing and motor execution time.

Figure 1:
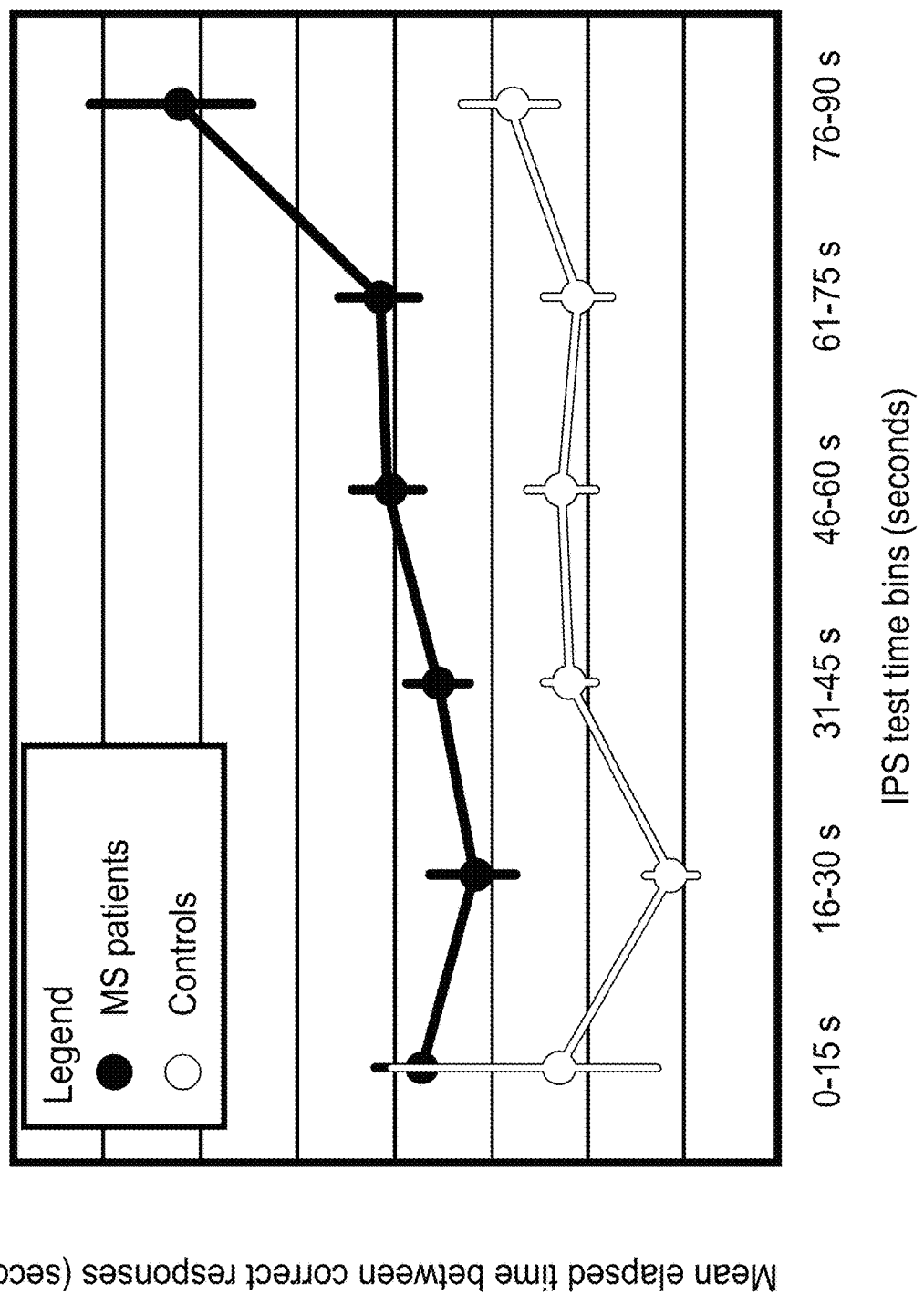
FIG. 1 shows an example of cognitive qualimetric activity parameter measuring fluctuations in processing speed and correctness in substitution task performance during the IPS test. The elapsed time between correct responses as depicted in the graph (interim analysis of clinical trial NCT02952911) illustrates, at the population level, a certain degree of intra-test 'fatigability' as a worsening is observed over time during the 90-second IPS test when the performance is monitored and analyzed, in this instance, by 15-second epochs.
Figure 2B:
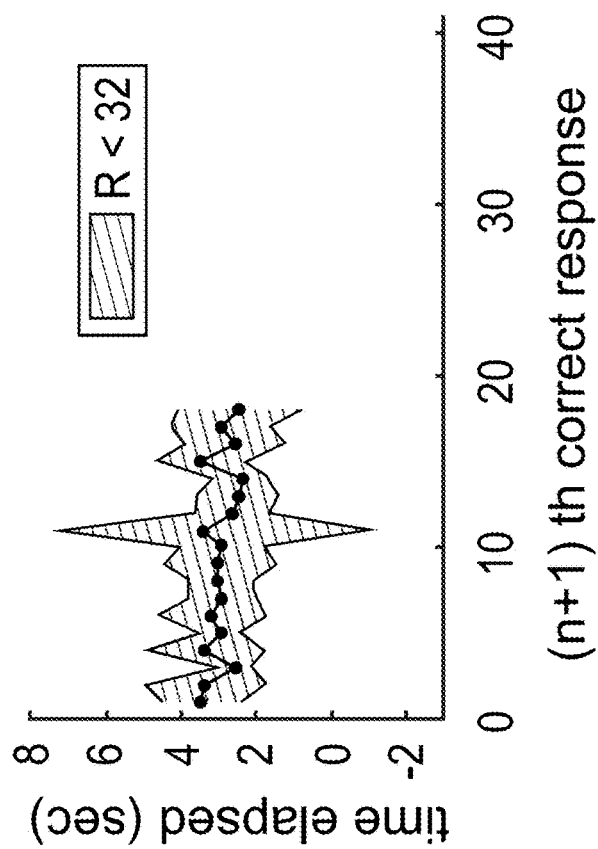
FIGS. 2A-2F show examples of variable temporal profiles of intra-test fluctuations in the time elapsed between overall symbol-digit substitution responses (FIGS. 2A, 2C and 2E) or correct symbol-digit substitution responses (FIGS. 2B, 2D and 2F) for 3 categories of subjects with respect to variable levels of overall IPS performances with a total number of correct responses in 90 seconds of <32 (FIGS. 2A and 2B), 32-39 (FIGS. 2C and 2D), or >40 (FIGS. 2E and 2F).
Figure 2A:
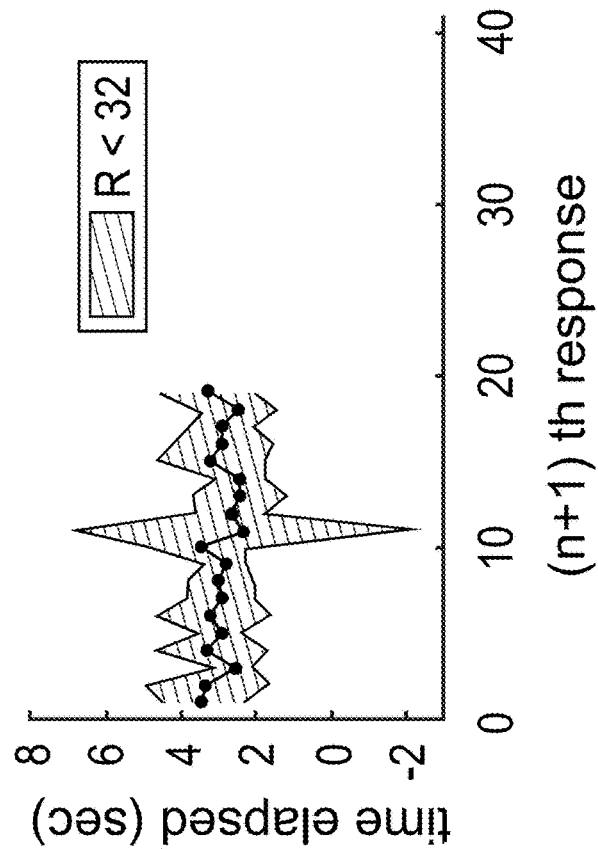
Figure 2D:
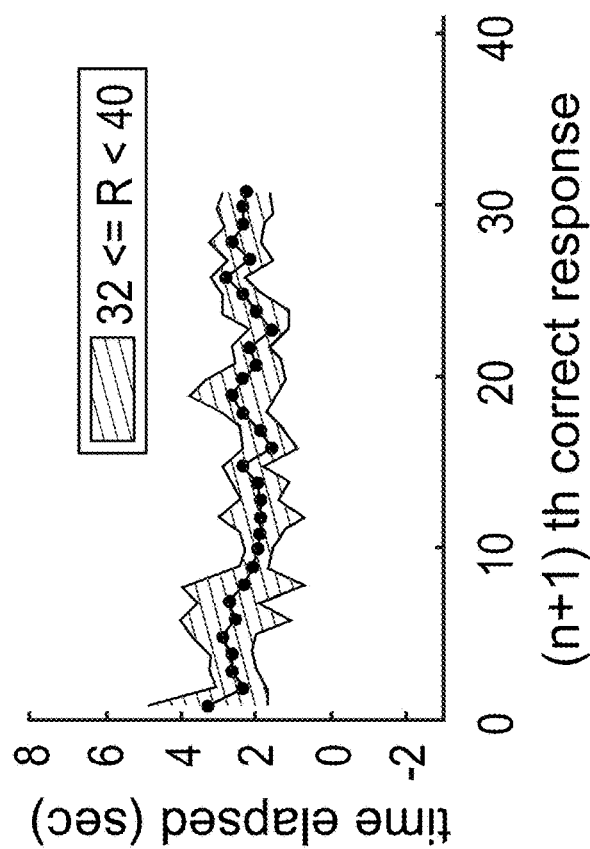
Figure 2C:
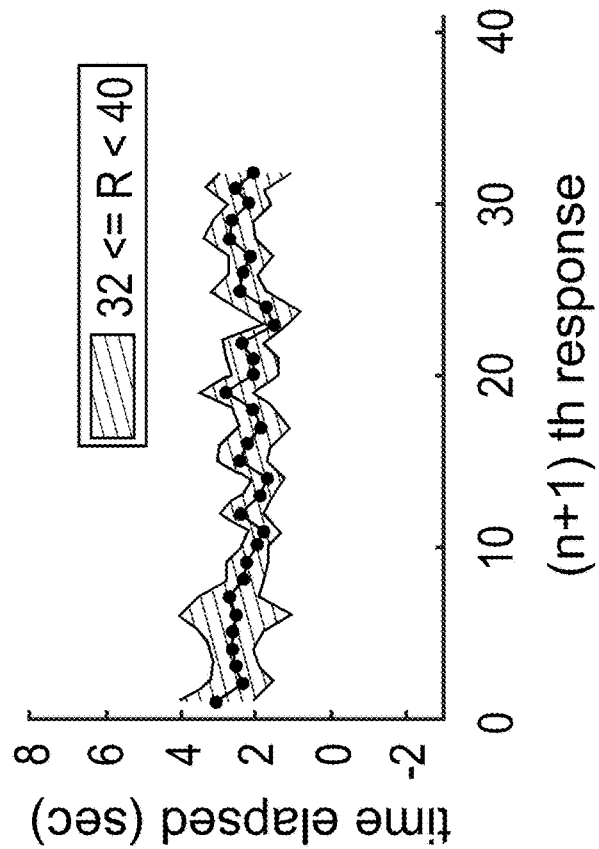
Figure 2F:
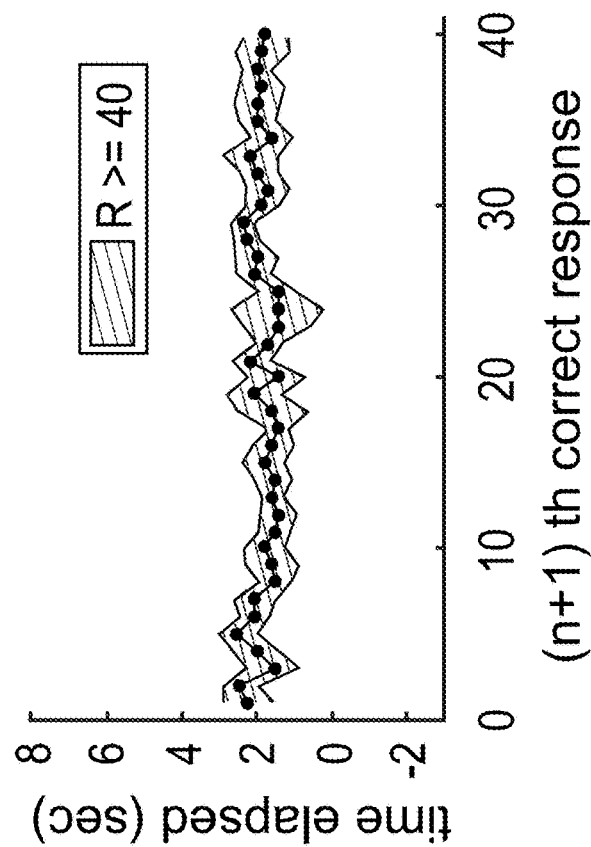
Figure 2E:
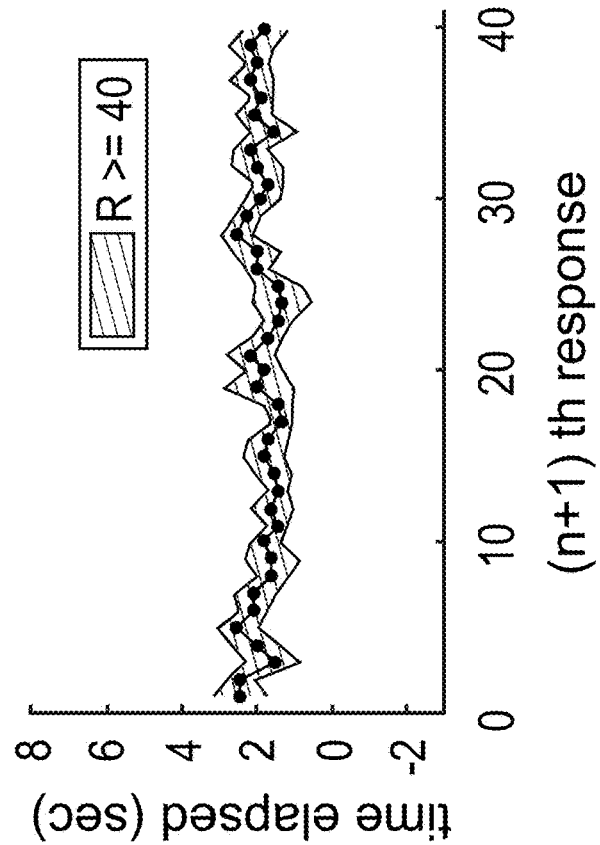

As an example of cognitive qualimetric activity parameter measuring fluctuations of processing speed and correctness in substitution task performance during the IPS test, the elapsed time between correct responses, as depicted in FIG. 1 (interim analysis of clinical trial NCT02952911), illustrates at the population level a certain degree of intra-test 'fatigability' as a worsening is observed over time during the 90-second IPS test when the performance is monitored and analyzed, in this instance, by 15-second epochs (see FIG. 1).

Variable temporal profiles of intra-test fluctuations in the time elapsed between overall symbol-digit substitution responses (FIGS. 2A, 2C and 2E) or correct symbol-digit substitution responses (FIGS. 2B, 2D and 2F) in 3 categories of subjects with respect to variable levels of overall IPS performances with a total number of correct responses in 90 seconds of <32 (FIGS. 2A and 2B), 32-39 (FIGS. 2C and 2D), or >40 (FIGS. 2E and 2F) are also shown in FIGS. 2A-2F.

Typical examples of cognitive qualimetric activity parameters derived from the IPS test and captured as continuous outcome variables reflecting intra-test fluctuations that measure cognitive integrity are, non-exhaustively, listed as follows: 1) the elapsed time before (from n-1) response, 2) the elapsed time before (from n-1) correct response, 3) the elapsed time before (from n-1) incorrect response, 4) the elapsed time between (from prior correct response) correct responses, 5) the elapsed time between (from prior incorrect response) incorrect responses, 6) the parameters 1), 2), and 3) applied to specific symbols or cluster of symbols when the sequence of symbols is modified to evaluate working memory and learning within the task.

Importantly, it will be understood that cognitive qualimetric activity parameters as aforementioned can be derived from any other cognitive test acquired from a mobile device and comprising single or composite measures of performance fluctuations in at least one qualitative feature of cognitive functioning and integrity during the completion of a specific cognitive task.

Example 2: Computer-Implemented "Draw a Shape" and "Pinching" Tests

Manual dexterity (hand motor function) characterizes an individual's ability to coordinate movement of the hand and fingers and manipulate objects in a timely manner. Manual dexterity greatly impacts a person's performance in daily activities, completing work related tasks, and engaging in leisure activities.

Manual dexterity was identified in 2007 as a core construct for inclusion in the National Institutes of Health Toolbox (NIH) Toolbox for the assessment of neurological and behavioral function, as part of the NIH Blueprint for Neuroscience Research initiative, which developed brief, yet comprehensive, instruments to measure motor, cognitive, sensory, and emotional function. After reviewing existing measures, experts recommended two candidate measures of manual dexterity: 1) 9-Hole Peg Test (9HPT), and 2) Grooved Pegboard Test (GPT) for potential inclusion in the NIH Toolbox because of their applicability across the life span, psychometric soundness, brevity (completion time for one trial is relatively short), and applicability in diverse settings.

Primarily, the 9HPT was selected because it met the most inclusion criteria and the test was easy to administer in all age groups, especially younger children. The time to administer the 9-hole peg test was brief (<5 min to measure for both hands) as required for inclusion in the NIH Toolbox. Existing literature supported 9HPT as a reliable and valid measure of finger dexterity, and as capable of assessing hand dexterity in various diagnostic groups (i.e., MS, stroke, cerebral palsy, cerebellar impairment, and Parkinson's disease).

Normative data for the 9HPT have been published across the age span, including children and elderly adults, and since the late 90 s, 9HPT represents the key component of functional upper limb assessment from the Multiple Sclerosis Functional Composite (MSFC) scale.

For the current study protocol, two touchscreen-based application tests were developed, "Draw a Shape" and "Pinching", aimed at replicating the characteristics of 9HPT and GPT on a user-friendly smartphone interface for enabling remote self-assessment of hand motor function in neurological disorders. Both tests are meant to last 30 seconds each.

"Draw a Shape" and "Pinching" tests evaluate upper limb motor function and manual dexterity (pinching, drawing) and will be sensitive to change and abnormalities in pyramidal, extrapyramidal, sensory and cerebellar components of upper limb nervous system but also to neuromuscular and myogenic alteration of upper limb function.

a) Draw a Shape

The aim of this test is to assess fine finger control & stroke sequencing. The test is considered to cover the following aspects of impaired hand motor function: tremor and spasticity and impaired hand-eye coordination. The patients are instructed to hold the smartphone device in the untested hand and draw on the smartphone touchscreen six pre-written alternating shapes of increasing complexity (linear, rectangular, circular, sinusoidal, and spiral; vide infra) with the index finger of the tested hand "as fast and as accurately as possible" within a maximum time of 30 seconds. To "Draw a Shape" successfully the patient's finger has to slide continuously on the touchscreen and connect indicated start and endpoints, passing through all indicated check points and keeping within the boundaries of the writing path as much as possible. The patient has a maximum of two attempts to successfully complete each of the six shapes. Tests will be alternatingly performed with right and left hand. The user will be instructed on daily alternation.

The two linear shapes each have five checkpoints to connect, i.e., four segments. The square shape has nine checkpoints to connect, i.e., eight segments. The circular shape has 14 checkpoints to connect, i.e., 13 segments. The eight-shape has 13 checkpoints to connect, i.e., 12 segments. The spiral shape has 22 checkpoints to connect, i.e., 21 segments. Completing the six shapes, then, implies successfully drawing a total of 62 segments.

The accuracy of the drawing and the time used to draw the shape will be reported to the patient. In addition, the summed length of all drawings made will be reported and depicted with familiar objects (for example: size of a dog, horse, and building).

b) Pinching Test

The aim of this test is to assess fine distal motor manipulation (gripping and grasping) and control by evaluating accuracy of pinch closed finger movement. The test is considered to cover the following aspects of impaired hand motor function: impaired gripping/grasping function, muscle weakness, and impaired hand-eye coordination. The patients are instructed to hold the smartphone device in the untested hand, and by touching the screen with two fingers from the opposite hand (preferably thumb+index finger or thumb+third finger), to squeeze/pinch as many of the displayed round shapes (i.e., tomatoes) as they can during 30 seconds. Impaired fine motor manipulation will affect the performance. Tests will be alternatingly performed with right and left hand. The user will be instructed on daily alternation.

The number of successful pinched shapes (i.e., tomatoes) will be reported to the patient. In addition the total number of pinched tomatoes will be reported in familiar, easy to understand symbols (for example: tomato equivalent as ketchup bottles).

Examples of hand/arm function qualimetric activity parameters have been developed from the Pinching and draw a shape tests described above.

c) Results

Some examples of hand/arm function qualimetric activity parameters derived from the pinching test (FIGS. 5A-5E) and captured as continuous outcome variables reflecting intra-test fluctuations that measure hand/arm function integrity and manual dexterity are non-exhaustively listed as follows: 1) elapsed time between 2 successive pinching attempts, defined as double contact on the touchscreen followed by pinching attempt, 2) Double touching asynchrony, measured as the lag time between first and second fingers touching the screen for all double contacts detected, 3) the pinching target precision, measured as the distance from an equidistant point between the starting touch points of the two fingers at double contact to the center of the tomato shape, for all double contacts detected, 4) pinching finger movement asymmetry, measured as the ratio between respective distances slid by the two fingers (shortest/longest) from the double contact starting points until reaching pinch gap, for all double contacts successfully pinching, 5) the pinching finger velocity, measured as the speed (mm/sec) of each one and/or both fingers sliding on the screen from time of double contact until reaching pinch gap, for all double contacts successfully pinching, 6) the pinching finger asynchrony, measured as the ratio between velocities of respective individual fingers sliding on the screen (slowest/fastest) from the time of double contact until reaching pinch gap, for all double contacts successfully pinching, 7) the continuous variable analysis of 1) to 6) over time, as well as their analysis by epochs of variable duration.

Figure 3:
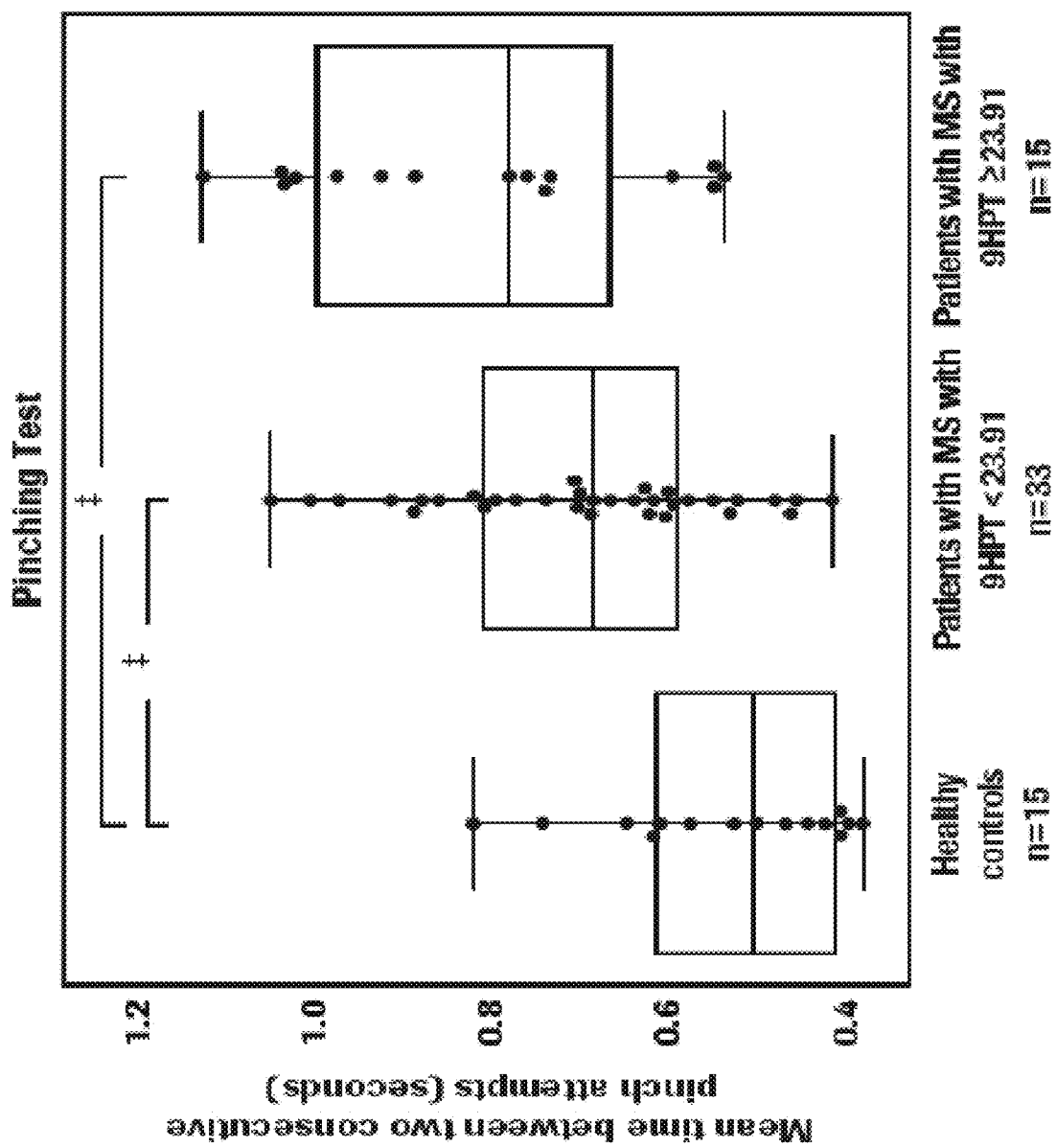
FIG. 3 shows an example of hand/arm function qualimetric activity parameter measuring fluctuations of manual dexterity in the pinching task performance during the Pinching test. The elapsed time between 2 consecutive pinching attempts is depicted in the graph (interim analysis of clinical trial NCT02952911) to illustrate, at the population level, that this particular feature is more capable of detecting abnormal function than the conventional 9-hole peg test (9HPT). In fact, when comparing NCT02952911 study patients with MS patients who had presumably normal and impaired hand/arm function (based on a threshold [23.91 seconds] defining upper limit of normal function corresponding to the average 9HPT time for healthy controls (HCs) plus two standard deviations (Wang 2015)) it was possible to distinguish patients with MS with normal hand/arm function from HCs by their mean time between two consecutive pinch attempts ($\ddagger p<0.001$).

As an example of a hand/arm function qualimetric activity parameter measuring fluctuations of manual dexterity in the pinching task performance during the Pinching test, the elapsed time between 2 consecutive pinching attempts is depicted in FIG. 3 (interim analysis of clinical trial NCT02952911) to illustrate at the population level that this particular feature is more capable of detecting abnormal function than the conventional 9-hole peg test (9HPT). As a matter of fact, when comparing NCT02952911 study patients with MS who had presumably normal and impaired hand/arm function (based on a threshold (23.91 seconds) defining upper limit of normal function corresponding to the average 9HPT time for healthy controls (HCs) plus two standard deviations (Wang 2015)), it was possible to distinguish patients with MS with normal hand/arm function from HCs by their mean time between two consecutive pinch attempts ($\ddagger$p<0.001); see FIG. 3.

Some examples of hand/arm function qualimetric activity parameters derived from the draw a shape test and captured as continuous outcome variables reflecting intra-test fluctuations that measure hand/arm function integrity and manual dexterity will be based on celerity and accuracy features and are, non-exhaustively, listed as follows (see FIGS. 6A to 10C): 1) celerity (segments/second) of successfully completed segments, 2) shape-specific (linear, circular, spiral) celerity for successfully completed segments, 3) deviation calculated as the sum of overall area under the curve (AUC) measures of integrated surface deviations between the drawn trajectory and the target drawing path from starting to ending waypoints that were reached for each specific shape divided by the total cumulative length of the corresponding target path within these shapes (from starting to ending waypoints that were reached), 4) shape-specific (linear, circular, spiral) deviation.

Example 3: A Computer-Implemented U-Turn Test (UTT), the 2-Minute Walk Test (2MWT), the Static Balance Test (SBT) and Continuous Analysis of Gait (CAG) from Passive Monitoring a) Two Minute Walking Test (2MWT)

The aim of this test is to assess difficulties, fatigability or unusual patterns in long-distance walking by capturing gait features in a 2MWT. Data will be captured from smartphone sensors. A decrease of stride and step length, increase in stride duration, increase in step duration and asymmetry and less periodic strides and steps may be observed in case of disability progression or emerging relapse (Hobart 2013). A patient will be instructed to "walk as fast and as long as you can for 2 minutes but walk safely." The 2MWT is a simple test that is required to be performed indoor or outdoor, on even ground in a place where patients have identified they could walk straight for as far as ≥200 meters without U-turns. Patients are allowed to wear regular footwear and an assistive device and/or orthotic as needed.

The number of steps walked in the course of two minutes will be reported to the patient, as well as the total number of steps walked during all 2 Minute Walk Tests performed.

b) U-Turn Test (UTT)

The aim of this test is to assess difficulties or unusual patterns in performing U-turns while walking a short distance at comfortable pace. The UTT is required to be performed indoor or outdoor, on even ground where patients are instructed to "walk safely and perform at least five successive U-turns, going back and forward between two points a few meters apart." Gait feature data (change in step counts, duration and asymmetry during U-turns, U-turn duration) during this task will be captured from smartphone sensors. Patients are allowed to wear regular footwear and an assistive device and/or orthotic as needed. The speed of turning will be reported to the patient.

c) Continuous Analysis of Gait (CAG)

Continuous recording of gait feature data (step counts, duration, and asymmetry) captured from smartphone sensors will allow passive monitoring of daily volume and quality of walking dynamics.

The radius of the patient's activities will be reported to the patient. This radius will be expressed in standard dimensions as well as in familiar, lay terms (for example: size of a football field).

d) Static Balance Test (SBT)

The aim of this test is to assess a person's static balance function as in one of the items (i.e., standing unsupported) of the widely used Berg Balance Scale (BBS), which is a 14-item objective measure designed to assess static balance and fall risk in adult populations (Berg 1992). Data will be captured from smartphone sensors.

The patients are asked to stand still unsupported for 30 seconds with relaxed arms, straight alongside the body if possible, and with the smartphone kept in a running band in a median, frontal position. Individuals with increased risk of falling and/or impaired static balance function may demonstrate altered postural control [sway] (Wai 2014).

The variations in the balance movement will be reported to the patient in terms of the sway path length and depicted in symbols (for example: solid large rock, small rock). The animated sway path will be shown as an easy to understand representation of balance variation.

e) Results

Examples of ambulation qualimetric activity parameters have been developed from the U-turn test (UTT), the 2-minute walk test (2MWT), the static balance test (SBT) and continuous analysis of gait (CAG) from passive monitoring described above.

As an example of ambulation qualimetric activity parameters measuring fluctuations of walking quality in the UTT and continuous analysis of gait from the passive monitoring, the turning speed from UTT, the number of daily turns while walking and the average daily turning speed are depicted in the graph below (interim analysis of clinical trial NCT02952911) to illustrate the ability of intra-subject day-to-day monitoring of these qualimetric parameters to detect a multiple sclerosis relapse. Clear differences in active test U-turn speed measured with the 5UTT was observed in this example between prior to reporting a relapse and after (Wilcoxon rank sum test; FIG. 4, panel b). Turning behavior in passive monitoring was also different before versus after relapse onset/reporting for the number of daily turns (FIG. 4, panel c), while the average daily turn speed remained unchanged (FIG. 4, panel d):

Some examples of ambulation qualimetric activity parameters derived from the SBT as described above and captured as continuous outcome variables reflecting intra-test fluctuations that measure gait and balance integrity are non-exhaustively listed as followed: 1) the sway jerkiness: time derivative of acceleration (Mancini 2012), 2) the sway path: total length of trajectory, 3) the sway range.

Some examples of ambulation qualimetric activity parameters derived from the 2MWT as described above and captured as continuous outcome variables reflecting intra-test fluctuations that measure gait and balance integrity are non-exhaustively listed as followed: 1) walking step time duration, 2) walking step velocity (step/second), 3) step asymmetry rate (difference of step duration between one step to the next divided by mean step duration), 4) the step length and total distance walked through biomechanical modelling, 5) the deceleration index by epoch, 6) the 5) the asymmetry index by epoch.

The mobile device can also be adapted for performing or acquiring data from Continuous Analysis of Gait (CAG). Continuous recording of gait feature data (step counts, duration, and asymmetry, as well as arm swing dynamic while walking) captured from sensors will allow passive monitoring of daily volume and quality of walking dynamics. Activity detection is a prior step to gait detection and analysis and activity analysis. It may be based on different, more or less complex approaches (Alsheikh 2015 or Ordóñez 2016), which considers windows of one second as active if the standard deviation of the accelerometer signal is above 0.01 g. The test is typically performed daily. Some examples of ambulation qualimetric activity parameters derived from the CAG as described above and captured as continuous outcome variables reflecting intra-test fluctuations that measure gait and balance integrity are, non-exhaustively, listed as follows: 1) the frequency distribution of the number of steps detected within each interval of continuous walking, 2) the walking step duration/velocity over time, 3) the step length variations over time derived through biomechanical modelling, 4) the elevation gain over time, 5) the frequency distribution of the sit/stand transitions and turns.

Example 4: A Computer-Implemented IPS Tests De-Convoluting Cognition and Estimating Learning A computer-implemented IPS test for smartphone devices was created. In one step, the computer-implemented IPS test determines the information processing speed by measuring the response time for symbol matching tasks using test symbols which are not familiar (e.g., no naïve numbers or symbols or symbols which are structurally or symbolically similar) to the patient performing the task. Test symbols which are useful for the IPS test show little similarity to letters or mathematical notation and should, therefore, also be independent of influences such as cultural background, reading and writing capabilities or educational attainment. Such test symbols can, therefore, also be used for children or subjects with low educational attainment (e.g., illiterate people). Moreover, in order to improve visual recognition, the test symbols shall follow a simple design principle with less detail. The symbols may be designed as symbol pairs having characteristic features at opposite sides of a mirror axis (e.g., left/right, up/down features) or as recognizable singleton symbols with rotational symmetry, directional orientation or characteristic edges; see FIGS. 13A-13F.

The test is performed by showing the patient, on a display, the test symbol and a legend which allocates different test symbols shown during the test to naïve numbers or other naïve symbols such as letters. These naïve numbers or other naïve symbols are also present on the keypad such that the subject performing the test can press the key which carries the naïve number or naïve symbol being allocated to the test symbol (see FIG. 14A). It will be understood that the response time in the IPS test for this task depends on the reaction time, the processing time for hand motor output and the time for cognitive information processing.

In the step of IPS testing described before, iterations of fixed test symbol matching sequences, wherein each sequence consists of matching tasks for at least 6 different test symbols, can be performed. The said iterations are followed by a new randomized test symbol matching sequence. An improvement in response time between the first and the last iteration indicates cognitive learning capabilities of the subject or a standard test response time and the response time in a randomized symbol matching sequence run. Three test symbol matching sequences are performed before, in the fourth matching sequence run, randomized symbols are shown in the sequence. Moreover, the test symbol matching is carried out as in standard clinical SDMT. The legend for the symbols, the size of the symbols, the keypad and other parameters displayed on the smartphone device used for carrying out the IPS test are kept at constant conditions as far as the dimension, appearance, contrast etc. are concerned in order to avoid sensory influences which are not related to the information processing speed (see FIG. 14). The IPS test is carried out for 90 seconds. This measurement of velocity prior and after the iterations of identical sequences allows for estimation of the cognitive capabilities, in particular, learning capabilities (see FIG. 12).

The IPS test, in a further step, determines a baseline information processing speed by measuring a baseline response time. Said baseline response time is determined by measuring the time for matching a naïve number or symbol to the matching naïve number or symbol on a keypad of the smartphone device (see FIG. 14B). The naïve number or symbol shall be selected such that the individual which carries out the test can perform the matching without substantial cognitive effort. More typically, numbers from 0 to 9 may be used as naïve numbers. Such a baseline response time using naïve number or symbol matching will be mainly dependent on the reaction time and processing time for hand motor output. Cognitive tasks will play only a minor role and will not contribute significantly to the baseline response time. Therefore, the information processing speed determined in the subsequent steps can be de-convoluted by said baseline response time into reaction time and processing time for hand motor output and time for cognitive information processing (see FIG. 11).

Thus, in the computer-implemented IPS test run on a smartphone device, the difference in response time between a task comprising reaction time, processing time for hand motor output, and time for cognitive information processing (test matching different non-naïve test symbols as described above to a legend which allocates said different test symbols shown during the test to naïve numbers or other naïve symbols, such as letters, by pressing the respective key on a keypad) and a task comprising reaction time and processing time for hand motor output (baseline task, matching a naïve number or symbol to the matching naïve number or symbol on a keypad) is determined as one cognitive qualimetric activity parameter being part of the dataset to be analyzed.

The IPS test described before is helpful for the clinical management of patients suffering from multiple sclerosis (MS) since information processing speed is a prevalent cognitive impairment in MS. The test aims at detecting even subtle changes in cognitive functions of MS patients and can be used in clinical settings or self-administration approaches.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method of assessing a cognition and movement disease or disorder in a subject suspected to suffer therefrom, the method comprising:
   a) using a mobile device having one or more sensors to obtain a dataset of activity measurements, wherein at least some of the activity measurements are obtained using a touch sensor configured to detect one or more activity measurements from the group consisting of duration of touchscreen contacts, deviation between touchscreen contacts and center of closest target digit key, mistyped touch screen contacts, double touch asynchrony, pinching target precision, pinching finger movement asymmetry, pinching finger velocity and pinching finger asynchrony;
   b) determining a qualimetric activity parameter for cognition and/or fine motoric activity from a preexisting dataset of cognition and/or fine motoric activity measurements from the subject; and
   c) comparing the determined qualimetric activity parameter to a reference; and
   d) based upon the comparison of step c), assessing the cognition and movement disease or disorder.

2. The method of claim 1, wherein the cognition and movement disease or disorder is a disease or disorder of the central and/or peripheral nervous system affecting the pyramidal, extrapyramidal, sensory or cerebellar system, or a neuromuscular disease or is a muscular disease or disorder.

3. The method of claim 2, wherein the cognition and movement disease or disorder is selected from the group consisting of: multiple sclerosis (MS), neuromyelitis optica (NMO) and NMO spectrum disorders, stroke, a cerebellar disorder, cerebellar ataxia, spastic paraplegia, essential tremor, myasthenia and myasthenic syndromes or other forms of neuromuscular disorders, muscular dystrophy, myositis or other muscular disorders, a peripheral neuropathy, cerebral palsy, extrapyramidal syndromes, Parkinson's disease, Huntington's disease, Alzheimer's disease, other forms of dementia, leukodystrophies, autism spectrum disorders, attention-deficit disorders (ADD/ADHD), intellectual disabilities as defined by DSM-5, impairment of cognitive performance and reserve related to aging, Parkinson's disease, Huntington's disease, a polyneuropathy, motor neuron diseases and amyotrophic lateral sclerosis (ALS).

4. The method of claim 1, wherein the qualimetric activity parameter is a cognitive qualimetric activity parameter indicative of fluctuations in neurocognitive functions, a hand/arm function qualimetric activity parameter indicative of fluctuations in manual dexterity or an ambulation qualimetric activity parameter indicative of movement fluctuations.

5. The method of claim 1, wherein the dataset of cognition and/or fine motoric activity measurements comprises data from a pinching test performed on a sensor surface of the mobile device and/or from a U-turn test (UTT), a 2-minute walk test (2MWT), a static balance test (SBT) or continuous analysis of gait (CAG) from passive monitoring.

6. The method of claim 1, wherein the dataset of cognition activity measurements comprises data from an Information Processing Speed (IPS) test on a sensor surface of the mobile device.

7. The method of claim 1, further comprising adapting the mobile device for carrying out one or more of UTT, 2MWT, SBT, CAG, Draw a Shape, Pinching and IPS tests.

8. The method of claim 7, wherein the mobile device is a smartphone, smartwatch, wearable sensor, portable multimedia device or tablet computer.

9. The method of claim 1, wherein the reference is a reference qualimetric activity parameter for cognition and/or fine motoric activity derived from a dataset of cognition and/or fine motoric activity measurements obtained from the subject at a time point prior to the time point when the dataset of cognition and/or fine motoric activity measurements referred to in step a) has been obtained from the subject.

10. The method of claim 9, wherein a worsening between the determined qualimetric activity parameter and the reference is indicative of a subject that suffers from the cognition and movement disease or disorder.

11. The method of claim 1, wherein the reference is a reference qualimetric activity parameter for cognition and/or fine motoric activity derived from a dataset of cognition and/or fine motoric activity measurements obtained from a subject or group of subjects known to suffer from the cognition and movement disease or disorder.

12. The method of claim 11, further comprising, when the determined qualimetric activity parameter is essentially identical to the reference, indicating that the subject suffers from the cognition and movement disease or disorder.

13. The method of claim 1, wherein the reference is a reference qualimetric activity parameter for cognition and/or fine motoric activity derived from a dataset of cognition and/or fine motoric activity measurements obtained from a subject or group of subjects known not to suffer from the cognition and movement disease or disorder.

14. The method of claim 13, further comprising, when the determined qualimetric activity parameter is worsened compared to the reference, indicating that the subject suffers from the cognition and movement disease or disorder.

15. A method for recommending a therapy for a cognition and movement disease or disorder, comprising performing the method of claim 1 and performing the further step of recommending the therapy when the cognition and movement disease or disorder is assessed.

16. A method for determining efficacy of a therapy against a cognition and movement disease or disorder, comprising performing the method of claim 1 and performing the further step of determining a therapy response when improvement of the cognition and movement disease or disorder occurs in the subject upon therapy and determining a failure of response when worsening of the cognition and movement disease or disorder occurs in the subject upon therapy or when the cognition and movement disease or disorder remains unchanged.

17. A method of monitoring a cognition and movement disease or disorder in a subject, comprising determining whether the cognition and movement disease or disorder improves, worsens or remains unchanged in a subject by carrying out the steps of claim 1 at least twice during a predefined monitoring period.

18. A mobile device, comprising:
a processor;
a sensor;
a database; and
software tangibly embedded on said mobile device, the software configured to:
  obtain a dataset of activity measurements, wherein at least some of the activity measurements are obtained using a touch sensor configured to detect one or more activity measurements from the group consisting of duration of touchscreen contacts, deviation between touchscreen contacts and center of closest target digit key, mistyped touch screen contacts, double touch asynchrony, pinching target precision, pinching finger movement asymmetry, pinching finger velocity and pinching finger asynchrony;
  determine a qualimetric activity parameter for cognition and/or fine motoric activity from a preexisting dataset of cognition and/or fine motoric activity measurements from said subject;
  compare the determined qualimetric activity parameter to a reference; and
  based upon the comparison, assess the cognition and movement disease or disorder.

19. The mobile device of claim 18, wherein the software is further configured to identify a subject suffering from a cognition and movement disease or disorder.

20. The mobile device of claim 18, the device being configured for monitoring a subject suffering from a cognition and movement disease in at least one of the following settings:
investigating drug efficacy; clinical trials; facilitating and/or aiding therapeutic decision making;
supporting hospital management; supporting rehabilitation measure management, supporting health insurances assessments and management; supporting decisions in public health management; and life style and/or therapy recommendations.

21. A system, comprising:
a mobile device having a sensor; and
a remote device having a processor, a database, and software tangibly embedded on the remote device, the software configured to:
  obtain a dataset of activity measurements, wherein at least some of the activity measurements are obtained using a touch sensor configured to detect one or more activity measurements from the group consisting of duration of touchscreen contacts, deviation between touchscreen contacts and center of closest target digit key, mistyped touch screen contacts, double touch asynchrony, pinching target precision, pinching finger movement asymmetry, pinching finger velocity and pinching finger asynchrony;
  determine a qualimetric activity parameter for cognition and/or fine motoric activity from a preexisting dataset of cognition and/or fine motoric activity measurements from said subject;
  compare the determined qualimetric activity parameter to a reference; and
  based upon the comparison, assess the cognition and movement disease or disorder;
wherein the mobile device and the remote device are operatively linked to each other.

22. The system of claim 21, wherein the software is further configured to identify a subject suffering from a cognition and movement disease or disorder.

23. The system of claim 21, the system being configured for monitoring a subject suffering from a cognition and movement disease in at least one of the following settings:

investigating drug efficacy; clinical trials; facilitating and/or aiding therapeutic decision making;

supporting hospital management; supporting rehabilitation measure management, supporting health insurances assessments and management; supporting decisions in public health management; and life style and/or therapy recommendations.

24. A method of assessing a cognition and/or movement disease or disorder in a subject suspected to suffer therefrom, comprising:
  a) using a mobile device to obtain a dataset of cognition and/or fine motor activity measurements from the subject, wherein at least some of the cognition and/or fine motor activity measurements are obtained using a touch sensor configured to detect one or more cognition and/or fine motor activity measurements from the group consisting of duration of touchscreen contacts, deviation between touchscreen contacts and center of closest target digit key, mistyped touch screen contacts, double touch asynchrony, pinching target precision, pinching finger movement asymmetry, pinching finger velocity and pinching finger asynchrony;
  b) determining a qualimetric activity parameter for cognition and/or fine motor activity from the dataset;
  c) comparing the qualimetric activity parameter to a reference; and
  d) using the comparison of step c) to assess the subject for the cognition and movement disease or disorder.

25. The method of claim 24, further comprising:
  e) recommending a therapy based on the assessment of the cognition and movement disease or disorder.

26. The method of claim 25, wherein the therapy comprises at least one of drug-based therapies, surgeries, psychotherapy, physical therapy, lifestyle changes, rehabilitation measures, and dietary changes.

27. The method of claim 26, wherein the therapy is drug-based and the drug is selected from the group consisting of: interferon beta-1a, interferon beta-1b, glatiramer acetate, mitoxantrone, natalizumab, fingolimod, teriflunomide, dimethyl fumarate, alemtuzumab, daclizumab, thrombolytic agents, recombinant tissue plasmin activator, acetylcholinesterase inhibitors, tacrine, rivastigmine, galantamine, donepezil, NMDA receptor antagonists, memantine, non-steroidal anti-inflammatory drugs, dopa carboxylase inhibitors, levodopa, tolcapone, entacapone, dopamine antagonists, bromocriptine, pergolide, pramipexole, ropinirole, piribedil, cabergoline, apomorphine, lisuride, MAO-B inhibitors, safinamide, selegiline, rasagiline, amantadine, anticholinergics, tetrabenazine, neuroleptics, benzodiazepines and riluzole.

28. The method of claim 25, wherein the efficacy of the therapy is determined by repeating steps (a) through (d).

* * * * *